US006001553A

United States Patent [19]
Broach et al.

[11] Patent Number: 6,001,553
[45] Date of Patent: Dec. 14, 1999

[54] FUNCTIONAL EXPRESSION OF MAMMALIAN ADENYLYL CYCLASE IN YEAST

[75] Inventors: James R. Broach, Princeton, N.J.; John P. Manfredi, Ossining; Joshua Trueheart, Nyack, both of N.Y.

[73] Assignee: Cadus Pharmaceutical Corporation, Tarrytown, N.Y.

[21] Appl. No.: 08/732,218

[22] PCT Filed: Apr. 26, 1995

[86] PCT No.: PCT/US95/05149

§ 371 Date: Jan. 14, 1997

§ 102(e) Date: Jan. 14, 1997

[87] PCT Pub. No.: WO95/30012

PCT Pub. Date: Nov. 9, 1995

Related U.S. Application Data

[63] Continuation-in-part of application No. 08/233,700, Apr. 26, 1994, abandoned.

[51] Int. Cl.$^6$ .............................. C12Q 1/00; C12N 1/14; C12N 9/88
[52] U.S. Cl. ..................... 435/4; 435/252.2; 435/254.21; 435/232
[58] Field of Search ....................... 435/4, 252.2, 254.21, 435/232

[56] References Cited

U.S. PATENT DOCUMENTS

| | | | |
|---|---|---|---|
| 5,334,521 | 8/1994 | Ishikawa | 435/172.1 |
| 5,482,835 | 1/1996 | King et al. | 435/6 |

FOREIGN PATENT DOCUMENTS

| | | |
|---|---|---|
| 0301954 A3 | 2/1989 | European Pat. Off. . |
| 0 529 622 | 3/1993 | European Pat. Off. . |
| 0 543 137 | 5/1993 | European Pat. Off. . |
| WO 94/23025 | 10/1994 | WIPO . |

OTHER PUBLICATIONS

Glaser, P. et al. (1988) "The calmodulin–sensitive adenylate cyclase of *Bordetella pertussis*: cloning and expression in *Escherichia coli*" Molecular Microbiology, vol. 22, No. 1, pp. 19–30, 1988.

Bourne, H.R. et al. (1990) "The GTPase superfamily: a conserved switch for diverse cell functions" Nature, vol. 348, pp. 125–132, Nov. 1990.

Casperson, G.F. et al. (1985) "Isolation of the gene encoding adenylate cyclase in *Saccharomyces cerevisiae*" Proceedings of the National Academy of Sciences, USA, vol. 82, pp. 5060–5063, Aug. 1985.

Rüth, J. et al. (1992) "The cauliflower mosaic virus 35S promoter is regulated by cAMP in *Saccharomyces cerevisiae*" Molecular and General Genetics, vol. 235, pp. 265–372, 1992.

Matsumoto, K. et al. (1982) "Cyclic AMP may not be involved in catabolite repression in *Saccharomyces cerevisiae*: evidence from mutants capable of utilizing it as an adenine source" Journal of Bacteriology, vol. 150, No. 1, pp. 277–285, Apr. 1982.

Blumer, K.J. et al. (1990) "Beta and gamma subunits of a yeast guanine nucleotide–binding protein are not essential for membrane association of the alpha subunit but are required for receptor coupling" Proceedings of the National Academy of Sciences, USA, Jun. 1990.

Taussig, R. et al. (1993a) "Inhibition of adenylyl cyclase by Gi alpha" Science, vol. 261, pp. 218–221, Jul. 1993.

Taussig, R. et al. (1993b) "Regulation of purified type I and type II adenylylcyclase by G protein betagamma subunits" Journal of Biological Chemistry, vol. 268, No. 1, pp. 9–12, Jan. 1993.

Casperson, G. et al., "A Guanine Nucleotide–sensitive Adenylate Cyclase in the Yeast *Saccharomyces cerevisiae*," *The Journal of Biological Chemistry*, vol. 258, No. 13, 7911–7914 (1983).

Chen, J. and Iyengar, R., "Inhibition of Cloned Adenylyl Cyclases by Mutant–activated Gi–α and Specific Suppression of Type 2 Adenylyl Cyclase Inhibition by Phorbol Ester Treatment," *The Journal of Biological Chemistry*, vol. 268, No. 17, 12253–12256 (1993).

Federman, A. et al., "Hormonal Stimulation of Adenylyl Cyclase Through $G_i$–protein βγ Subunits," *Nature*, vol. 356, 159–161 (1992).

Kataoka, T. et al., "DNA Sequence and Characterization of the *S. cerevisiae* Gene Encoding Adenylate Cyclase," *Cell*, vol. 43, 493–505 (1985).

King, K. et al., "Control of Yeast Mating Signal Transduction by a Mammalian β2 –Adrenergic Receptor and Gsα Subunit," *Science*, vol. 250 121–123 (1990).

Mitts, M. et al., "Adenylate Cyclase in *Saccharomyces cerevisiae* Is a Peripheral Membrane Protein," *Molecular and Cellular Biology*, vol. 10, No. 8, 3873–3883 (1990).

Paindavoine, P. et al., "A Gene from the Variant Surface Glycoprotein Expression Site Encodes One of Several Transmembrane Adenylate Cyclases Located on the Flagellum of *Trypanosoma brucei*," *Molecular and Cellular Biology*, vol. 12, No. 3, 1218–1225 (1992).

Tang, W. et al., "Expression and Characterization of Calmodulin–activated (Type I) Adenylylcyclase," *The Journal of Biological Chemistry*, vol. 266, No. 13, 8595–8603 (1991).

Taussig, R. et al., "Expression and Purification of Recombinant Adenylyl Cyclases in S f 9 Cells," *Methods in Enzymology*, vol. 238, 95–108 (1994).

(List continued on next page.)

*Primary Examiner*—Robert A. Wax
*Attorney, Agent, or Firm*—Lahive & Cockfield LLP; Giulio A. DeConti, Jr.; Peter C. Lauro

[57] ABSTRACT

Mammalian adenylyl cyclases are functionally expressed in yeast cells. The yeast cells may be used to screen for inhibitors or activators of the adenylyl cyclase, or of a regulator of adenylyl cyclase which is functionally co-expressed in the yeast cell. Methods of identifying such inhibitors, activators and regulators are also disclosed.

83 Claims, 3 Drawing Sheets

OTHER PUBLICATIONS

Young, D. et al., "The Adenylyl Cyclase Gene from *Schizosaccharomyces pombe*," Proc. Natl. Acad. Sci. USA, vol. 86, 7989–7993 (1989).

Geller, Alfred I., et al., "Long–Term Increases In Neurotransmitter Release From Neuronal Cells Expressing A Constitutively Active Adenylate Cyclase From A Herpes SImplex Virus Type 1 Vector", Proc. Natl. Acad. Sci. vol. 90, pp. 7603–7607, Aug. 1993.

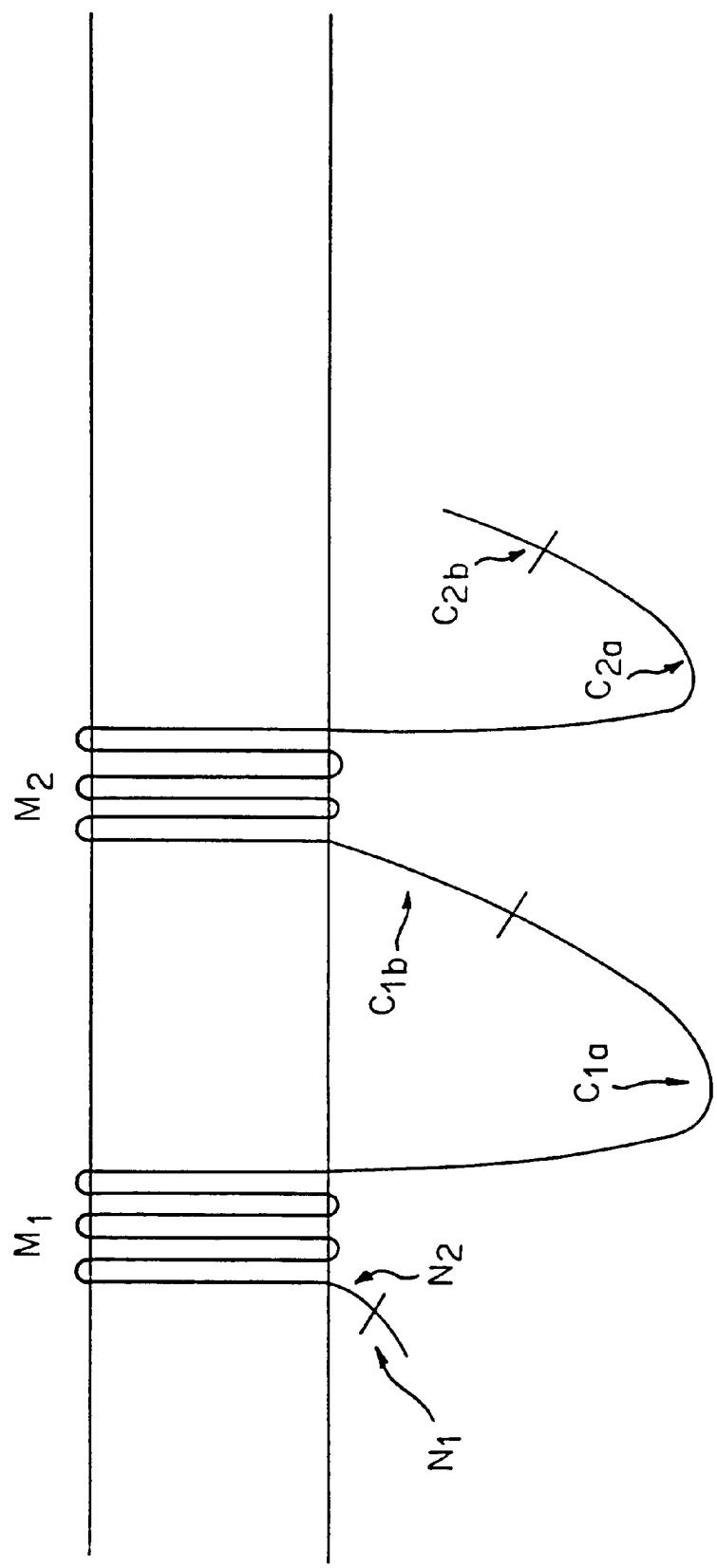

SEQUENCE LISTING

<160> NUMBER OF SEQ ID NOS: 13

<210> SEQ ID NO 1
<211> LENGTH: 13
<212> TYPE: DNA
<213> ORGANISM: synthetic construct
<220> FEATURE:
<223> OTHER INFORMATION: at positions 8 and 9, n can be any nucleic acid
      base

<400> SEQUENCE: 1
rmacccannc ayy                                                          13

<210> SEQ ID NO 2
<211> LENGTH: 55
<212> TYPE: DNA
<213> ORGANISM: synthetic construct

<400> SEQUENCE: 2
gccgtctcac atgagaagaa gaagatactt gagagataga gctgaagctg ctgca            55

<210> SEQ ID NO 3
<211> LENGTH: 51
<212> TYPE: DNA
<213> ORGANISM: synthetic construct

<400> SEQUENCE: 3
gcagcttcag ctctatctct caagtatctt cttcttctca tgtgagacgg c                51

<210> SEQ ID NO 4
<211> LENGTH: 42
<212> TYPE: DNA
<213> ORGANISM: synthetic construct

<400> SEQUENCE: 4
gctgctgctg ctggtggtgg tgaaggtttg caaagatccc gg                          42

<210> SEQ ID NO 5
<211> LENGTH: 50
<212> TYPE: DNA
<213> ORGANISM: synthetic construct

<400> SEQUENCE: 5
gatcccggga tctttgcaaa ccttcaccac caccagcagc agcagctgca                  50

<210> SEQ ID NO 6
<211> LENGTH: 29
<212> TYPE: DNA
<213> ORGANISM: synthetic construct

<400> SEQUENCE: 6
cagacatgtc ttggtttcgt ggcctcctg                                         29

<210> SEQ ID NO 7
<211> LENGTH: 36
<212> TYPE: DNA
<213> ORGANISM: synthetic construct

<400> SEQUENCE: 7
gcggatccaa ggtcatgacc agttcctgtg cagtgc                                 36

<210> SEQ ID NO 8
<211> LENGTH: 25

-continued

```
<212> TYPE: DNA
<213> ORGANISM: synthetic construct

<400> SEQUENCE: 8
catgactgaa gatcaaggtt tctcg                                          25

<210> SEQ ID NO 9
<211> LENGTH: 25
<212> TYPE: DNA
<213> ORGANISM: synthetic construct

<400> SEQUENCE: 9
gatccgagaa accttgatct tcagt                                          25

<210> SEQ ID NO 10
<211> LENGTH: 31
<212> TYPE: DNA
<213> ORGANISM: synthetic construct

<400> SEQUENCE: 10
gggcgtctcc catggccagc aacaacaccg c                                   31

<210> SEQ ID NO 11
<211> LENGTH: 29
<212> TYPE: DNA
<213> ORGANISM: synthetic construct

<400> SEQUENCE: 11
ggggtcgacc gaggctcctc aggttcctc                                      29

<210> SEQ ID NO 12
<211> LENGTH: 44
<212> TYPE: DNA
<213> ORGANISM: synthetic construct

<400> SEQUENCE: 12
cggctagcat ctatatacaa tgagtgaact tgaccagtta cggc                     44

<210> SEQ ID NO 13
<211> LENGTH: 39
<212> TYPE: DNA
<213> ORGANISM: synthetic construct

<400> SEQUENCE: 13
cgagcggccg ctcagttcca gattttgagg aagctgtcc                           39
```

FUNCTIONAL EXPRESSION OF MAMMALIAN ADENYLYL CYCLASE IN YEAST

This application is a continuation-in-part of Ser. No. 08/233,700, filed Apr. 26, 1994, now abandoned, hereby incorporated by reference. The benefit of the filing date of this application is hereby claimed under all applicable statutes and treaties.

BACKGROUND OF THE INVENTION

CROSS REFERENCE TO RELATED APPLICATIONS

A commonly owned application, U.S. Ser. No. 08/322,137, filed Oct. 13, 1994, incorporated by reference herein, relates to use of engineered yeast cells in screening for substances which modulate the activity of a mammalian surrogate of a yeast pheromone system protein, e.g., the yeast pheromone receptor, a G protein-coupled receptor.

1. Field of the Invention

The invention relates inter alia, to expression of a mammalian adenylyl cyclase in yeast, the transformed yeast cells, and their use, e.g., in identifying potential inhibitors or activators of the mammalian adenylyl cyclase, or of other proteins which are natively or artificially coupled to the mammalian adenylyl cyclase in the engineered yeast cell.

2. Description of the Background Art

Signal Transduction

In some instances, for a drug to cure a disease or alleviate its symptoms, the drug must be delivered to the appropriate cells, and trigger the proper "switches." The cellular switches are known as "receptors." Hormones, growth factors, neurotransmitters and many other biomolecules normally act through interaction with specific cellular receptors. Drugs may activate or block particular receptors to achieve a desired pharmaceutical effect. Cell surface receptors mediate the transduction of an "external" signal (the binding of a ligand to the receptor) into an "internal" signal (the modulation of a pathway in the cytoplasm or nucleus involved in the growth, metabolism or apotosis of the cell).

In many cases, transduction is accomplished by the following signaling cascade:

An agonist (the ligand) binds to a specific protein (the receptor) on the cell surface.

As a result of the ligand binding, the receptor undergoes an allosteric change which activates a transducing protein in the cell membrane.

The transducing protein activates, within the cell, production of so-called "second messenger molecules."

The second messenger molecules activate certain regulatory proteins within the cell that have the potential to "switch on" or "off" specific genes or alter some metabolic process.

This series of events is coupled in a specific fashion for each possible cellular response. The response to a specific ligand may depend upon which receptor a cell expresses. For instance, the response to adrenalin in cells expressing α-adrenergic receptors may be the opposite of the response in cells expressing β-adrenergic receptors.

The above "cascade" is idealized, and variations on this theme occur. For example, a receptor may act as its own transducing protein, or a transducing protein may act directly on an intracellular target without mediation by a "second messenger".

Signal Transduction Through G Proteins

Signals initiated by a variety of mammalian hormones and neurotransmitters are received by seven transmembrane domain receptors in the plasma membrane of cells and are transduced to intracellular effectors via heterotrimeric G proteins. Many different G proteins are known to interact with receptors. G protein signaling systems include three components: the receptor itself, a GTP-binding protein (G protein), and an intracellular target usually a protein.

The cell membrane acts as a switchboard. Messages arriving through different receptors can produce a single effect if the receptors acts on the same type of G protein. On the other hand, signals activating a single receptor can produce more than one effect if the receptor acts on different kinds of G proteins, or if the G proteins can act on different effectors.

The heterotrimeric G protein is composed of a guanine nucleotide-binding a subunit together with a tight complex of β and γ subunits. In their resting state, the G proteins, which consist of alpha ($\alpha$), beta ($\beta$) and gamma ($\gamma$) subunits, are complexed with the nucleotide guanosine diphosphate (GDP) and are in contact with receptors. When a hormone or other first messenger binds to receptor, the receptor changes conformation and this alters its interaction with the G protein. This spurs the a subunit to release GDP, and the more abundant nucleotide guanosine tri-phosphate (GTP), replaces it, activating the G protein. The G protein then dissociates to separate the α subunit from the still complexed beta and gamma subunits. The free G$\alpha$ and the G$\beta\gamma$ subunits both may be capable of influencing the activity of specific effector molecules (e.g., the enzymes adenylyl cyclase, cyclic GMP phosphodiesterase (PDE), phospholipase C, phospholipase $A_2$, and selected ion channels). The effector (which is often an enzyme) in turn converts an inactive precursor molecule into an active "second messenger," which may diffuse through the cytoplasm, triggering a metabolic cascade. After a few seconds, G protein signalling is terminated with the hydrolysis of GTP to GDP through the intrinsic GTPase activity of the G$\alpha$ subunit and the subsequent reassociation of G$\alpha$-GDP with G$\beta\gamma$ to form the inactive heterotrimer. This reassociation is driven by the high affinity of GDP-bound G$\alpha$ for G$\beta\gamma$.

Hundreds, if not thousands, of receptors convey messages through heterotrimeric G proteins, of which at least 17 distinct forms have been isolated. Although the greatest variability has been seen in the a subunit, several different β and γ structures have been reported. There are, additionally, several different G protein-dependent effectors.

The study of microorganisms indicates that the development of G protein signal transduction pathways arose early in the evolution of eukaryotic cells. G protein regulatory function is intrinsic to the response to mating pheromones in yeast (Whiteway et al. 1989) and the development of the cellular slime mold *Dictyostelium discoideum* is controlled by G protein-mediated responses to cAMP (Devreotes 1989).

The Role of Adenylyl Cyclase in G-Protein-Mediated Signal Transduction

Adenylyl cyclase is among the best studied of the effector molecules which function in mammalian cells in response to activated G proteins. Activation of adenylyl cyclase occurs when signals transduced from specific cellular receptors result in the release of GTP-bound G$\alpha$s. G$\alpha$s ("s" denotes stimulatory) was originally identified as a regulator of adenylyl cyclase activity in mutant S49 cells which lacked adenylyl cyclase activity. G$\alpha$s-GTP stimulated adenylyl cyclase activity in those cyc$^-$ cells (Northup et al. (1980)

Proc. Natl. Acad. Sci. USA 77, 6516-6520). The production of cAMP can be stimulated by pure GTP-γS-bound Gαs (GTP-γS is a non-hydrolyzable form of the nucleotide). Activation of cyclase by GTP-bound Gαs is reversed by excess Gβγ; inhibition is assumed to occur as an inactive G protein heterotrimer re-forms.

Molecules which signal through receptors that interact with another class of G proteins, Gαi (including Gαi1, Gαi2, and Gαi3), mediate inhibition of adenylyl cyclase. Upon agonist binding to Gi-coupled receptors, both activated Gαi protein and the released Gβγ complex appear to be capable of inhibiting the activity of adenylyl cyclase [Taussig et al. (1993) Science 261, 218–221]. The Gβγ complex may inhibit the enzyme's activity by reforming a heterotrimer with free Gαs, thereby sequestering that stimulatory molecule (Gilman (1984) Cell 36, 577–579). In addition, the Gαi subunit may directly inhibit adenylyl cyclase activity (Taussig et al. (1993) Science 261, 218–221.) A third mechanism for the negative regulation of adenylyl cyclase involves direct inhibition by the Gβγ complex. Purified type 1 adenylyl cyclase has been shown to be directly inhibited by βγ subunits (Taussig et al. (1993) J. Biol. Chem. 268, 9–12).

Cyclic nucleotides play an important role in the regulation of a multitude of cellular activities. The synthesis of adenosine 3', 5'-cyclic phosphate (cyclic adenosine monophosphate or cAMP) is catalyzed by adenylyl cyclase, an enzyme which, in mammalian cells, is an integral membrane protein. Cyclic AMP is a second messenger which acts in response to cellular signals through a specific protein kinase (cAMP-dependent protein kinase or protein kinase A) to phosphorylate target molecules, e.g., other protein kinases or proteins involved in transport or cellular morphology. Through stimulation of the kinase, intracellular cAMP mediates many of the effects of hormones in the regulation of cellular metabolism and cell growth. Cyclic AMP is hydrolyzed by several phosphodiesterases (PDE) and can be actively secreted from some cell types, presumably via a specific transporter, or sequestered from the cytoplasm via transporters present in the membranes of intracellular organelles.

In vertebrate cells, adenylyl cyclase is regulated by heterotrimeric G proteins [Gilman (1984) Cell 36, 577–579] while in yeast, RAS proteins regulate adenylyl cyclase [Toda et al. (1985) Cell 40, 27–36; Broek et al. (1985) Cell 41, 763–769]. In turn, the activity of both the heterotrimeric G proteins and RAS proteins are controlled by the forms of guanine nucleotides to which they are bound.

While most adenylyl cyclases are found associated with the plasma membrane, certain forms of the enzyme expressed in bacteria are cytosolic, as is a mammalian enzyme found in testis. Peripheral membrane adenylyl cyclases are expressed in *E. coli* (Aiba et al. 1984) and in *S. cerevisiae* (Kataoka et al. 1985). The adenylyl cyclase encoded by the ACG gene of Dictyostelium appears to have a single transmembrane domain (Pitt et al. 1992). A second adenylyl cyclase gene from Dictyostelium (ACA) (Pitt et al. 1992), the Drosophila rutabaga gene (Levin et al. 1992), and the six full-length cDNAs encoding mammalian adenylyl cyclases that have been cloned to date code for integral membrane proteins.

Yeast Pheromone System Proteins and Their Metabolic Function

Haploid yeast cells are able not only to grow vegetatively, but also to mate to form a diploid cell. The two mating types ("sexes") of haploid cells are designated a and α. The a cells produce the dodecapeptide a-factor, and the α cells, the tridecapeptide α-factor. Because a-factor and α-factor elicit a mating response in the yeast cell of the opposite "sex", they are called "pheromones". These pheromones, as well as other proteins specifically involved in the production or transport of, or response to, pheromones, are considered "pheromone system proteins".

The gene encoding a-factor pheromone, like the α-factor receptor gene, is an a cell-specific gene; a cell-specific genes are only expressed in a cells. The gene encoding α-factor pheromone, like the a-factor receptor gene, is an α cell-specific gene; α cell-specific genes are only expressed in a cells. Other yeast genes belong to a haploid-specific gene set and are expressed in haploid cells (a cells or α cells) but not in diploid (a/α) cells. In addition, there exists a diploid cell-specific gene set, including those genes involved in sporulation.

In eukaryotic cells, RNA polymerase II promoters contain a specific sequence (the TATA box) to which the transcription factor TFIID (TATA binding protein or TBP) binds. An active transcription initiation complex includes TFIID, accessory initiation proteins, and RNA Pol II. As in higher eukaryotic cells, the TATA box is an essential control sequence in yeast promoters. Yeast TATA-box-binding protein (TBP) was identified by its ability to substitute in function for mammalian TFIID [Buratowski et al., Nature 334, 37 (1988); Cavallini et al., Nature 334, 77 (1988)]. With only a few apparent exceptions [transcription of some glycolytic enzyme genes, see Struhl, Mol. Cell. Biol. 6, 3847 (1986) and Ogden et al., Mol. Cell Biol. 6, 4335 (1986)] transcription of yeast genes requires the proximal TATA box element and TFIID binding for initiation of transcription. Also required for efficient transcription are gene-specific activator proteins; the precise mechanism whereby these gene-specific regulatory proteins influence transcription has not been completely elucidated.

MCM1p (encoded in the MCM1 gene) is a non-cell-type-specific transcription factor in yeast. MCM1p acts alone or in concert with other regulatory proteins to control expression of a- and α-cell specific genes. Yeast mating type loci encode the regulatory proteins that contribute to the control of cell type-specific expression. These proteins are Mata1p (encoded by the MATa gene) and Matα1p and Matα2p (encoded by the MATα locus). MCM1p activates transcription of a-specific genes by binding to an upstream activation sequence (UAS) located in the control region of a-specific genes. Matα1p and MCM1p interact to enhance each other's binding to specific UAS binding sites to activate α-cell-specific gene transcription in α-cells. Matα2p associates with MCM1p to repress a-specific gene transcription in α-cells. In diploid (a/α) cells, Mata1p and Matα2p associate to repress the transcription of haploid-specific genes. The Matα1p/Matα2p regulatory entity is found only in diploid cells.

Yeast contain two genes encoding the α-factor pheromone, MFα1 and MFα2. Analysis of yeast bearing mutations in these sequences indicates that MFα1 gives rise to the majority of α-factor produced by cells. Expression occurs at a higher level from MFα1 than from MFα2 (Kurjan, Mol. Cell. Biol. 5, 787 (1985). The MFα1 gene of yeast encodes a 165 aa precursor protein containing an 85 aa leader sequence at the N-terminus. The leader includes a 19 aa signal sequence and a 66 aa sequence which contains sites for the addition of three oligosaccharide side chains (Kurjan and Herskowitz, Cell 39, 933 (1982); Singh et al. Nuc. Acids Res. 11, 4049 (1983); Julius et al. Cell 36, 309 (1984). Four tandem copies of the 13 aa α-factor are present in the C-terminal portion of the precursor; 6–8 aa spacer peptides precede the α-factor sequences (see FIG. 2).

After translocation of the nascent α-factor polypeptide to the ER, the signal sequence is cleaved from the precursor protein to yield pro-α-factor (Waters et al. J. Biol. Chem. 263, 6209 (1988). The core N-linked carbohydrate is added to three sites in the N-terminus of pro-α-factor (Emter et al. Biochem. Biophys. Res. Commun. 116, 822 (1983); Julius et al. Cell 36, 309 (1984); Julius et al. Cell 37, 1075 (1984). Additional glycosylation occurs in the Golgi prior to cleavage of pro-α-factor by the KEX2 endopeptidase. This enzyme cleaves within each of the spacer repeats leaving a Lys-Arg sequence attached to the C-terminus of α-factor peptide (Julius et al. Cell 37, 1075 (1984). The Lys-Arg sequence is removed by the action of the KEX-1 protease (Dmochowska et al. Cell 50, 573 (1987). The additional spacer residues present at the N-terminus of α-factor peptide are removed by the dipeptidyl aminopeptidase encoded by STE13 (Julius et al. Cell 32, 839 (1983). Four α-factor peptides are released from each precursor protein via the proteolytic processing outlined above and the mature α-factor is secreted from the cell.

Precursors of the 12 aa mature a-factor peptide are encoded in the MFa1 and MFa2 genes and are 36 aa and 38 aa residues, respectively (for schematic of MFa1 gene see FIG. 5). The precursors contain one copy of a-factor and the products of the two genes differ in sequence at one amino acid. The two forms of a-factor are produced in equal amounts by a cells (Manney et al. in *Sexual interactions in eukaryotic microbes*, p21, Academic Press, New York (1981).

Processing of a-factor entails a process that differs in every detail from that of α-factor. The processing of a-factor begins in the cytosol and involves the farnesylation of the C-terminal cysteine residue near the carboxyl terminus (-CVIA) by a farnesyl transferase (Schafer et al. Science 245, 379 (1989); Schafer et al. Science 249, 1133 (1990). The α and β subunits of the farnesyl transferase are encoded by the RAM2 and RAM1 genes, respectively (He et al. Proc. Natl. Acad. Sci. 88, 11373 (1991). Subsequent to farnesylation is the proteolytic removal of the three amino acids that are C-terminal to the modified cysteine by a membrane-bound endoprotease. Next, the carboxy-terminal farnesylated cysteine residue is modified further: the carboxyl group is methylated by the product of the STE14 gene. STE14p is a membrane-bound S-farnesyl-cysteine carboxyl methyl transferase (Hrycyna et al. EMBO. J. 10, 1699 (1991). The mechanisms of the N-terminal processing of a-factor have not been elucidated. After processing of the precursors is complete, mature a-factor is transported to the extracellular space by the product of the STE6 gene (Kuchler et. al. EMBO J. 8, 3973 (1989), an ATP-binding cassette (ABC) transporter.

In normal *S. cerevisiae* (budding yeast) a cells, the α-factor binds the G protein-coupled membrane receptor STE2. The G protein dissociates into the $G_\alpha$ and $G_{\beta\gamma}$ subunits, and the $G_{\beta\gamma}$ binds an unidentified effector, which in turn activates a number of genes. STE20, a kinase, activates STE5, a protein of unknown function. STE5 activates STE11 kinase, which stimulates STE7 kinase, which induces the KSS1 and/or FUS3 kinases. These switch on expression of the transcription factor STE12. STE12 stimulates expression of a wide variety of genes involved in mating, including FUS1 (cell fusion), FAR1 (cell-cycle arrest), STE2 (the receptor), MFA1 (the pheromone), SST2 (recovery), KAR3 (nuclear fusion) and STE6 (pheromone secretion). Other genes activated by the pathway are CHS1, AGα1, and KAR3. The multiply tandem sequence TGAAACA has been recognized as a "pheromone response element" found in the 5'-flanking regions of many of the genes of this pathway.

One of the responses to mating pheromone is the transient arrest of the yeast cell in the G1 phase of the cell cycle. This requires that all three G1 cyclins (CLN1, CLN2, CLN3) be inactivated. It is believed that FUS3 inactivates CLN3, and FAR1 inhibits CLN2. (The product responsible for inactivating CLN1 is unknown).

The growth arrest is terminated by a number of different mechanisms. First, the α-factor receptor is internalized following binding of the pheromone, resulting in a transient decrease in the number of pheromone binding sites. Second, the C-terminal tail of the receptor is phosphorylated consequent to ligand binding, resulting in uncoupling of the receptor from the transducing G proteins. Third, pheromone-induced increases in expression of GPA1p (the Gα-subunit of the heterotrimeric G protein) increase the level of the α subunit relative to the $G_\beta$ and $G_\gamma$ subunits, resulting in reduction in the level of free $G_{\beta\gamma}$ and consequent inactivation of the pheromone response pathway. Additional mechanisms include induction of the expression of SST2 and BAR1 and phosphorylation of the α subunit (perhaps by SVG1).

Signaling is inhibited by expression of a number of genes, including CDC36, CDC39, CDC72, CDC73, and SRM1. Inactivation of these genes leads to activation of the signaling pathway.

A similar pheromone signaling pathway may be discerned in α cells, but the nomenclature is different in some cases (e.g., STE3 instead of STE2).

Other yeast also have G protein-mediated mating factor response pathways. For example, in the fission yeast *S. pombe*, the M factor binds the MAP3 receptor, or the P-factor the MAM2 receptor. The dissociation of the G protein activates a kinase cascade (BYR2, BYR1, SPK1), which in turn stimulates a transcription factor (STE11). However, in *S. pombe*, the Gα subunit transmits the signal, and there are of course other differences in detail.

Expression of Foreign Proteins in Yeast Cells

A wide variety of foreign proteins have been produced in *S. cerevisiae*, that remain in the yeast cytoplasm or are directed through the yeast secretory pathway (Kingsman et al. TIBTECH 5, 53 (1987). These proteins include, as examples, insulin-like growth factor receptor (Steube et al. Eur. J. Biochem. 198, 651 (1991), influenza virus hemagglutinin (Jabbar et al. Proc. Natl. Acad. Sci. 82, 2019 (1985), rat liver cytochrome P-450 (Oeda et al. DNA 4, 203 (1985) and functional mammalian antibodies (Wood et al. Nature 314, 446 (1985). Use of the yeast secretory pathway is preferred since it increases the likelihood of achieving faithful folding, glycosylation and stability of the foreign protein. Thus, expression of heterologous proteins in yeast often involves fusion of the signal sequences encoded in the genes of yeast secretory proteins (e.g., α-factor pheromone or the SUC2 [invertase] gene) to the coding region of foreign protein genes.

A number of yeast expression vectors have been designed to permit the constitutive or regulated expression of foreign proteins. Constitutive promoters are derived from highly expressed genes such as those encoding glycolytic enzymes like phosphoglycerate kinase (PGK1) or alcohol dehydrogenase I (ADH1) and regulatable promoters have been derived from a number of genes including the galactokinase (GAL1) gene. In addition, supersecreting yeast mutants can be derived; these strains secrete mammalian proteins more efficiently and are used as "production" strains to generate large quantities of biologically active mammalian proteins in yeast (Moir and Davidow, Meth. in Enzymol. 194, 491 (1991).

Heterologous G protein-coupled receptors have been functionally expressed in *S. cerevisiae*. Marsh and Hershkowitz, (Cold Spring Harbor Symp., Quant. Biol., 53: 557–65 (1988)) replaced the *S. cerevisiae* STE2 with its homologue from *S. Kluyven*. More dramatically, a mammalian beta-adrenergic receptor and Gα subunit have been expressed in yeast and found to control the yeast mating signal pathway. King, et al., Science, 250: 121–123 (1990).

Duke University, WO92/05244 (Apr. 2, 1992) describes a transformed yeast cell which is incapable of producing a yeast G protein α subunit, but which has been engineered to produce both a mammalian G protein α subunit and a mammalian receptor which is "coupled to" (i.e., interacts with) the aforementioned mammalian G protein α subunit. Specifically, Duke reports expression of the human beta-2 adrenergic receptor (hβAR), a seven transmembrane receptor (STR), in yeast, under control of the GAL1 promoter, with the hβAR gene modified by replacing the first 63 base pairs of coding sequence with 11 base pairs of noncoding and 42 base pairs of coding sequence from the STE2 gene. (STE2 encodes the yeast α-factor receptor). Duke co-expressed a rat G protein α subunit in the same cells, yeast strain 8C, which lack the cognate yeast protein. Duke found that the modified hβAR was functionally integrated into the membrane, as shown by studies of the ability of isolated membranes to interact properly with various known agonists and antagonists of hβAR. The ligand binding affinity for yeast-expressed hβAR was said to be nearly identical to that observed for naturally produced hβAR. Ligand binding resulted in G protein-mediated signal transduction. Duke did not co-express a mammalian adenylyl cyclase in these cells.

Expression of Heterologous Adenylyl Cyclases in Yeast

African trypanosomes are protozoan parasites which are able to evade host immune defenses by altering their surface glycoproteins. The variable antigenicity is accomplished by sequential expression of genes encoding coat proteins. The variable surface glycoprotein genes (VSG) are transposed from silent regions to active, telomere-linked expression sites. Additional open reading frames (ORFs) termed the Expression Site Associated Genes (ESAGs), are found at these expression sites. ESAG4, cloned from *Trypanosoma brucei*, contains a sequence which is homologous to *S. cerevisiae* adenylyl cyclase [Pays et al. (1989) Cell 57, 835–845]. In addition, an ESAG from *Trypanosoma equiperdum* (eESAG4c), which is homologous to the ESAG4 of *T. brucei*, has been shown to encode an adenylyl cyclase which will complement an adenylyl cyclase (cyr-1) deletion mutant of *S. cerevisiae* [Ross et al. (1991) EMBO J. 10, 2047–2053].

The eESAG4c ORF contains sequence with homology to both *S. cerevisiae* and *S. pombe* adenylyl cyclases [Kataoka et al. (1985) Cell, 43, 493–505; Yamawaki-Kataoka et al. (1989) PNAS 86, 5693–5697; Young et al. (1989) PNAS 86, 7989–7993]. The region that is conserved between trypanosomes and yeast is within the yeast adenylyl cyclase catalytic domain and exhibits a sequence identity on the order of 50%. The eESAG4c sequence is approximately 40% identical to that of bovine brain adenylyl cyclase type 1 (Krupinski et al. (1990) Science 244, 1558–1562). The protein predicted by the eESAG4c sequence bears an N-terminal sequence that encodes a putative transmembrane domain flanking the sequence that is homologous to the adenylyl cyclase catalytic domain.

Also identified within the ESAG of *Trypanosoma equiperdum* are sequences which bear homology to a "leucine-rich repeat" gene family (Takahashi et al. (1985) PNAS 82, 1906–1910; Lopez et al. (1988) PNAS 85, 2135–2139; Hashimoto et al. (1988) Cell 52, 269–279). Proteins encoded by members of this family are involved in diverse functions, however, the repeat sequences are believed to be involved in membrane association and in protein-protein interactions. In *S. cerevisiae* the repeat domain of adenylyl cyclase is required for regulation of the enzyme by RAS proteins and for the association of the enzyme with the plasma membrane [Colicelli et al. (1990) Mol. Cell. Biol. 10, 2539–2543; Field et al. (1990) Science 247, 464–467; Mitts et al. (1990) Mol. Cell. Biol. 10, 3873–3883.] Also within the ESAG are sequences with limited homology to nucleotide binding domains [Florent et al. (1991) Mol. Cell. Biol. 11, 2180–2188] that have been hypothesized to have a regulatory function in trypanosomes analogous to that of Ras in yeast. Neither the leucine-rich repeat region nor the nucleotide binding domain were included in the sequences that complemented the yeast cyr deletion mutants [Ross et al. (1991) EMBO J. 10, 2047–2053]. Ross et al. (1991) speculated that the lack of these potential regulatory sequences would account for the much greater adenylyl cyclase activity exhibited by cyr-1 deletion mutants expressing eESAGc than was seen in yeast expressing the endogenous CYR gene from plasmids.

In addition to ESAG4, cloned from the VSG region of *Trypanosoma brucei*, at least three other genes cloned from *T. brucei*, GRESAG 4.1, 4.2 and 4.3, bear sequence homology to eukaryotic adenylate and guanylate cyclases (Alexandre et al. (1990) Mol. Biochem. Parasitol. 43, 279–288). ["GRESAG" indicates Genes Related to Expression Site Associated Genes.] It has been demonstrated that both ESAG 4 and GRESAG 4.1 can complement a *S. cerevisiae* adenylyl cyclase deletion mutant, cyr1Δ. The trypanosome cyclases associate with the yeast membrane fraction, differ in their response to $Ca^{2+}$, and do not appear to be properly regulated in yeast [Paindavoine et al. (1992) Mol. Cell. Biol. 12, 1218–1225].

Thus, the heterogenous adenylyl cyclases that have been shown to exhibit activity, although unregulated, in yeast are derived from trypanosome species. The trypanosome cyclase genes lie in regions near sequences encoding leucine-rich motifs with homology to a regulatory domain of yeast adenylyl cyclase. This suggests that proteins which derive from the two different trypanosome sequences may interact to form a regulatory complex. This could be analogous to the situation in *Saccharomyces cerevisiae* where activity of adenylyl cyclase is controlled through the interaction of the enzyme with regulatory RAS proteins. The homologies of sequence and regulation between the yeast and trypanosome enzymes appear to have favored the complementation of yeast deleted for adenylyl cyclase with sequences encoding the trypanosome enzyme.

Attempts to Express Mammalian Adenylyl Cyclases in Yeast

Previous attempts by other laboratories to express mammalian adenylyl cyclase in yeast were unsuccessful. Ronald Taussig, working in the laboratory of Alfred Gilman at the University of Texas Southwestern Medical Center, attempted to express mammalian type 1 adenylyl cyclase in *Saccharomyces cerevisiae* (personal communication). The protocol used by Taussig involved rescue of cyc cells by transformation with mammalian type 1 adenylyl cyclase; the metric of cyclase activity was growth of the test cells on forskolin-containing medium. Forskolin is known to bind directly to and to stimulate adenylyl cyclase types 1–6 in mammalian cells. Taussig was unable to detect enzyme activity in cyc cells transformed with the mammalian enzyme, i.e., he was unable to detect growth of transformed cells on forskolin-containing medium.

Expression of Mammalian Adenylyl Cyclases in Dictyostelium Discoideum.

The mammalian type 2 cyclase has been functionally expressed, by means not publicly disclosed, in the primitive eukaryote Dictyostelium discoideum [personal communication from P. Devreotes cited in Iyengar (1993)]. The structure of one of the two adenylyl cyclase genes that have been isolated from Dictyostelium, ACA, is predicted to be structurally analogous to the mammalian cyclases in that it is also an integral membrane protein [Pitt et al. 1992]. In addition, Dictyostelium can express eight Gα subunits, each bearing approximately 45% sequence homology to mammalian Gα proteins [Hadwiger et al. 1991; Wu and Devreotes 1991]. The lack of success in Gilman's laboratory at expressing a functional mammalian type 1 adenylyl cyclase in yeast, and the successful expression of the mammalian enzyme in Dictyostelium, indicate that differences in the transduction of signal to this enzyme exist between yeast and the higher eukaryotes. Furthermore, those differences must be taken into consideration in any attempt to recapitulate a signal transduction pathway with mammalian adenylyl cyclase in yeast.

Peptide Libraries

Peptide libraries are systems which simultaneously display, in a form which permits interaction with a target, a highly diverse and numerous collection of peptides. These peptides may be presented in solution (Houghten 1991), or on beads (Lam 1991), chips (Fodor 1991), bacteria (Ladner U.S. Pat. No. 5,223,409), spores (Ladner U.S. Pat. No. '409), plasmids (Cull 1992) or on phage (Scott, Devlin, Cwirla, Felici, Ladner '409). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

Ladner, U.S. Pat. No. 5,096,815 describes a method of identifying novel proteins or polypeptides with a desired DNA binding activity. Semi-random ("variegated") DNA encoding a large number of different potential binding proteins is introduced, in expressible form, into suitable host cells. The target DNA sequence is incorporated into a genetically engineered operon such that the binding of the protein or polypeptide will prevent expression of a gene product that is deleterious to the cell under selective conditions. Cells which survive the selective conditions are thus cells which express a protein which binds the target DNA. While it is taught that yeast cells may be used for testing, bacterial cells are preferred. The interactions between the protein and the target DNA occur only in the cell, not in the periplasm, and the target is a nucleic acid, not a protein.

Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., J. Biol. Chem. 264, 20206 (1989) and Kaiser et al. Science 235, 312 (1987), respectively).

Yeast have been engineered to express foreign polypeptide variants to be tested as potential antagonists of mammalian receptors. Libraries encoding mutant glucagon molecules were generated through random misincorporation of nucleotides during synthesis of oligonucleotides containing the coding sequence of mammalian glucagon. These libraries were expressed in yeast and culture broths from transformed cells were used in testing for. antagonist activity on glucagon receptors present in rat hepatocyte membranes (Smith et al. 1993).

All references cited in this specification are hereby incorporated by reference. No admission is made that any reference constitutes prior art.

SUMMARY OF THE INVENTION

The present invention relates to the functional expression of a mammalian adenylyl cyclase in yeast, and to the use of the engineered yeast cells in identifying not only potential inhibitors or activators of the mammalian adenylyl cyclase, but also of other proteins which are naturally or artificially "coupled to the mammalian adenylyl cyclase in the engineered yeast cell. The term "coupled" here means that inhibition or inactivation of the coupled protein results in inhibition or activation (not necessarily respectively) of the adenylyl cyclase. Functional expression of human adenylyl cyclases is especially desirable.

The adenylyl cyclase of Saccharomyces cerevisiae is a peripheral membrane protein with a structure that is substantially different from that of the cloned mammalian adenylyl cyclases; all six mammalian adenylyl cyclase cDNAs cloned to date encode integral membrane proteins with intricate transmembrane structures forming a significant part of their overall structure. Furthermore, although yeast contain heterotrimeric G proteins, these proteins do not appear to be involved in the regulation of S. cerevisiae adenylyl cyclase, rather, the yeast enzyme is regulated by other members of the family of GTP-binding proteins, Ras1 and Ras2. The yeast adenylyl cyclase thus bears scant resemblance to the mammalian enzyme in structure and in regulation and it could not have been assumed that the mammalian enzyme could be made to function in Saccharomyces.

However, these incompatibilities were overcome through co-expression in yeast of a mammalian adenylyl cyclase and the mammalian G protein subunit, Gαs. This was accomplished by genetically engineering a suitable yeast strain. We had no a priori reason to expect that the presence of wild type Gαs alone would be sufficient to activate the mammalian adenylyl cyclase. We had worked under the assumption that it would also be necessary to express a mammalian seven transmembrane receptor, stimulation of which could in turn activate Gαs and, then, the cyclase. Our result was, therefore, an unexpected discovery.

Without being bound to any theory, it is presently believed that GTP produced by the yeast cell binds to the mammalian Gαs, which then in turn activates the mammalian adenylyl cyclase. This enzyme converts ATP to cyclic AMP, which is required for yeast cell growth. Therefore, if the yeast's native adenylyl cyclase is inactive, its growth is dependent on the functional expression of the mammalian adenylyl cyclase.

Preferably, the yeast cell is a diploid strain, or another strain which does not express yeast Gα, Gβ or Gγ.

The engineered yeast cells may be used to detect inhibitors or activators of the mammalian adenylyl cyclase. If desired, another exogenous protein may be coupled to the mammalian adenylyl cyclase, so that inhibitors or activators of the other exogenous protein may be detected by virtue of their effect on adenylyl cyclase activity. In a preferred embodiment, the other exogenous protein is a surrogate for a pheromone system protein, as hereafter defined. In an especially preferred embodiment, the other exogenous protein is a mammalian G protein-coupled receptor, which is a surrogate for the yeast pheromone receptor.

In a preferred embodiment, the screened inhibitors and activators are peptides co-expressed in the engineered yeast cells. In an especially preferred embodiment, the yeast cells of the culture collectively express a peptide library to be screened for modulatory activity.

The appended claims are to be treated as a non-limiting recitation of preferred embodiments.

BRIEF DESCRIPTION OF THE DRAWINGS

FIG. 1. Structural model of mammalian adenylyl cyclase This figure reproduces the model of mammalian adenylyl cyclase described in Tang et al. (1992) C. S. H. Symposia on Quantitative Biology 57, 135–144. $M_1$ and $M_2$ denote two domains, each containing six putative membrane-spanning sequences. $N_1$ and $N_2$ together comprise the short amino terminal tail which is believed to reside intracellularly. N2 sequences are those proximal to the first transmembrane sequence. $C_{1a}$ and $C_{1b}$ form a large cytoplasmic loop that joins the two transmembrane domains. The $C_{2a}$ and $C_{2b}$ sequences form a second large cytoplasmic loop. The C-terminal sequence denoted $C_{2b}$ is present only in type 1 and type 3 adenylyl cyclases.

As shown in FIG. 2a Stage 1 (lower portion of FIG. 2a) involves the development of yeast strains in which SST2, FAR1, and HIS3 are inactivated and a suitable reporter construct like fus1::HIS3 is integrated into the genomes of both α and a cells. α cells are further altered by replacement of the normally expressed STE3p with STE2p, while a cells are further modified by replacement of the normally expressed STE2p with STE3p. The resulting strains should show growth on histidine-deficient media in the absence of exogenous pheromone.

As shown in FIG. 2b Stage 2 (upper portion of FIG. 2b) involves, first, inactivation of MFα1 and MFα2 in cells and inactivation of MFa1 and MFa2 in a cells developed in Stage 1. These modifications will result in strains which are auxotrophic for histidine. Next, the appropriate expression plasmid will be introduced: the expression plasmid pADC-MF containing an oligonucleotide encoding α-factor should confer upon α cells the ability to grow on histidine-deficient media; the expression plasmid pADC-MFa containing an oligonucleotide encoding a-factor should enable a cells to grow on histidine-deficient media.

Figure 2A:
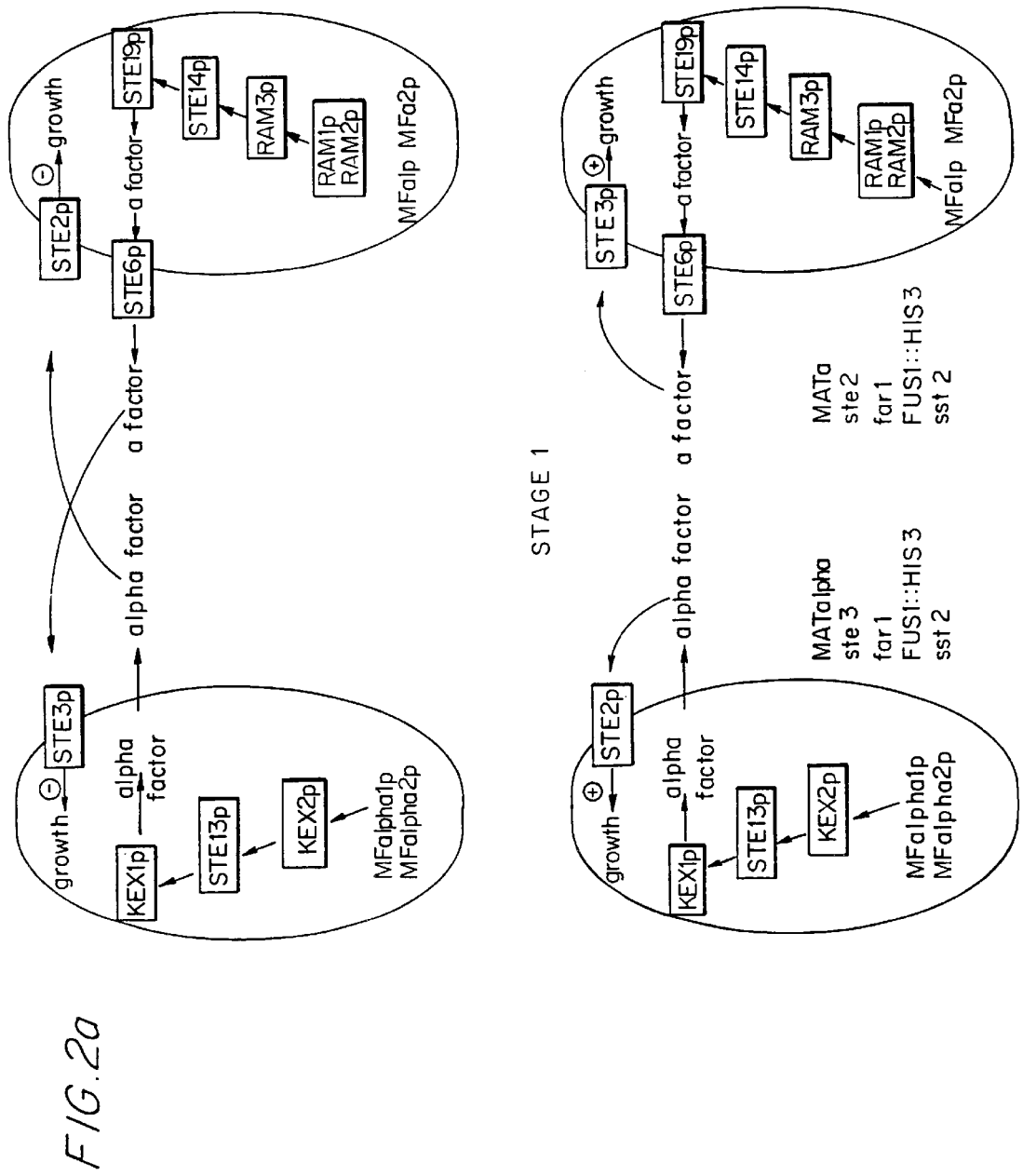
FIGS. 2a and 2b. Outline of successive stages in the development of yeast autocrine systems An outline of the normal synthesis and release of mating pheromones is diagrammed in the upper portion of FIG. 2a. Two genes, MFα1 and MFα2, encode precursor proteins (MFα1p and MFα2p) containing four and two repeats, respectively, of the tridecapeptide representing mature α-factor. These precursors are processed proteolytically in a series of enzymatic reactions that begin with cleavage of the signal sequence in the endoplasmic reticulum and involve both glycosylation of the leader peptide and cleavage by the proteases KEX2p, STE13p, and KEX1P. The result is the secretion of mature α-factor which, upon binding to STE2p normally expressed on the surface of a cells, elicits a number of changes in the a cells, including growth arrest. The a cells, in turn, express two genes, MFa1 and MFa2, which encode precursors (MFa1p and MFa2p) for a-factor. These precursors undergo farnesylation by RAM1 and RAM2, proteolytic trimming of the C-terminal three amino acids (by a protein tentatively identified as RAM3p), carboxymethylation of the newly exposed C-terminal cysteine by STE14p, and endoproteolytic removal of the N-terminal leader sequence by an activity provisionally identified as STE19p. Upon export of the mature a-factor from the cell via STE6p, it binds to STE3p expressed on the surface of α cells and stops their growth.
Figure 2B:
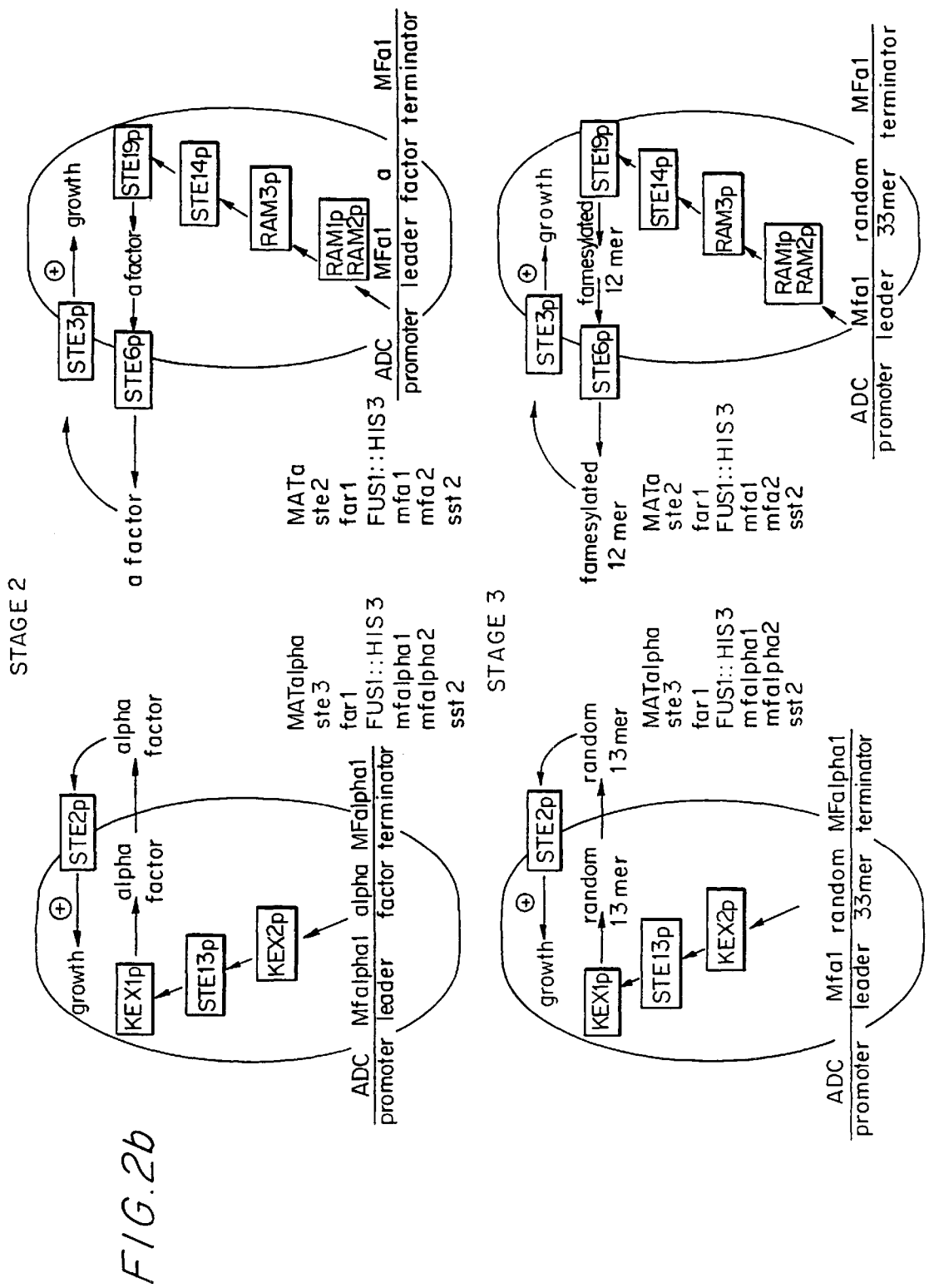

Stage 3 (lower portion of FIG. 2b) uses the cells developed in Stage 2 for the insertion of expression plasmids. However, instead of using plasmids which contain oligonucleotides that encode genuine pheromone, the yeast will be transformed with expression plasmids that contain random or semi-random oligonucleotides. Transformants which can grow on histidine-deficient media will be expanded and their plasmids isolated for sequencing of the inserted oligonucleotide.

DETAILED DESCRIPTION OF THE PREFERRED EMBODIMENTS OF THE INVENTION

1. General Considerations 1.1 Definitions

For the purpose of the present invention, an "exogenous" protein is one which sufficiently differs in amino acid sequence from the proteins naturally produced by the yeast cell in question so that its closest cognate is a protein produced by a cell other than a yeast cell. The cell producing this cognate protein may be a microbial cell (other than a yeast cell), a plant cell, or an animal cell. If an animal cell, it may be of invertebrate (e.g., insect or nematode) or of vertebrate (e.g., avian, piscine or mammalian, especially human) origin. A protein is considered to be of, e.g., human origin, regardless of whether it is encoded by the chromosome of a normal human, or by the genome of a virus which infects and replicates in human cells.

A yeast protein which is involved in the post-translational modification, transport, recognition or signal transduction of a yeast pheromone will be referred to as a "pheromone system protein" (PSP), and cognate non-yeast proteins which are capable of substituting for a PSP sufficiently, to be able, at least under some circumstances, to carry out that role of the yeast protein in the engineered yeast cell as PSP surrogates.

An "activator" of an adenylyl cyclase is a substance which, in a suitable yeast cell, causes the adenylyl cyclase to become more active, and thereby elevates the cAMP signal of said cell to a detectable degree. The mode of action of the activator may be direct, e.g., through binding the cyclase, or indirect, e.g., through binding another molecule which otherwise interacts with the cyclase.

Conversely, an "inhibitor" of an adenylyl cyclase is a substance which, in a suitable yeast cell, causes the cyclase to become less active, and thereby reduces the cAMP signal to a detectable degree. The reduction may be complete or partial, and due to a direct or an indirect effect.

An "activator" of a pheromone system protein surrogate is a substance which, in a suitable yeast cell, causes the pheromone system protein surrogate to become more active, and thereby elevates the signal transduced by the native or modified pheromone signal pathway of said cell to a detectable degree. The surrogate may be initially nonfunctional, but rendered functional as a result of the action of the activator, or it may be functional, and the effect of the activator is to heighten the activity of the surrogate. The mode of action of the activator may be direct, e.g., through binding the surrogate, or indirect, e.g., through binding another molecule which otherwise interacts with the surrogate. When the PSP surrogate is a substitute for a pheromone receptor, and the activator takes the place of the pheromone, it is customary to refer to the activator as an agonist of the receptor.

Conversely, an "inhibitor" of a pheromone system protein surrogate is a substance which, in a suitable yeast cell, causes the PSP surrogate to become less active, and thereby reduces the transduced signal to a detectable degree. The reduction may be complete or partial. When the PSP surrogate is a substitute for a pheromone receptor, and the inhibitor competes with the pheromone for binding to the receptor, it is customary to refer to the inhibitor as an "antagonist".

The term "modulator" includes both "activators" and "inhibitors".

A "mammalian adenylyl cyclase" is a protein which is either identical to an adenylyl cyclase occurring naturally in a mammal, or is a mutant which is substantially homologous with such a mammalian adenylyl cyclase and more similar in sequence to it than to the yeast adenylyl cyclase. Related terms, such as "primate adenylyl cyclase", or "human adenylyl cyclase", are analogously defined. A mammalian adenylyl cyclase is "functionally homologous" to a yeast protein if, either alone, or in concert with other exogenous proteins, or after being modified by a drug, it is able to provide an adenylyl cyclase activity within the engineered yeast cell. It is not necessary that it be as efficient as the yeast protein, however, it is desirable that it have at least 10% of the activity of the cognate yeast protein.

A surrogate PSP protein is "functionally homologous" to a yeast protein if, either alone or after being modified by a drug, it is able to perform the function of the yeast PSP, or an analogous function, within the engineered yeast cell. It is not necessary that it be as efficient as the yeast protein, however, it is desirable that it have at least 10% of at least one of the pheromone system-related activities of the yeast protein. Nor is it necessary that it have the same spectrum of action as the yeast protein, e.g., if it is a receptor, it may respond to entirely different ligands than does the endogenous receptor, or to some common ligands and some new ones. The receptors of Table 2 are considered functionally homologous with the yeast pheromone receptors, even though they do not respond to yeast pheromones, and may not couple to the unmodified endogenous G proteins, although they are G protein-coupled receptors. This is considered an "analogous function".

The PSP surrogate may be a protein which must be modified in some way by a drug to be functional. For example, the drug could cause an allosteric change in the PSP surrogate's conformation, or it could cleave off a portion of the surrogate, the balance of the protein then being a functional molecule.

The PSP surrogate may also be one which is functional only if other modifications are made in the yeast cell, e.g., expression of a chimeric G α subunit to interact with an exogenous G protein-coupled receptor.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" amino acid sequences are at least 50%, more preferably at least 80%, identical in sequence, at least over any regions known to be involved in the desired activity, when sequences are aligned by art-accepted methods. The sequence alignment tool that we use is part of the sequence analysis software package, Version 7.3, from GCG (Genetics Computer Group, 575 Science Drive, Madison, Wis. 53711). BESTFIT uses the homology algorithm of Smith and Waterman [Advances in Applied Mathematics 2, 482–489 (1981) ] to identify the best alignment of two sequences. We would initially set parameters for the following:
Match=1.0 Gap weight=1.0 Mismatch=−0.9 Length weight= 0.0 selecting neither the "LOWroad" nor "HIGHroad" options.

Most preferably, no more than five residues, other than at the termini, are different. Preferably, the divergence in sequence, at least in the aforementioned regions, is in the form of "conservative modifications".

"Conservative modifications" are defined as
(a) conservative substitutions of amino acids as hereafter defined; and
(b) single or multiple insertions or deletions of amino acids at the termini, at interdomain boundaries, in loops or in other segments of relatively high mobility.

Preferably, except at the termini, no more than about five amino acids are inserted or deleted at a particular locus, and the modifications are outside regions known to contain binding sites important to activity.

Conservative substitutions are herein defined as exchanges within one of the following five groups:
I. Small aliphatic, nonpolar or slightly polar residues: Ala, Ser, Thr (Pro, Gly)
II. Polar, negatively charged residues, and their amides Asp, Asn, Glu, Gln
III. Polar, positively charged residues: His, Arg, Lys
IV. Large, aliphatic, nonpolar residues: Met, Leu, Ile, Val (Cys)
V. Large, aromatic residues: Phe, Tyr, Trp Residues Pro, Gly and Cys are parenthesized because they have special conformational roles. Cys participates in formation of disulfide bonds. Gly imparts flexibility to the chain. Pro imparts rigidity to the chain and disrupts a helices. These residues may be essential in certain regions of the polypeptide, but substitutable elsewhere.

"Semi-conservative substitutions" are defined herein as being substitutions within supergroup II/III/III or within supergroup IV/V, but not within a single one of groups I–V. If a substitution is not conservative, it preferably is semi-conservative.

Two regulatory DNA sequences (e.g., promoters) are "substantially homologous" if they have substantially the same regulatory effect as a result of a substantial identity in nucleotide sequence. Typically, "substantially homologous" sequences are at least 50%, more preferably at least 80%, identical, at least in regions known to be involved in the desired regulation. Most preferably, no more than five bases are different.

"Inactivation" means that production of a functional gene product is prevented or inhibited. Inactivation may be achieved by deletion of the gene, mutation of the promoter so that expression does not occur, mutation of the coding sequence so that the gene product is inactive, or failure to provide factors necessary for the biological activity of the gene product. Inactivation may be partial or total. "Functional expression" refers to expression of a gene under conditions such that its gene product is not only expressed but is also biologically active within the expressing cell.

The term "autocrine cell", as used herein, refers to a cell which produces a substance which can stimulate a signal transduction pathway of that cell. Wild-type α and a cells are not autocrine with respect to the pheromone pathway. However a yeast cell which produces both α-factor and α-factor receptor, or both a-factor and a-factor receptor, in functional form, is so autocrine. By extension, yeast cells which produce a peptide which is being screened for the ability to activate a G protein-coupled receptor, a surrogate for the yeast pheromone receptor, are called "autocrine cells", though it might be more precise to call them "putative autocrine cells". Of course, in a library of such cells, in which a multitude of different peptides are produced, it is likely that one or more of the cells will be "autocrine" in the stricter sense of the term.

1.2 Design of Chimeric Proteins

If a mammalian or other exogenous protein, unmodified, cannot be functionally expressed, to the extent desired, in a yeast cell, one may engineer the yeast cell to express a protein which is a chimera of the exogenous protein of interest and a cognate yeast protein. The term "chimera" implies that one portion of the sequence is more homologous to the yeast protein than to the (say) mammalian protein, and another portion is the reverse. Possible combinations include mammalian/yeast, yeast/mammalian, mammalian/yeast/mammalian, and yeast/mammalian/yeast.

Functional chimeras may be identified by a systematic synthesize-and-test strategy. It is not necessary that all theoretically conceivable chimeras be evaluated directly.

One strategy is described schematically below. We divide the aligned protein sequences into two or more testable units. These units may be equal or unequal in length. Preferably, the units correspond to functional domains or are demarcated so as to correspond to special features of the sequence, e.g., regions of unusually high divergence or similarity, conserved or unconserved regions in the relevant protein family or the presence of a sequence motif, or an area of unusual hydrophilicity or hydrophobicity. Let "Y" represent a unit of the yeast protein, and "M" a corresponding unit of a mammalian protein. If there are five units (the choice of five instead of two, three, four, six, ten, etc. is arbitrary), we can synthesize and test any or all of the following chimeras, which will help us rapidly localize the critical regions:

(a) progressive C-terminal substitution of mammalian sequence for yeast sequence, e.g.,

```
Y Y Y Y Y
Y Y Y Y M
Y Y Y M M
Y Y M M M
Y M M M M
M M M M M
```

(b) progressive N-terminal substitution of mammalian sequence for yeast sequence

```
Y Y Y Y Y
M Y Y Y Y
M M Y Y Y
M M M Y Y
M M M M Y
M M M M M
```

(c) dual terminal substitutions, e.g.,

```
M M M M M
Y M M M Y
Y Y M Y Y
Y Y Y Y Y
and
Y Y Y Y Y
M Y Y Y M
M M Y M M
M M M M M,
```

(d) single replacement "scans," such as

```
M Y Y Y Y
Y M Y Y Y
Y Y M Y Y
Y Y Y M Y
Y Y Y Y M
and
Y M M M M
M Y M M M
M M Y M M
M M M Y M
M M M M Y
```

Based on the data these tests provide, it may appear that, e.g., the key difference between the yeast and mammalian sequences vis-a-vis, say, display on the yeast membrane, is in the fifth unit. One can then subdivide that unit into subunits and test further, e.g.

```
M M M M (mm)
M M M M (my)
M M M M (ym)
M M M M (yy)
``` where the parenthesis refer to two subunits into which the fifth unit was subdivided.

1.3 Design of Functional Mutants Generally

A protein is more likely to tolerate a mutation which (a) is a substitution rather than an insertion or deletion;

(b) an insertion or deletion at the terminus, than internally;

(c) affects a surface residue rather than an interior residue;

(d) affects a part of the molecule distal to the binding site;

(e) is a substitution of one amino acid for another of similar size, charge, and/or hydrophobicity; and (f) is at a site which is subject to substantial variation among a family of homologous proteins to which the protein of interest belongs.

These considerations can be used to design functional mutants.

Surface vs. Interior Residues

Charged residues almost always lie on the surface of the protein. For uncharged residues, there is less certainty, but in general, hydrophilic residues are partitioned to the surface and hydrophobic residues to the interior. Of course, for a membrane protein, the membrane-spanning segments are likely to be rich in hydrophobic residues.

Surface residues may be identified experimentally by various labeling techniques, or by 3-D structure mapping techniques like X-ray diffraction and NMR. A 3-D model of a homologous protein can be helpful.

Binding Site Residues

Residues forming the binding site may be identified by (1) comparing the effects of labeling the surface residues before and after complexing the protein to its target, (2) labeling the binding site directly with affinity ligands, (3) fragmenting the protein and testing the fragments for binding activity, and (4) systematic mutagenesis (e.g., alanine-scanning mutagenesis) to determine which mutants destroy binding. If the binding site of a homologous protein is known, the binding site may be postulated by analogy.

Protein libraries may be constructed and screened that a large family (e.g., $10^8$) of related mutants may be evaluated simultaneously.

2. Mammalian Adenylyl Cyclases 2.1 Overview

The signals transduced through the heterotrimeric G proteins in mammalian cells influence intracellular events through the action of molecules termed effectors. Among the best characterized of these effector molecules is the hormone-responsive enzyme, adenylyl cyclase. As of early 1994, six full-length and two partial cDNA clones of adenylyl cyclase have been obtained from a variety of mammalian tissues. Sequence analysis of the encoded proteins resulted in the identification of eight enzyme types, while functional characteristics have determined their grouping into five distinct families (Iyengar (1993) FASEB J. 7, 768–775). The first family is comprised of type 1 adenylyl cyclase; this enzyme is stimulated by hormone receptors through Gαs, by forskolin and by $Ca^{2+}$/calmodulin. A cDNA encoding type 1 was isolated from a bovine brain library [Krupinski et al. (1989) Science 244, 1558–1564]. The activity of the type 1 enzyme is inhibited by the expression of Gβγ subunits. Each of the other cloned mammalian cyclases which have been expressed in cells are also stimulated by Gαs and by forskolin. However, it has been shown that responses to Gβγ and to $Ca^{2+}$/calmodulin vary among those other enzymes.

A second family is comprised of type 2 and type 4 adenylyl cyclases; these enzymes are stimulated by Gβγ, but that stimulation depends on the presence of activated Gαs. Enzymes belonging to this second family have been cloned from rat brain [Feinstein et al. (1991) PNAS 88, 10173–77] and testes [Gao and Gilman (1991) PNAS, 88 10178–10182]. This family of adenylyl cyclases is insensitive to $Ca^{2+}$/calmodulin. Although related by sequence homology, type 2 and type 4 adenylyl cyclase differ in both distribution and regulation. Type 2 message is found only in brain and lung tissue, while type 4 is more widely expressed, having been detected in brain, kidney, liver, heart, lung and testis. The type 2 enzyme and all other mammalian adenylyl cyclases cloned to date, except type 4, contain potential sites for phosphorylation by protein kinase A. Furthermore, the type 2 enzyme is known to be substantially stimulated by activated protein kinase C, while type 4 adenylyl cyclase is unaffected by that kinase.

Type 3 adenylyl cyclase, cloned from rat olfactory tissue [Bakalyar and Reed (1990) Science 250, 1403–1406] is abundantly expressed in olfactory neuroepithelia, is sensitive to stimulation by $Ca^{2+}$/calmodulin, but is not affected directly by the presence of Gβγ. The type 3 enzyme may be central to olfactory signal transduction.

A fourth family of adenylyl cyclases has been cloned from a variety of sources including canine heart [Ishikawa et al. (1992) J. Biol. Chem. 267, 13553–13557], rat liver and kidney [Premont et al. (1992) PNAS 89, 9808–9813], mouse lymphoma cells [Premont et al. (1992) Endocrinology 131, 2774–2783] and from a mouse/hamster hybrid cell line NCB-20 [Yoshimura and Cooper (1992) PNAS 89, 6716–6720]. These enzymes are termed types 5 and 6 on the basis of sequence, are unaffected by Gβγ in the presence or absence of activated Gαs, and are inhibited by low concentrations of $Ca^{2+}$. Multiple messages for types 5 and 6 have been observed, suggesting that alternatively spliced forms occur. The type 6 enzyme has been shown to exist in long and short forms which differ in the presence or absence of a 14 amino acid stretch at the N-terminus (Iyengar (1993) FASEB J. 7,768–775). Types 5 and 6 show significant overall sequence similarity, including >50% homology in the putative transmembrane regions where the greatest degree of sequence divergence exists among adenylyl cyclase subtypes (Katsushika et al. (1992) Proc. Natl. Acad. Sci. USA 89, 8774–8778). Like type 5, type 6 expression is highest in heart and brain; unlike type 5, type 6 mRNA is also detected in a variety of other tissues.

Type 7 adenylyl cyclase, cloned as a partial cDNA from the S49 mouse lymphoma cell line [Krupinski et al. (1992) J. Biol. Chem. 267, 24858–258621], appears to be related to the type 2 enzyme. A second partial clone, termed type 8 adenylyl cyclase, was obtained from a human brain library, and encodes a protein that is distinct from previously characterized enzymes [Parma et al. (1991) Biochem. Biophys. Res. Comm. 179, 455–462] and may be brain-specific [Krupinski et al. (1992) J. Biol. Chem. 267, 24858–25862).

The majority of mammalian adenylyl cyclases are integral membrane proteins. Sequence analysis of the cloned enzymes predicts the presence of twelve membrane-spanning regions present in two domains which each contain six hydrophobic sequences. The short N- and the lengthy C-terminal sequences are predicted to reside intracellularly. Overall sequence similarity among the various adenylyl cyclase types is approximately 50%, with greater homologies between some isolates resulting in their categorization in subfamilies. There exist two large cytoplasmic domains, a 350 amino acid loop between the first and second set of six transmembrane sequences (C1) and an extensive C-terminal tail (250–300 amino acids) following the second set of six transmembrane sequences (C2). Portions of these cytoplasmic domains bear sequence similarity to the catalytic domains that have been identified in cloned guanylyl cyclases (Chinkers and Garbers (1991) Ann. Rev. Biochem. 60, 553–575], are to some degree homologous with one another (60–80% homology between the C1 and C2 domains), and are highly conserved in the mammalian adenylyl cyclases that have been sequenced to date (50–92%) [Iyengar (1993) FASEB J. 7,768–775; Koesling et al. (1991) FASEB J. 5, 2785–2791; Tang and Gilman (1992) Cell 70, 869–872]. In contrast, the transmembrane regions of the various adenylyl cyclases lack significant sequence homology to one another.

Aside from the sequence homology to the catalytic domains of the guanylyl cyclases, analysis of the Drosophila homolog of the bovine type I adenylyl cyclase yields additional evidence that the C-terminal tail of the mammalian enzyme contributes to catalysis. A point mutation (Gly to Arg) in the C-terminal cytoplasmic domain of the Drosophila enzyme results in the loss of adenylyl cyclase activity. This mutation alters a glycine residue that is absolutely conserved in all mammalian adenylyl cyclase isolates (Levin et al. (1992) Cell 68, 479–489). Point mutations in the conserved domains of C1 and C2 result in decreased catalytic activity of the mammalian enzyme (Tang et al. 1992 Cold Spring Harbor Symp. Quant. Biol. 57, 135–144). In addition, truncated forms of adenylyl cyclase that lack either the central cytoplasmic loop or the C-terminal tail sequence are devoid of enzyme activity. Thus, expression of either half of the molecule yields inactive enzyme while co-expression of both halves partially restores catalytic activity (Tang et al. (1991) J. Biol. Chem. 266, 8595–8603). Since co-expression of the two halves of the molecule does not restore activity in full, it has been hypothesized that the transmembrane domains of the enzyme direct optimal interaction between the two large cytoplasmic regions of the protein and, thus, the stable formation of an active site (Iyengar (1993) FASEB J. 7, 768–775). Soluble forms of guanylyl cyclase are known to function as heterodimers with each subunit contributing sequence that bears homology to the highly conserved C1 and C2 regions of adenylyl cyclase (Nakane et al. 1990 J. Biol. Chem. 265, 479–489).

Aside from a proposed role of active site stabilization, the contribution of the transmembrane domains to adenylyl cyclase function remains enigmatic. The hydrophobic domains appear to be the site for forskolin action. Forskolin is a lipid-soluble diterpene that specifically binds to and activates adenylyl cyclase in mammalian cells in the absence of G protein-coupled receptor agonists. Forskolin has no effect on the testis-specific cyclase of mammals or on bacterial cyclases; these proteins are cytosolic. However, the ACA cyclase of Dictyostelium, an integral membrane protein, is insensitive to forskolin whereas mammalian type 2 cyclase, when it is expressed in Dictyostelium, is sensitive to stimulation by the diterpene (personal communication from P. Devreotes cited in Iyengar (1993) FASEB J. 7,768–775).

Preferably, the yeast cell is engineered to express a type 1, 2, 3, 4, 5, 6, 7 or 8 mammalian adenylyl cyclase. Cyclases of type 2 are especially preferred. Within the aforementioned types, the following cyclases are of particular interest:

| Adenylyl Cyclase Type | Characteristics |
| --- | --- |
| Type 1 (I) | brain specific |
| | directly inhibited by G$\beta\gamma$ |
| Type 2 (II) | stimulated directly by G$\beta\gamma$ in the presence of G$\alpha$s |
| | stimulated by protein kinase C |
| Type 3 (III) | from olfactory tissue |
| | sensitive to Ca/Calmodulin |
| | but insensitive to G$\beta\gamma$ |
| Type 4 (IV) | stimulated directly by G$\beta\gamma$ in the presence of G$\alpha$s |
| | member of Type 2 family |
| Type 5 (V) | mRNA found at high level in brain and heart |
| | not directly affected by G$\beta\gamma$ |
| Type 6 (VI) | mRNA found at high level in brain and heart |
| | not directly affected by G$\beta\gamma$ |
| | member of Type 5 family |
| Type 7 (VII) | member of Type 2 family |

As many as 10 distinct isoforms of mammalian adenylyl cyclase from several species have been cloned. Types I through VIII have been sequenced and reported in the literature. The cloning and sequencing of types IX and X have not been published, although the sequence of type X was presented at a Gordon Conference in February 1995. Those isoforms whose sequence has been published are: bovine type I (Krupinski, J., et al, Science 244: 1558–1564, 1989); human type II (Stengel, D., et al, Hum Genet 90: 126–130, 1992); rat type II (Feinstein, P G et al, Proc Natl Acad Sci USA 88: 10173–10177, 1991); rat type III (Bakalyar, H A, and Reed, R R, Science 250: 1403–1406, 1990); rat type IV (Gao, B. and Gilman, A. G., Proc Natl Acad Sci USA 88: 10178–10182, 1991); canine type V (Ishikawa, Y. et al, J Biol Chem 267: 13553–13557, 1993); rabbit type V (Wallach, J. et al, FEBS Lett 338: 257–263, 1994); canine type VI (Katsushika, S. et al, Proc Natl Acad Sci USA 89: 8774–8778, 1992); murine type VI (Yoshimura, M., and Cooper, D. M., Proc Natl Acad Sci USA 89: 6716–6720, 1992); rat type VI (Premont, R. T. et al, Proc Natl Acad Sci USA 89: 9808–9813, 1992); murine type VII (Watson, P. A. et al, J Biol Chem 269: 28893–28898, 1994); human type VIII (Defer, N., et al FEBS Lett., 351: 109–113, 1994); rat type VIII (Cali, J. J. et al, J Biol Chem 269: 12190–5, 1994).

Detailed information is available regarding the regulation of several of the different isoforms. While the isoforms published to date differ in their control by G$\alpha$i subunits, G$\beta\gamma$ subunits, calcium, and protein kinase C, all are activated by G$\alpha$s (Taussig et al, J Biol Chem 269: 6093–6100, 1994; Chen, J., and Iyengar, R., J Biol Chem 268: 12253–12256, 1993; Cooper et al, Nature 374: 421–424, 1995). The present invention can be used to provide these adenylyl cyclases as functional and regulatable activities in yeast.

The present invention is not limited to expression of the presently known mammalian adenylyl cyclases, or presently known types of such cyclases.

The cyclase is preferably a primate, especially a human cyclase, but may also be a cyclase associated with mammals of the orders Rodenta (mice, rats, rabbits, etc.), Arteriodactyla (goats, pigs, sheep, cows, etc.) or Carnivora (cats, dogs, etc.), or other mammalian orders.

The mammalian adenylyl cyclase of the present invention need not be a naturally occurring protein, rather, it may be a mutant, provided that its sequence is more similar to that of a naturally occurring mammalian adenylyl cyclase than to that of the naturally occurring yeast adenylyl cyclase encoded by CYRI. Preferably, the mutant is also substantially homologous to a naturally occurring mammalian adenylyl cyclase, or a mutant known to be functional.

The *S. cerevisiae* gene that encodes adenylyl cyclase, CYR1, was cloned by Kataoka et al. ((1985) Cell, 43, 493–505). CYR1 encodes a protein consisting of 2026 amino acids; four domains of the protein have been identified and include the N-terminal and C-terminal domains as well as a central, repetitive amphipathic sequence and a catalytic domain. The central repetitive sequence bears homology to a 23 amino acid leucine-rich motif that is found repeated in a family of proteins identified in yeast, mammals and *Drosophila melanogaster* (Field et al. (1990) Science 247, 464–467). The leucine rich regions and the carboxyl terminus of the enzyme are required for its interaction with RAS proteins. The catalytic domain of yeast adenylyl cyclase has been localized to the C-terminal 417 amino acids [Kataoka et al. (1985) Cell, 43, 493–505]. Yeast adenylyl cyclase appears to be a peripheral membrane protein; it is found in the insoluble cell fraction after non-detergent extraction of cells. Hydropathic analysis of the sequence does not reveal a hydrophobic, membrane-spanning domain and the coding sequence lacks a signal sequence normally found in secreted or integral membrane proteins (Liao and Thorner (1980) PNAS, 77, 1898–1902; Kataoka et al. (1985) Cell, 43, 493–505; Perlman and Halvorson (1983) J. Mol. Biol. 167, 391–409). However, it is postulated that the repetitive domain which contains amphipathic sequence would permit embedding of the protein into membranes. In support of this hypothesis, truncated yeast adenylyl cyclase molecules that contain the central amphipathic sequence localize to membrane fractions when expressed in *E. coli* [Kataoka et al. (1985) Cell 43, 493–505].

Two ras genes in *S. cerevisiae* were originally identified by virtue of sequence homology with probes derived from mammalian ras genes (Broach and Deschennes (1990) Adv. Cancer Res. 54, 79–139). The Ras 1 and Ras 2 proteins of *S. cerevisiae* are required for vegetative growth of haploid cells through RAS-dependent activation of adenylyl cyclase and the synthesis of cAMP [Toda et al. (1985) Cell 40, 27–36; Broek et al. (1985) Cell 41, 763–769]. It is not known if RAS has any additional essential functions in yeast, however, overexpression of adenylyl cyclase in yeast can suppress the lethality that results from the loss of RAS function in ras 1 and ras 2 disruption mutants. Therefore, any additional essential functions of RAS are compensated for by increased production of cAMP (Kataoka et al. (1985) Cell, 43, 493–505).

Mutant proteins which are "substantially homologous" to a naturally occurring adenylyl cyclase may also be of value. In rat type II adenylyl cyclase, possible "neutral" mutations include substitutions in the non-conserved second membrane-spanning sequence in the first transmembrane domain (Leu78Ile;Ile79Leu; Ile93Leu and Leu94Ile). Substitutions that may be made in residues of the non-conserved fifth membrane-spanning sequence in the first transmembrane domain (Ile162Leu; Leu163Ile) could also yield a mutant protein with wild-type activity. It is probable that other conservative amino acid substitutions not specifically cited here may be made in the adenylyl cyclase sequence without any diminishment of wild type protein activity.

2.2 Use of the Adenylyl Cyclase in Screening

In its natural state, the mammalian adenylyl cyclase is inactive. However, it can be activated by other molecules, in particular, the free G$\alpha$ subunit or the G$\beta\gamma$ complex.

In one embodiment, the engineered cell is used to screen for drugs which, like G$\alpha$ or in some cases G$\beta\gamma$, can directly activate the adenylyl cyclase, or increase the activity of a partially activated adenylyl cyclase.

In a second embodiment, the engineered cell is used to screen for drugs which inhibit mammalian adenylyl cyclase. In this situation, the adenylyl cyclase must first be activated. This can be done by engineering the cell to overexpress G$\alpha$ or G$\beta\gamma$, as appropriate. Alternatively, the cell may be engineered to co-express both a G protein and a G protein coupled receptor, or any other protein which affects the activity of the adenylyl cyclase, e.g. calmodulin, PKA or PKC or any as yet unknown or uncharacterized proteins which directly bind interact with the adenylyl cyclase to affect its function, and the receptor stimulated either by externally added ligand or by a co-expressed ligand. In this case, the receptor could be the yeast pheromone receptor and the ligand the yeast $\alpha$ or a factor. Or the receptor could be a foreign receptor, and the ligand one appropriate to that receptor. In either case, the ligand is a known activator used merely to stimulate activation of the adenylyl cyclase, and the drugs are screened for inhibition of this adenylyl cyclase.

In a third embodiment, the engineered cell is used to screen for drugs which inhibit or activate adenylyl cyclase indirectly, e.g., by their action upon a G protein-coupled receptor. The receptor activates the G protein subunits act on the adenylyl cyclase. In this case, a compatible G protein-coupled receptor and a compatible G protein would be provided with the mammalian adenylyl cyclase in the same yeast cell.

In a fourth embodiment, the engineered cell is used to screen for drugs which inhibit or activate surrogates of pheromone system proteins which act "upstream" of the pheromone receptor.

In those embodiments in which it is desired that the adenylyl cyclase be activated by G$\alpha$ or G$\beta\gamma$, it is necessary that the engineered cell express a form of G$\alpha$ or G$\beta\gamma$ that can carry out this function. If the yeast G$\alpha$ or G$\beta\gamma$ will not activate the mammalian adenylyl cyclase, a mammalian or chimeric G$\alpha$ or G$\beta\gamma$ will be expressed for this purpose. G proteins are discussed in the next section.

3. G Proteins 3.1 Mammalian G Protein Alpha Subunits 3.1.1 Stimulatory (G$\alpha$s) Subunits Through reconstitution analysis of the cyc mutant of S49 murine lymphoma cells, the G$\alpha$s protein was identified (Ross and Gilman (1977) J. Biol. Chem. 252, 6966–6969) as a stimulatory guanine nucleotide-binding protein that coupled hormone receptors to adenylyl cyclase. Mammalian G$\alpha$s cDNA clones have been obtained from human brain (Bray et al. 1986, 1987), human liver (Mattera et al. 1986), bovine brain (Harris et al. 1985), bovine adrenal gland (Robishaw et al. 1986), bovine cerebral cortex (Nukada et al. 1986), hamster lung fibroblasts (Mercken et al. 1990), rat glioma cells (Itoh et al. 1986, 1988), rat olfactory neuroepithelium (Jones and Reed 1987), mouse macrophages (Sullivan et al. 1986), and mouse lymphoma cells (Sullivan et al. 1987; Rall and Harris 1987). Bray et al. (1986) isolated four different G$\alpha$s cDNAs from human brain (G$\alpha$s1–4); these forms appear to arise from a single G$\alpha$s gene by alternate splicing. The G$\alpha$s gene contains 13 exons (Kozasa et al. 1988) which are all present in the long form of G$\alpha$s. A short form of the molecule lacks the 15 amino acids encoded by exon 3. In addition, two alternate mRNAs arise that differ in the presence or absence of a serine codon at the start of exon 4 when different splice sites are used at the 5' end of that exon.

3.1.2 Inhibitory (G$\alpha$i) Subunits

As was the case for receptor-mediated stimulation of adenylyl cyclase, GTP was also found to be required for receptor-dependent inhibition of that enzyme. This pointed to a role for a G protein, distinct from G$\alpha$s in function, in this inhibition. The identification of this protein resulted from studies on the mechanism of action of the *B. pertussis* toxin. This toxin was found to (1) abolish the hormonal inhibition of adenylyl cyclase and (2) to ADP-ribosylate a 41-kd membrane protein. Purification of this toxin substrate permitted its identification as a guanine nucleotide-binding protein related to the mammalian G proteins G$\alpha$s and transducin. The protein was denoted G$\alpha$i (i=inhibitory for adenylyl cyclase).

Three single copy genes encode G protein subunits of the G$\alpha$i type and the predicted proteins (G$\alpha$i-1, G$\alpha$i-2 and G$\alpha$i-3) share 85% sequence identity. In coupling to adenylyl cyclase to signal inhibition of this enzyme, the G$\alpha$i proteins function in concert with G$\alpha$s to control cellular CAMP levels.

G$\alpha$i-1 cDNA clones obtained to date are human (Bray et al. 1987), bovine (Nukada et al. 1986) and rat (Jones and Reed 1987). Human (Itoh et al. 1988; Weinstein et al. 1988; Beals et al. 1987; Michel et al. 1986; Didsbury et al. 1987), rat (Jones and Reed 1987; Itoh et al. 1986), mouse (Sullivan et al. 1986) and bovine (Yatomi et al. 1992) G$\alpha$i-2 cDNA clones have been isolated. G$\alpha$i-3 clones include those from human (Itoh et al 1988; Beals et al. 1088; Suki et al. 1987; Kim et al. 1988) and rat (Itoh et al. 1988; Jones and Reed 1987).

The G$\alpha$i clones preferred in this invention are human clones of the subtypes G$\alpha$i-2 and G$\alpha$i-3; these subtypes are found to be expressed in inflammatory cells. These clones will be expressed in yeast and will be used as targets for the identification of compounds capable of preventing their inhibition of adenylyl cyclase activity. Inhibitors of G$\alpha$i function would be of great utility in the treatment of inflammatory diseases: a large number of cell surface receptors expressed in neutrophils and macrophages mediate signals through G$\alpha$i.

It is likely that a subset of the possible amino acid substitutions that could be made in human G$\alpha$i could yield fully functional, albeit mutant, protein. It is possible that the following mutations would not alter the wild type activity of the protein: Ala59Asp, Glu64Asp, Asp160Glu, Ala163Ser, Val332Ile. It is probable that other amino acid substitutions not specifically cited here could be made without any diminishment of wild type Gαi activity.

3.1.3 Use of Structural Models to Design Chimeric or Other Mutant G Proteins

Models of Gα protein structure may be used to predict amino acid modifications which would not be harmful to activity. Analysis of Gα cDNAs and comparison to conserved sequences present in members of the GTPase superfamily has permitted the identification of five conserved stretches, G1–G5, located throughout a "composite" Gα molecule [Conklin and Bourne (1993); Bourne et al. (1991). In addition, the location of putative α-helices, β strands, loop domains and insertions have been deduced by a comparison of Gα sequences with the known secondary structure of p21 $^{ras}$. Thus α-helices 1–5, β strands 1–6, loops 1–10 and inserts 1–4 have been assigned position in the primary Gα sequence based on comparisons with Ras proteins. Biochemical and genetic studies as well as sequence analysis have led to the delineation of a conceptual model of the Gα protein (Conklin and Bourne 1993). This conceptual model hypothesizes that while the guanine nucleotide binding pocket of Gα is oriented toward the cytoplasm, residues that interact with receptors, effectors and with the Gβγ complex face the plasma membrane. The model also asserts the following:

(1) The N terminus of Gα is a major site for interaction with the Gβγ complex.

(2) The α2 helix and insert 1 regions also contribute to the interaction of Gα with Gβγ.

(3) At least three regions are hypothesized to interface with receptor: the amino and carboxyl termini and the conserved G5 sequence. In the conceptual model the termini rest on the portion of Gα which faces the plasma membrane while the G5 sequence sits at the "top" of the molecule.

(4) The sequences purported to be involved in the interaction of Gα with effector molecules are envisioned to reside on the plasma membrane-proximal aspect of Gα. These sequences include the distal half of the α2 helix, the insert 2-loop 7 sequence and the insert 4-loop 9 sequence.

The orientation of the molecule in this conceptual model is supported in part by experimental evidence that assigns specific amino acids to the GTP binding site based on mutations which have been shown to constitutively activate Gα by inhibiting the GTPase activity of the protein. The mutations in question are homologs of GTPase-inhibiting mutations of p21$^{ras}$.

Monoclonal antibodies generated against N-terminal sequence cause the dissociation of the Gα$_{t1}$ heterotrimer; in addition, N-terminally myristilated peptide inhibits the binding of Gα$_{t1}$ to Gβγ in competitive fashion. Chemical cross-linking experiments indicate the close proximity of the α2 helix and Gβγ and a specific Gαs mutation (G226A) exhibits two deficiencies: the α2 helical region does not undergo GTP-induced conformational change and GTP does not trigger the dissociation of Gβγ from Gαs. The sequence denoted as the α2 helix (analogous to the α2 helix of p21$^{ras}$) is more highly conserved than any other sequence in Gα; this strict conservation further supports an involvement of the helix in interaction with Gβγ in that the formation of the heterotrimer underlies signalling in all G protein pathways described to date.

Additional data has contributed to the development of the conceptual model of Gα. The amino and carboxyl termini of Gα appear to be in close proximity based on cross-linking studies done using mastoparan and based on the specificity of monoclonal antibodies directed against Gα$_{t1}$. Experimental evidence also suggests the proximity of the C terminus and the region that is analogous to the α2 helix of p21$^{ras}$. Finally, insert 1, a large sequence located within loop 2, appears to have GAP function and folds as a domain distinct from the GTPase domain [Markby et al. (1993)].

Experimental evidence indicates that three regions of Gα (the N and C termini and the conserved G5 region) contact the receptor. In addition, Conklin et al. (1993) have obtained data which suggests that amino acid residues at the extreme C-terminus of Gα contribute to the specificity of receptor-G protein interactions. Thus chimeras constructed to replace 4–9 residues at the extreme C-terminus of Gαq with amino acids derived from the same region of Gαi resulted in a Gα protein that can transduce signal from D$_2$ dopamine and A$_1$ adenosine receptors to phospholipase C, a Gq-specific effector. These receptors normally couple to Gαi.

A glycine residue at the −3 position relative to the C-terminus is central to the formation of a β-turn in this region of the Gα molecule; the β-turn appears to be the structural signal that specifies interaction between receptors and α subunits of the Gαi, Gαo, Gαt family [Dratz et al. (1993)]. It has been hypothesized that the interaction between receptor and the C-terminus of Gα results in the conformational change that leads to the open conformation of the latter molecule, i.e., the configuration in which nucleotide exchange can occur.

Mutagenesis of Gαs implicated three regions of the molecule (a portion of the α2 helix, i2-L7 and i4-L9) in the activation of adenylyl cyclase. A second series of experiments utilized peptides derived from Gα$_{t1}$ to deduce the region of that molecule that activates phosphodiesterase; peptides derived from i4–<9 mimicked the ability of Gα$_{t1}$-GTP to stimulate cGMP-phosphodiesterase. The regions identified in effector activation reside on the face of the molecule believed to be oriented toward the plasma membrane; in addition, one of the implicated sequences (the α2 helix) is known to undergo conformational change induced by GTP.

Early crystal structure-based models considered the crystal structure of the GTP-binding domain of E. coli EF-Tu (Jurnak 1985; LaCour et al. 1985), as well as the crystal structure of Ha-ras-p21 (Holbrook and Kim 1989). Recently, a crystal structure of transducin-α (Gtα) complexed with GTPγS has been obtained to a resolution of 2.2 angstrom units (Noel et al. 1993). Analysis of this crystal structure, together with the biochemical and genetic data described above, has been used to derive generalized structure function relationships applicable to all Gα molecules.

In the three-dimensional structure, two domains are most apparent in the Gtα-GTPγS complex, each flanking a guanine nucleotide binding cleft. These are (1) a highly conserved GTPase domain and (2) a highly helical domain that is unique to heterotrimeric G proteins. The GTPase domain is structurally similar to the GTPase domains of p21 Ras and EF-Tu and consists of five α-helices surrounding a six-stranded β-sheet. The other domain is highly helical, unique to heterotrimeric G proteins, and connected to the GTPase domain by two linker sequences. The helical and GTPase domains appear to enclose the GTPγS molecule and an associated Mg$^{2+}$ion. This arrangement suggests that a conformational alteration is required of the Gα molecule in order for nucleotide exchange to occur; it is likely that conformational changes in the linker sequences initiate the movement of the helical domain and the opening of the molecule.

The crystal structure permits delineation of the residues of Gα which interact with the triphosphate portion of the GTP molecule, the essential $Mg^2$ ion, and the nucleoside. In Gtα, the residues that contact the nucleoside and the phosphates form part of the helical domain and linker 2. These regions are implicated in receptor-regulated nucleotide exchange. Noel et al (1993) cite extensive interactions between Gα residues and guanosine; a subset of these interactions are unique to G proteins while others are conserved among members of the GTPase superfamily. The linkages between the nucleotide binding sites and the surface of Gα that purportedly interacts with receptor are also described. The authors assert that "a mechanistically important feature of this system is the elegant manner in which interactions with one portion of the nucleotide support contacts with another. It is likely that these tightly coupled interactions potentiate a highly cooperative receptor-mediated disassembly of the elements that so strongly secure GDP and GTP in the nucleotide-binding cleft" [Noel et al (1993)].

Experimental data exists which implicates specific α-helices and β sheets (α2/β4, α3/β5, α4/β6) in effector binding and activation. These regions were found to form a series of surface loops in the three-dimensional model derived from analysis of the Gtα-GTPγS crystals. Work done with Gtα suggests interaction of these loops with phosphodiesterase or with the inhibitory γ-subunits of that enzyme. Studies accomplished using Gsα/Giα chimeras suggest that these surface loops play a role in the regulation of adenylyl cyclase. In addition, the crystal structure of Gtα-GTPγS indicates how GTP may effect conformational change in these effector-interactive loops. Glycine residues in the α/γ 2 helix interact with the γ-phosphate of GTP and are believed to be the source of the malleability required for the conformational change which occurs upon hydrolsis of GTP. The GDP/GTP-induced changes in α2 are hypothesized to transmit to the α3 and α4 loops through a connecting series of interhelical contacts, thus linking changes in the interaction of γ-phosphate with α2 to the effector-binding surface loops.

The crystal structure draws attention to two residues that appear to play a role in the hydrolysis of GTP. A conserved arginine residue (Arg 174) contacts the γ-phosphate directly and may facilitate its release upon hydrolysis. Mutation of the cognate arginine in Gsα and Giα severely compromises GTPase activity and results in a constitutively active Gα. The structure also suggests the glutamine at position 203 as the initiator of the hydrolytic attack on the γ-phosphate. Glu203 appears to be appropriately oriented to activate a water molecule well-positioned for nucleophilic attack on the γ-phosphate. This glutamate resides in the α2 helix and is conserved among the family of Gα subunits.

As indicated by the foregoing models of Gα structure, the function of the molecule is dependent on its interaction with receptor, the βγ complex, GTP or GDP, and effector molecules. Mutation of residues that experimental evidence or crystal structure-derived data have indicated as contributing to these numerous interactions could compromise Gα function. The following sequences, residues and domains have been shown to be particularly important to Gα function: N-terminal residues, residues at the extreme C-terminus (particularly the glycine at position -3), the highly conserved α2 helix, cognates of Arg 174 of Gαt, cognates of glutamine 203 of Gαt, the GTPase domain, and the α2/β4, α3/β5, and α4/β6 regions. Other sequences would appear to be important, based on their conservation among members of the GTPase family or in that they are unique to heterotrimeric G protein α-subunits. These include the conserved sequences G1–G5 and the regions identified as inserts through comparisons made between Gα and Ras proteins. It must be stated that a definitive citation of functionally important regions cannot be made as this remains an intense area of research.

It is expected that future studies will identify the residues in the larger domains cited above that contribute most to function and identify additional specific residues whose characteristics are central to Gα function. Although conservative mutations in important regions of Gα may leave the function of the molecule intact, the more radical the change, the higher the likelihood of interference with protein function. The models as outlined above underscore an important feature of the Gα molecule. Conformational change is inherent to the exchange of nucleotide and that exchange is central to Gα function. The conformational change appears to occur as a wave of signal transmission from one domain of the molecule to another. The models thus emphasize that alterations in any one of the functional domains of the protein can affect the final transduction of signal, i.e., the function of the molecule depends on successful cooperativity of several domains.

It must be stated that mutations can be made, however, which can contribute to the utility of the Gα protein in experimental systems. As an example, mutations which compromise the GTPase function specifically, without affecting Gα interaction with effector proteins, results in a constitutively active protein. In a subset of experimental scenarios, a constitutively active Gα is a desirable molecular reagent.

It may be possible to make the following conservative amino acid substitutions in the sequence of human Gαs without compromising the wild-type activity of the protein: Ile183Leu, Asp184Glu, Leu198Val, Val218Leu, and Ile373Val. It is likely that other conservative amino acid substitutions not specifically cited here may be made in the sequence of Gαs without inducing significant change in the activity of the wild type protein.

3.2 Mammalian Gβ and Gγ Subunits

As of early 1994, at least four mammalian Gβ subunits were known and had been cloned. Both human and bovine clones of Gβ1 (Codina J. et al. (1986) FEBS Lett. 207, 187–192; Sugimoto K. et al. (1985) FEBS Lett. 191, 235–240; Fong H. K. W. et al. (1986) Proc. Natl. Acad. Sci. USA 83, 2162–2166) and Gβ2 (Fong H. K. W. et al. (1987) Proc. Natl. Acad. Sci. USA 84, 3792–3796; Gao B. et al. (1987) Proc. Natl. Acad. Sci. USA 84, 6122–6125) have been isolated. A human Gβ3 (Levine M. A. et al. (1990) Proc. Natl. Acad. Sci. USA 87, 2329–2333) and mouse Gβ4 (Von Weizsacker E. et al. (1992) Biochem. Biophys. Res. Commun. 183, 350–356) have also been cloned. Five complete mammalian Gγ subunits have been cloned: bovine Gγ1 (Hurley J. B. (1985) Proc. Natl. Acad. Sci. 81, 6948–6952), bovine Gγ2 (Robishaw J. D. (1989) J. Biol. Chem. 264, 15758–15761), bovine Gγ3 (Cali J. J et al. (1992) J. Biol. Chem. 267, 24023–24027), bovine and rat Gγ5 (Fisher K. J. and Aronson N. N. (1992) Mol. Cell. Biol. 12, 1585–1591), and bovine Gγ7 (Cali J. J. et al. (1992) J. Biol. Chem. 267, 24023–24027). Part of a sixth Gγ subunit, Gγ4, has been isolated (Gautam N. et al. (1990) Proc. Natl. Acad. Sci. USA 87, 7973–7977).

Various combinations of Gβ and Gγ have been observed in vitro and therefore have the potential to be physiologically active. For example, Gβ1 can dimerize with Gγ1, Gγ2, Gγ3, and Gγ5 (Iniguez-Lluhi J. A. (1992) J. Biol. Chem. 267, 23409–23417), and β1γ1, β1γ2, and β1γ5 stimulate phosphoinositide hydrolysis by phospholipase C β2 (Katz A.

et al. (1992) Nature 360, 686–688). Other combinations are not observed. For example, Gβ2 does not dimerize with Gγ1 (Schmidt C. J. et al. (1992) J. Biol. Chem. 267, 13807–13810; Pronin A. N. and Gautam N. (1992) Proc. Natl. Acad. Sci. USA 89, 6220–6224). The effects of βγ dimers on adenylyl cyclases depends on both the isoform of adenylyl cyclase and the particular βγ dimer in question. While type 1 adenylyl cyclase is inhibited to varying degrees by different βγ dimers, the same dimers will potentiate the stimulatory effect of Gαs on type 2 adenylyl cyclase (I niguez-Lluhi J. A. (1992) J. Biol. Chem. 267, 23409–23417). In both cases the potencies of β1γ2, β1γ3, β2γ2, and β2γ3 are reported to be equivalent and greater than that of β1γ1.

The following additional references may be of value:

Gbeta5:

A fifth member of the mammalian G-protein beta-subunit family. Expression in brain and activation of the beta 2 isotype of phospholipase C. Watson A J, Katz A Simon M I, 19994, J Biol Chem, 269: 22150–6.

Ggamma8:

A novel GTP-binding protein gamma-subunit, Ggamma8, is expressed during neurogenesis in the olfactory and vomeronasal neruoepithelia. Ryba N J P, Tirindelli R, J Biol Chem, 270: 6757–6767, 1995.

Ggamma7:

Selective Tissue Distribution of G protein gamma subunits, Including a new form of the gamma subunits identified by CDNA Cloning. Cali J J, Balcueva E A, Rybalkin I, and Robishaw J D, J Biol Chem, 267: 24023–24027, 1992.

Ggamma6:

Existence of two gamma subunits of the G proteins in brain. J. D. Robishaw, V. K. Kalman, C. R. Moomaw, C. A. Slaughter, J Biol Chem, 264: 15758–15761, 1989.

Mutant Gβ and Gγ subunits may be designed in a manner analogous to that set forth with respect to Gα subunits.

4. Drug Screening

The identification of biological activity in new molecules has historically been accomplished through the use of in vitro assays or whole animals. Intact biological entities, either cells or whole organisms, have been used to screen for anti-bacterial, anti-fungal, anti-parasitic and anti-viral agents in vitro. Cultured mammalian cells have also been used in screens designed to detect potential therapeutic compounds. A variety of bioassay endpoints are exploited in mammalian cell screens including the stimulation of growth or differentiation of cells, changes in cell motility, the production of particular metabolites, the expression of specific proteins within cells, altered protein function, and altered conductance properties. Cytotoxic compounds used in cancer chemotherapy have been identified through their ability to inhibit the growth of tumor cells in vitro and in vivo. In addition to cultures of dispersed cells, whole tissues have served in bioassays, as in those based on the contractility of muscle.

In vitro testing is a preferred methodology in that it permits the design of high-throughput screens: small quantities of large numbers of compounds can be tested in a short period of time and at low expense. Optimally, animals are reserved for the latter stages of compound evaluation and are not used in the discovery phase; the use of whole animals is labor-intensive and extremely expensive.

Microorganisms, to a much greater extent than mammalian cells and tissues, can be easily exploited for use in rapid drug screens. Yeast provide a particularly attractive test system; extensive analysis of this organism has revealed the conservation of structure and function of a variety of proteins active in basic cellular processes in both yeast and higher eukaryotes.

The functional expression of a mammalian adenylyl cyclase in yeast provides for the design of inexpensive screens useful in the identification of modulators of this enzyme, the activity of which is required for the generation of a central signalling molecule in mammalian cells. Any chemical entity, or combination of chemical entities, whether natural or synthetic, may be screened for the ability to modulate the mammalian adenylyl cyclase. These modulators may act directly on the cyclase to alter the activity of the enzyme or may affect the ability of the following molecules to alter adenylyl cyclase activity: Gαs, Gαi, or Gβγ.

4.1 Drugs, Generally

Suitable chemical entities, from among which modulators of adenylyl cyclase may be identified, include nucleotide analogs (in particular, analogs of ATP, the natural substrate of adenylyl cyclase, and analogs of GTP, an activator of Gαs). Forskolin, a diterpene, binds directly to adenylyl cyclase and is a potent stimulator of that molecule. Therefore, forskolin-like structures, forskolin derivatives, and the diterpene class of compounds as a whole would be suitable chemical entities to test for effect on adenylyl cyclase activity. Synthetic peptides are also of interest. By way of example, peptides based on the calmodulin-binding domain of calmodulin-dependent adenylyl cyclases could serve as modulators of cyclase activity. In addition, peptides or molecules of any structure which inhibit the interaction between the cyclase and known endogenous modulators of adenylyl cyclase activity are of interest. Known endogenous adenylyl cyclase modulators include $Ca^{2+}$, $Ca^{2+}$/calmodulin, protein kinase C, protein kinase A, Gαs, Gαi, Gβγ, and adenosine.

Activation of protein kinase C can stimulate adenylyl cyclase activity and adenylyl cyclase has been shown to be a direct target for phosphorylation by protein kinase C (Yoshimasa et al. (1991) Nature 327, 67–70). P2 purinergic and M5 muscarinic receptors, stimulators of the protein kinase C pathway, activate adenylyl cyclase (Johnson et al. (1991) J. Pharmacol. Exp. Ther. 39, 539–546). The adenylyl cyclases that have been cloned to date have been tested for susceptibility to regulation by protein kinase C activation: the basal activity of the type 2 enzyme is greatly increased by activation of protein kinase C whereas the activities of types 1 and 3 are affected to a lesser degree. In contrast, adenylyl cyclase types 4, 5, and 6 are not stimulated by protein kinase C activation (Jacobowitz et al. (1993) J. Biol. Chem. 268, 3829–3832; Yoshimura and Cooper (1993) J. Biol. Chem. 268, 4604–4607).

Studies have indicated a decrease in forskolin-stimulated adenylyl cyclase activity following exposure of mammalian cell membranes to protein kinase A (Premont et al. )1992) Endocrinology 131, 2774–2783; Yoshimura and Cooper (1992) PNAS 89, 6716–6720). A subset of the identified mammalian adenylyl cyclases appear to be susceptible to negative regulation by protein kinase A-dependent phosphorylation. Putative protein kinase A phosphorylation sites have been identified in the sequence of each of the enzymes, with the exception of type 4 adenylyl cyclase. The locations of the putative sites of phosphorylation are conserved in types 5 and 6 but vary among the other cyclases (Iyengar (1993) FASEB J. 7,768–775.

4.2 Peptide Drugs

One class of potential modulators of particular interest is the peptide class. The term "peptide" used herein to refer to a chain of two or more amino acids, with adjacent amino acids joined by peptide (—NHCO—) bonds. Thus, the peptides of the present invention include oligopeptides, polypeptides, and proteins. Preferably, the peptides of the present invention are 2 to 200, more preferably 5 to 50, amino acids in length. The minimum peptide length is chiefly dictated by the need to obtain sufficient potency as an activator or inhibitor. The maximum peptide length is only a function of synthetic convenience once an active peptide is identified. When peptide drugs are being assayed, the yeast cells may be engineered to express the peptides, rather than being exposed to the peptides simply by adding the peptides to the culture medium.

4.3 Autocrine Cells

While others have engineered yeast cells to facilitate screening of exogenous drugs as receptor agonists and antagonists, the cells did not themselves produce both the drugs and the receptors. Yeast cells engineered to produce the receptor, but that do not produce the drugs themselves, are inefficient. To utilize them one must bring a sufficient concentration of each drug into contact with a number of cells in order to detect whether or not the drug has an action. Therefore, a microtiter plate well or test tube must be used for each drug. The drug must be synthesized in advance and be sufficiently pure to judge its action on the yeast cells. When the yeast cell produces the drug, the effective concentration is higher.

4.4 Peptide Library

In one embodiment, the yeast cells are engineered to express a peptide library. A "peptide library" is a collection of peptides of many different sequences (typically more than 1000 different sequences), which are prepared essentially simultaneously, in such a way that, if tested simultaneously for some activity, it is possible to characterize the "positive" peptides. The peptide library of the present invention takes the form of a yeast cell culture, in which essentially each cell expresses one, and usually only one, peptide of the library. While the diversity of the library is maximized if each cell produces a peptide of a different sequence, it is usually prudent to construct the library so there is some redundancy. Moreover, each sequence should be produced at assayable levels.

The peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide-encoding DNA molecule is introduced into a particular cell, it is not predictable which peptide that cell will produce. However, based on a knowledge of the manner in which the mixture was prepared, one may make is certain statistical predictions about the mixture of peptides in the peptide library.

It is convenient to speak of the peptides of the library as being composed of constant and variable residues. If the nth residue is the same for all peptides of the library, it is said to be constant. If the nth residues varies, depending on the peptide in question, the residue is a variable one. The peptides of the library will have at least one, and usually more than one, variable residue. A variable residue may vary among any of two to any of all twenty of the genetically encoded amino acids; the range of possibilities may be different, if desired, for each of the variable residues of the peptide. Moreover, the frequency of occurrence of the allowed amino acids at particular residue positions may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA.

Once the necessary "degenerate" DNA is complete, it must be joined with the DNA sequences necessary to assure the expression of the peptide, as discussed in more detail elsewhere, and the complete DNA construct must be introduced into the yeast cell.

4.5 Periplasmic Secretion

The cytoplasm of the yeast cell is bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The peptide library may be secreted into the periplasm by one of two distinct mechanisms, depending on the nature of the expression system to which they are linked. In one system, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction would likely yield activation of the linked pheromone response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. We anticipate that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

5. Detection of Inhibition or Activation of Mammalian Adenylyl Cyclase Activity

For the engineered yeast cells to be useful in screening drugs for the ability to inhibit or activate a mammalian adenylyl cyclase, there must be a detectable change in adenylyl cyclase activity. This change (the signal) must be detectable against the background (the basal level of adenylyl cyclase activity in the absence of the drug). The signal may be change in the growth rate of the cells, or other phenotypic changes, such as a color change or luminescence.

The endogenous (yeast) adenylyl cyclase contributes to background. This contribution may be reduced by using yeast cells which bear a mutant allele of yeast adenylyl cyclase, cdc 35-1, as the endogenous adenylyl cyclase.

This allele encodes a temperature-sensitive enzyme that is active when the cells are grown at room temperature; at 30° C. or higher, the cyclase is inactive and the yeast cells are incapable of growth. This strain also preferably displays the Cam phenotype, which reflects an ability for growth rescue at the higher temperatures through the addition of exogenous cAMP (since yeast displaying the Cam phenotype are capable of taking up and utilizing cAMP) (Matsumoto et al. (1982) J. Bacteriol. 150, 277–285).

Thus, in a preferred embodiment, the background of the test strain provides for a simple metric of the function of the mammalian cyclase when that protein is introduced into these cells via an expression plasmid. If the mammalian adenylyl cyclase is active, the yeast grow at temperatures greater than 30° C., in a range where the yeast cyclase is non-functional. Growth of the test yeast cells is a simple and elegant indicator of the activity of the mammalian enzyme.

Alternatively, one may use a host strain in which the gene encoding the endogenous adenylyl cyclase (CYR1) is completely, unconditionally inactivated, e.g., by deletion. Such yeast could grow in the presence of glucose provided that they also exhibited the Cam phenotype and were provided with exogenous cAMP. Alternatively, these cells would also be capable of growth if they expressed rat adenylyl cyclase and Gαs. Thus, hosts other than the cdc 35-1 mutant strain that was used in the invention reported here could be used and may have certain advantages. For example, spontaneous reversions in the cdc35–1 allele could give rise to adenylyl cyclase with wild type activity. Such reversions can be virtually eliminated using deletion mutants of the endogenous adenylyl cyclase.

Rather than relying on the effect of the adenylyl cyclase on endogenous components of the cell for signal generation, it is also possible to select or screen for adenylyl cyclase activity by means of a marker gene engineered into the yeast cell. A marker gene is a gene whose expression causes a phenotypic change which is screenable or selectable. If the change is selectable, the phenotypic change creates a difference in the growth or survival rate between cells which express the marker gene and those which do not. If the change is screenable, the phenotype change creates a difference in some detectable characteristic of the cells, by which the cells which express the marker may be distinguished from those which do not. Selection is preferable to screening.

Situations may occur wherein it would be advantageous to use a readout other than growth as an assay of cyclase activity. While growth rates require at least a day to measure, direct readouts of transcriptional activity offer the possibility of more rapid assays. For example, by placing the bacterial gene encoding lacZ under the control of the FUS1 promoter, activation of the yeast pheromone response pathway can be detected in less than an hour by monitoring the ability of permeabilized yeast to produce color from a chromogenic substrate. The rapidity of such a readout would, in itself, be advantageous. And such a readout would be necessary to monitor cyclase activity under conditions where the yeast do not grow.

In mammalian cells cAMP influences transcription from a panel of genes by activating protein kinase A (PKA), which phosphorylates and thereby activates transcription factor CREB (reviewed in Brindle, P K and Montminy, M R (1992) Curr. Opinion Gen. Dev., 2: 199–204). In yeast, however, only a few genes are known to be affected by PKA: ADH2 (Denis, C L et al (1992) Mol Cell Biol 12: 1507–1514), UBI4 (Tanaka, K et al (1988) EMBO J. 7: 495–502), CTT1 (Marchler, G (1993) EMBO J 12: 1997–2003), and various ribosomal protein genes like RPS13 (Sussel, L and Shore, D (1991) Proc Natl Acad Sci USA 88: 7749–7753). The cAMP-dependent activation of the ribosomal genes is mediated by the yeast RAP1 transcription factor, which binds to the DNA sequence RMAC-CCANNCAYY (SEQ ID No:1) in a wide variety of yeast promoters (Klein, C and Struhl, K (1994) Mol Cell Biol 14: 1920–1928). Indeed, the RAP1 binding site can increase transcription from a heterologous HIS3 promoter (Klein, C and Struhl, K (1994) Mol Cell Biol 14: 1920–1928), suggesting that an upstream regulatory sequence containing RAP1 binding sites could be constructed and linked to a reporter gene such as lacZ. Such a construct could provide a rapid, colorimentric readout of the activity of mammalian adenylyl cyclase in yeast. Other useful reporters include such genes as alkaline phosphatase, chloramphenicol acetyl transferase, luciferase and fluorescent green protein (FGP), which can be used to generate colorimetric, luminescent, fluorescent or radioisotopic readouts. (The latter requires a radioisotopic substrate.)

Thus, a marker gene may be coupled to the mammalian adenylyl cyclase so that expression of the marker gene is dependent on activity of the adenylyl cyclase. This coupling may be achieved by operably linking the marker gene to a cyclic AMP-responsive promoter. The term "cyclic AMP-responsive promoter" indicates a promoter which is regulated by either cyclic AMP or a metabolic product produced as a consequence of cyclic AMP production. For example, the cauliflower mosaic virus 35S RNA promoter appears to be regulated by cAMP in S. cerevisiae (Ruth et al. (1992) Mol. Gen. Genet. 235, 365–372). The promoter could be one which is natively responsive to cyclic AMP, or one engineered to be so responsive by incorporation of a suitable operator.

In one embodiment, the promoter is activated upon activation of the cyclase, in which case, for selection, the expression of the marker gene should result in a benefit to the cell. A preferred marker gene is the imidazoleglycerol phosphate dehydratase gene (HIS3). If a cyclic AMP responsive promoter is operably linked to a beneficial gene, the cells will be useful in screening or selecting for adenylyl cyclase activators. If it is linked to a deleterious gene, the cells will be useful in screening or selecting for inhibitors.

Alternatively, the promoter may be one which is repressed by cyclic AMP, thereby preventing expression of a product that is deleterious to the cell. With a cyclic AMP-repressed promoter, one screens for agonists by linking the promoter to a deleterious gene, and for antagonists, by linking it to a beneficial gene.

Repression may be achieved by operably linking a cyclic AMP-induced promoter to a gene encoding mRNA that is antisense to at least a portion of the mRNA encoded by the marker gene (whether in the coding or flanking regions), so as to inhibit translation of that mRNA. Repression may also be obtained by linking a cyclic AMP-induced promoter to a gene encoding a DNA-binding repressor protein, and incorporating a suitable operator site into the promoter or other suitable region of the marker gene.

Suitable positively selectable (beneficial) genes include the following: URA3, LYS2, HIS3, LEU2, TRP1; ADE1,2, 3,4,5,7,8; ARG1,3,4,5,6,8; HIS1,4,5; ILV1,2,5; THR1,4; TRP2,3,4,5; LEU1,4; MET2,3,4,8,9,14,16,19; URA1,2,4,5, 10; HOM3,6; ASP3; CHO1; ARO 2,7; CYS3; OLE1; INO1, 2,4; PRO1,3 Countless other genes are potential selective markers. The above are involved in well-characterized biosynthetic pathways.

The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In a more complex version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on α-aminoadipate as sole nitrogen source), GAL1 (encodes galactokinase; expression of GAL1 is toxic in the presence of galactose in strains that contain mutations in either GAL7 (encodes galactotransferase) or GAL 10 (encodes epimerase) genes); CYH2 (encodes ribosomal protein L29; cycloheximide-sensitive allele is dominant to resistant allele), CAN1 (encodes arginine permease; null allele confers resistance to the arginine analog canavanine), and other recessive drug-resistant markers.

The marker gene may also be a screenable gene. The screened characteristic may be a change in cell morphology, metabolism or other screenable features. Suitable markers include beta-galactosidase (Xgal, $C_{12}FDG$, Salmon-gal, Magenta-Gal (latter two from Biosynth Ag)), acid or alkaline phosphatase, horseradish peroxidase, exo-glucanase (product of yeast exb1 gene; nonessential, secreted); luciferase; and chloramphenicol transferase. Some of the above can be engineered so that they are secreted (although not β-galactosidase). The preferred screenable marker gene is beta-galactosidase; yeast cells expressing the enzyme convert the colorless substrate Xgal into a blue pigment. Again, the promoter may be cyclic AMP-induced or cyclic AMP-inhibited.

To identify inhibitors of adenylyl cyclase, in one embodiment the gene encoding MATα2p is placed under the control of a promoter containing RAP1 binding site, so that transcription of MATα2 is cAMP dependent. A lacZ gene construct is then placed under the control of any haploid-specific promoter. In a yeast cell transformed with these two constructs, the expression of lacZ—and therefore the development of blue color—will then be under the control of MATα2p, which in turn will be controlled by cAMP levels. Specifically, in the presence of active adenylyl cyclase, the yeast will be white due to expression of MATα2p and consequent inhibition of lacZ expression. If cyclase is inhibited, MATα2p will decline, resulting in increased lacZ expression from the haploid-specific promoter. Examples of haploid-specific promoters include but are not limited to promoters for the GPA1, STE4, STE18 genes.

Another strategy to discover inhibitors of adenylyl cyclase is to use promoters that are repressed by cAMP. cAMP-repressible elements are found in the promoters of SSA3 (Boorstein, W R and Craig, E A, 1990, EMBO J, 9: 2543–2553) and CTT1 (Marchler, G C et al 1993, EMBO J, 12: 1997–2003), and may be present in the UBI4 promoter (Tanaka, K K et al, 1989, EMBO J, 7: 495–502). These promoters, if engineered to direct the transcription of a screenable marker like lacZ, can provide a readout of inhibition of adenylyl cyclase activity. Specifically, inhibition of adenylyl cyclase will result in reduced cAMP levels that will relieve repression of lacZ expression, resulting in the development of blue color within several hours in a culture of yeast exposed to an inhibitor. Such readouts can be very sensitive to small changes in levels of cAMP caused by agonists or antagonists and do not have some of the potential drawbacks of growth readouts discussed above.

6. Detection of Inhibition or Activation of Proteins Other Than Adenylyl Cyclase It is possible to detect inhibitors or activators of proteins other than adenylyl cyclase provided that the yeast cell expresses or is engineered to express the protein of interest in such a manner that it is functionally "coupled", directly or indirectly, to the adenylyl cyclase.

For example, the cells could be used to screen for inhibitors or activators of a cyclase associated protein (CAP). CAP has been identified in yeast which also interacts with the yeast cytoskeleton (Kawmukai et al, 1992, Mol. Biol. Cell, 3: 167–180) and may be a regulator of the yeast adenylyl cyclase activity.

Similarly, a human homolog of the yeast CAP gene has been identified and this may function as a regulator of the human adenylyl cyclase. Such regulators may potentially feed in signals from other signal transduction pathways. These and other as yet unidentified regulators which interact with adenylyl cyclase(s) and modify their activity may be used in further embodiments of the present invention for the discovery of agonist or antagonist activities affecting any step of the signal transduction pathway(s) which are coupled to the cloned mammalian adenylyl cyclase.

The best characterized regulator of adenylyl cyclase is the G protein, or, more precisely, the Gα subunit and/or the Gβγ complex resulting from the dissociation of the G protein. Consequently, the yeast cells of the present invention may be used to test drugs for the ability to interact with an exogenous (or chimeric) G protein-coupled receptor or other PSP surrogate. The yeast cells must express both the exogenous G protein-coupled receptor (or other PSP surrogate), and a complementary (usually exogenous or chimeric) G protein (or other PSPs necessary for the PSP surrogate to function in the pheromone system, if need be after activation by a drug), and these molecules must be presented in such a manner that adenylyl cyclase activity is affected.

If the yeast cell expresses a G protein-coupled receptor, and the stimulation of this receptor results in the dissociation of a G protein also expressed by the yeast cell, and either the Gα subunit or the Gβγ complex then interacts with the mammalian adenylyl cyclase, to increase or decrease its level of activity, the G protein-coupled receptor (and the G protein) may be said to be coupled to the adenylyl cyclase. That is, inhibitors or activators of the receptor will affect adenylyl cyclase activity. Thus, a yeast cell may be engineered so it can be used to detect inhibitors or activators of an exogenous (usually mammalian) G protein coupled receptor by virtue of their effect on the activity of a coupled adenylyl cyclase. This coupling may be facilitated by the use of corresponding exogenous (or chimeric) Gα, Gβ and/or Gγ subunits, and the signal-to-noise ratio may be improved by partial or total inactivation of the endogenous genes (or their products).

An exogenous G protein coupled receptor is one example of a PSP surrogate, the corresponding yeast protein being the α- or a-factor receptor. However, it is possible to screen for inhibitors or activators of surrogates of other PSPs, provided that they directly or indirectly affect the stimulation of an endogenous or exogenous G protein-coupled receptor, and thereby of the G protein-coupled adenylyl cyclase.

Examples of these "upstream" PSPs include:
Farnesyltransferases and carboxymethyltransferases. After expression, a-factor is farnesylated by RAM1p and RAM2p and carboxymethylated by Ste14p. These modifications are required for activity.

RAM1p and RAM2p are homologous to the subunits of the heterodimeric mammalian farnesyltransferase, which itself is necessary for membrane association of mammalian Ras proteins. If a yeast cell is engineered to express the mammalian farnesyltransferase, it may be used to identify drugs which interact with that enzyme by determining whether a functional a-factor is produced. Similarly, Ste14p is homologous to mammalian carboxymethyltransferases, which play regulatory roles in controlling the function of low molecular weight G proteins (Ras, Rho, Rab).

Proteases. The PSP may be a yeast protease, such as KEX2, STE13 or KEX1. Yeast α-factor pheromone is generated through the controlled and limited proteolysis of precursor proteins by these proteases. A yeast cell may be engineered to express an inactive precursor of yeast α-factor in which a peptide linker, corresponding to the cleavage site of a surrogate non-yeast protease, is incorporated so that cleavage will liberate mature α-factor (or its functional homologue). For example, the PSP surrogate may be HIV protease, with the cleavage site of HIV protease being substituted for the yeast protease cleavage sites in the α-factor precursor. The precursor and the HIV protease are co-expressed in the yeast cell. Proteolysis by HIV protease will give rise to production of mature α-factor and initiation of signal transduction. This system may be used to identify inhibitors of HIV protease.

Preferably, unlike yeast cells occurring in nature, the yeast cell is engineered not only to express the α-factor precursor, but also the α-factor receptor, so that a single haploid type of yeast is all that is required to conduct the assay.

ABC Transporters. Ste6 is the yeast ABC transporter necessary for the export of a-factor. The yeast cell is engineered to express both a-factor and a foreign ABC transporter. This transporter may be one which is not, by itself, able to transport a-factor, but which in the presence of a drug of interest, is capable of doing so, or it may be one which is already functional. Preferably, the yeast cell is engineered to express not only a-factor, but also the a-factor receptor.

If an endogenous pheromone receptor (or other cognate PSP) is produced by the yeast cell, the assay may not be able to readily distinguish between peptides which interact with the pheromone receptor (or other cognate PSP) and those which interact with the exogenous receptor (or other PSP surrogate). It is therefore desirable that the endogenous gene be deleted or otherwise rendered nonfunctional.

The present invention may be used to identify inhibitors or activators of many mammalian receptors, including but not limited to, receptor tyrosine kinases and cytokine receptors (such as those for IL-3, IL-5, GM-CSF, M-CSF and EPO etc.), G protein-coupled chemokine receptors (such as RANTES, MCP-3, MCP-1, MIP-1α and IL-8 receptor), growth factor receptors (such as EGFR and PDGFR etc.), and multi-subunit immune recognition receptors also known as MIRRs (such as FcεRI, and FcγRII etc.). Further receptors useful in the current invention include the G protein-coupled C5a peptide receptor, the thrombin peptide receptor (PAR1) and its homolog PAR2, formyl peptide and bradykinin receptors, muscarinic receptors, adrenergic receptors, melatonin, galanin, glucagon and orphan receptors and transporter proteins such as the multidrug resistance protein (MDR).

6.1 Mammalian G Protein-Coupled Receptors

The yeast cells of the present invention may be used to identify drugs which modulate the activity of a mammalian G protein-coupled receptor. In this embodiment, the yeast cell is engineered to express a mammalian G protein-coupled receptor, Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors. Examples include receptors cloned by Neote et al. Cell 72, 415 (1993); Kouba et al. FEBS Lett. 321, 173 (1993); Birkenbach et al. J. Virol. 67, 2209 (1993).

The "exogenous G protein-coupled receptors" of the present invention may be any G protein-coupled receptor which is exogenous to the wild-type yeast cell which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human receptor. The exogenous receptor is also preferably a seven transmembrane segment receptor.

Suitable receptors include, but are not limited to, dopaminergic, muscarinic cholinergic, α-adrenergic, β-adrenergic, opioid (including delta and mu), cannabinoid, serotoninergic, and GABAergic receptors. Other suitable receptors are listed in Table 2 of WO94/23025. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed in Table 2 of WO94/23025. Thus, the gene would be operably linked to a promoter functional in yeast and to a signal sequence functional in yeast. Suitable promoters include Ste2, Ste3 and gal10. Suitable signal sequences include those of Ste2, Ste3 and of other genes which encode proteins secreted by yeast cells. Preferably, the codons of the gene would be optimized for expression in yeast. See Hoekema et al., Mol. Cell. Biol., 7: 2914–24 (1987); Sharp, et al., 14: 5125–43 (1986).

The homology of STRs is discussed in Dohlman et al., Ann. Rev. Biochem., 60: 653–88 (1991). When STRs are compared, a distinct spatial pattern of homology is discernable. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

It is conceivable that a foreign receptor which is expressed in yeast will functionally integrate into the yeast membrane, and there interact with the endogenous yeast G protein. More likely, either the receptor will need to be modified (e.g., by replacing its V–VI loop with that of the yeast STE2 or STE3 receptor), or a compatible G protein should be provided.

If the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible.

Preferably, the yeast genome is modified so that it is unable to produce the endogenous a- and α-factor receptors in functional form. Otherwise, a positive assay score might reflect the ability of a peptide to activate the endogenous G protein-coupled receptor, and not the receptor of interest.

When the PSP surrogate is an exogenous G protein-coupled receptor, the yeast cell must be able to produce a G protein which is activated by the exogenous receptor, and which can in turn activate the mammalian adenyl cyclase. It is possible that the endogenous yeast Gα subunit (e.g., GPA) will be sufficiently homologous to the "cognate" Gα subunit which is natively associated with the exogenous receptor for coupling to occur. More likely, it will be necessary to genetically engineer the yeast cell to produce a foreign Gα subunit which can properly interact with the exogenous receptor. For example, the Gα subunit of the yeast G protein may be replaced by the Gα subunit natively associated with the exogenous receptor.

Dietzel and Kurjan, Cell, 50: 1001 (1987) demonstrated that rat Gαs functionally coupled to the yeast Gβγ complex. However, rat Gαi2 complemented only when substantially overexpressed, while Gα0 did not complement at all. Kang, et al., Mol. Cell. Biol., 10: 2582 (1990). Consequently, with some foreign Gα subunits, it is not feasible to simply replace the yeast Gα.

Therefore, alternatively, the yeast Gα subunit is replaced by a chimeric Gα subunit in which a portion, e.g., at least about 20, more preferably at least about 40, amino acids, which is substantially homologous with the corresponding residues of the amino terminus of the yeast Gα, is fused to a sequence substantially homologous with the main body of a mammalian (or other exogenous) Gα. While 40 amino acids is the suggested starting point, shorter or longer portions may be tested to determine the minimum length required for coupling to yeast Gβγ and the maximum length compatible with retention of coupling to the exogenous receptor. It is presently believed that only the final 10 or 20 amino acids at the carboxy terminus of the Gα subunit are required for interaction with the receptor.

If the yeast cell is engineered to express a mammalian or chimeric Gαi, one may screen for specific modulators of the inhibitory activity of that Gαi. The following receptors have been shown to activate adenylyl cyclase via signalling to Gαs:

| | |
|---|---|
| β₁-adrenergic | histamine H2 |
| β₂-adrenergic | glucagon |
| D1 dopamine | calcitonin |
| D5 dopamine | glucagon-like peptide 1 |
| vasoactive intestinal peptide | adrenocorticotropic |
| follicle stimulating hormone | melanocyte stimulating hormone |
| luteinizing hormone/choriogonadotropin | secretin |
| vasopressin V2 | adenosine A2 |
| thyroid stimulating hormone | |

The following receptors have been shown to be involved in the inhibition of adenylyl cyclase; this inhibition is believed to occur via signalling to a G protein member of the Gi/Go family:

| | |
|---|---|
| adenosine A1 | angiotensin II type 1 |
| adenosine A3 | cannabinoid |
| α-adrenergic | bradykinin |
| muscarinic acetylcholine receptor type 2 | GABA |
| muscarinic acetylcholine receptor type 4 | galanin |
| D2 dopamine | metabotropic glutamate type 2 |
| D4 dopamine | metabotropic glutamate type 3 |
| 5HT1a | metabotropic glutamate type 4 |
| 5HT1b | melatonin |
| 5HT1d | NPY1 |
| 5HT1e | NPY2 |
| 5HT1f | somatostatin 2 |
| formylMet—Leu—Phe | somatostatin 3 |
| delta opioid | somatostatin 4 |

The yeast cell may also engineered to express mammalian or chimeric Gβ and/or Gγ subunits as well as mammalian or chimeric Gαs. The Gαs and Gβγ subunits will associate to form a heterotrimeric G protein to which the receptor is coupled. Stimulation of the receptor will greatly increase the rate of activation of Gαs causing dissociation of the Gαs and Gβγ; the Gαs will subsequently activate the mammalian adenylyl cyclase.

6.2 Farnesyltransferases

The activity of yeast a-factor requires its farnesylation (mediated by protein farnesyltransferase, comprised of Ram1p and Ram2p), proteolytic cleavage of the C-terminal 3 amino acids of the primary translation product (mediated by an as yet unidentified enzyme), and carboxymethylation of the C-terminal cysteine (mediated by Ste14p). The yeast and mammalian farnesyltransferases are structurally and functionally similar (Gomez R et al., Biochem. J. 289: 25–31, 1993; Kohl N E et al., J. Biol. Chem. 266: 18884–8, 1991). Sequence homologies exist between the genes encoding the α and β subunits of the yeast farnesyltransferase (RAM2 and RAM1, respectively) and the genes encoding the α and β subunits of the mammalian farnesyltransferase (Kohl N E et al., J. Biol. Chem. 266: 18884–8, 1991; Chen W J et al., Cell 66: 327–34, 1991). It has been observed that the β subunit of mammalian farnesyltransferase and Ram1p are 37% identical in amino acid sequence (Chen W J et al., Cell 66: 327–34, 1991).

The importance of a screen for inhibitors of farnesyltransferase is suggested by the facts that mammalian p21ras, a preeminent regulator of the growth and differentiation of mammalian cells that is involved in a variety of cancers, is a substrate for the farnesyltransferase and that farnesylation of p21ras is required for its activity. In fact, a synthetic organic inhibitor of farnesyl protein transferase has been shown to selectively inhibit ras-dependent cell transformation (Kohl et al., Science 260, 1934 (1993). Of the two subunits of farnesyltransferase, the β subunit is a more attractive target for inhibitors, since it is apparently dedicated to farnesylation. The α subunit, in contrast, is shared by geranylgeranyltransferase I, an enzyme involved in the modification of the Gγ subunits of heterotrimeric G proteins and small molecular weight G proteins of the Rho/Rac family. While the β subunit is dedicated to farnesylation, the mammalian farnesyltransferase has a variety of substrates in addition to p21ras. The effect of inhibitors of the β subunit on the farnesylation of these other substrates, e.g., lamin proteins, transducin-γ and rhodopsin kinase, will be considered in the design and use of potential farnesyltransferase inhibitors.

It has not yet been demonstrated that the homologous mammalian gene will functionally substitute for yeast Ram1p, however, this can be formally tested using ram1 mutants and a vector expressing the mammalian gene encoding the β subunit of the farnesyltransferase. If the mammalian β subunit can function in place of Ram1p, test cells will be both viable (as a result of farnesylation of Ras) and competent for mating (as a result of farnesylation of a-factor).

If the mammalian gene encoding the β subunit of farnesyltransferase complements ram1, yeast would provide a test system for the discovery of potential inhibitors of mammalian farnesyltransferase. Specifically, MATa yeast tester cells could be exploited that: 1. carry the gene for the β subunit of mammalian farnesyltransferase in lieu of RAM1; 2. carry the cam mutation that renders the strains resistant to loss of Ras function in the presence of cAMP; 3. respond to a-factor which they export by virtue of heterologous expression of Ste3p; 4. respond to autocrine a-factor such that they cannot grow on media containing galactose. The latter characteristic will require expression of GAL1 under the control of a pheromone-responsive promoter and cells engineered to contain mutated GAL7 or GAL10 genes. Expression of GAL1 is toxic in the presence of galactose in strains which contain mutations in either the GAL7 or GAL10 genes. Signaling through the pheromone response pathway would render cells so engineered galactose-sensitive. Exposure of such strains to compounds which inhibit the β subunit of farnesyltransferase will confer upon these cells the ability to grow on media containing galactose and cAMP.

If the mammalian gene encoding the β subunit of farnesyltransferase (and all modified versions of the gene) fails to complement ram1, we may use the wild-type Ram1p as a surrogate target for potential effectors of mammalian farnesyltransferase. Specifically, we will use as tester cells MATa yeast strains that: 1. carry the cam mutation that renders the strains resistant to loss of RAS function in the presence of cAMP; 2. respond to a-factor which they export by virtue of heterologous expression of Ste3p; 3. respond to autocrine a-factor such that they cannot grow on media containing galactose. Exposure of such strains to compounds which inhibit the β subunit of farnesyltransferase will confer upon these cells the ability to grow on media containing galactose and cAMP.

In the strategies outlined above, it is desirable to discriminate inhibitors of farnesyltransferase from compounds that either directly block the negative response to a-factor, e.g. by interfering with the interaction of the Ste4–Ste18 complex with its effector, or by blocking the production of a-factor by a mechanism that does not involve farnesyltransferase. Controls would identify such false positives. Candidate agents will be tested on a MATa strain that is engineered to secrete α-factor and to respond to the secreted a-factor by failing to grow on galactose-containing media, as in the negative selection scheme outlined above. The strain will express wild type Ram1p. Any agent that enables these cells to grow on media containing galactose and cAMP will not be acting as an inhibitor of farnesyltransferase.

Candidate compounds which pass the foregoing test may act by targeting Ste14p, Ste6p, or other proteins involved in the maturation and export of a-factor, rather than farnesyltransferase. (Note, however, that compounds that inhibit processes critical to cell survival will not give rise to false positives. For example, since the protease responsible for the endoproteolytic removal of the C-terminal tripeptide of the a-factor precursor likely participates in the processing of Gg and members of the Rho/Rac family of proteins, inhibitors of this enzyme may not permit growth of the tester cells). Of the proteins involved in the production of a-factor, only the farnesyltransferase is also a major determinant of RAS function. Due to this effect, ram1 mutants are defective for growth at 30° C. and completely unable to grow at 37 (He B et al., Proc Natl Acad Sci 88: 11373–7, 1991). Tester cells (described above) can be grown in the presence of a candidate inhibitor on galactose-containing media±cAMP. If the test compound inhibits farnesyltransferase, cells will be capable of growth on galactose+cAMP but not on galactose in the absence of cAMP. This difference may be most obvious at 37°. If, on the other hand, the test compound inhibits other proteins involved in a-factor production, cells will grow on galactose-containing media regardless of the presence or absence of cAMP.

Compounds which pass the above tests are likely inhibitors of farnesyltransferase. This can be confirmed and their potencies determined with direct in vitro enzyme assays. Note that the strategies outlined will identify farnesyltransferase inhibitors which affect Ram1p. Agents which block Ram2p would likely fail to grow under all conditions. Indeed, ram2 null mutations are lethal (He B et al., Proc Natl Acad Sci 88: 11373–7, 1991), perhaps due to the fact that Ram2p also functions as a component of geranylgeranyltransferase I.

6.3 Carboxymethyltransferases

In yeast, methylation of the C-terminal amino acid of a-factor, Ras proteins, and presumably Rho/Rac proteins is catalyzed by Ste14p. Although MATa ste14 mutants are unable to mate, reflecting the requirement of carboxymethylation for the activity of a-factor, ste14 disruptions are not lethal and do not affect the rate of cell proliferation. Carboxymethylation appears to be dispensable for the function of Ras proteins and Ste18p (the yeast homologue of the Gγ subunit). Although Ras function in yeast can apparently tolerate the absence of carboxymethyl modification, it is nonetheless possible that inhibitors of mammalian methyltransferases could alter the activity of mammalian p21ras.

It could be determined if yeast ste14 mutations can be complemented by the homologous mammalian gene, or a modified version of it. One would use an episomal vector to express the mammalian gene encoding the methyltransferase in yeast that are genotypically ste14. The strain would be a modified MATa strain that expresses the a-factor receptor in lieu of the normal a-factor receptor and that contains an integrated fus1-HIS3 construct, so that the a-factor secreted by the cell confers autocrine growth on histidine-deficient media. If the mammalian methyltransferase can function in place of Ste14p, the tester cells will be capable of mating. That is, the mammalian methyltransferase will permit synthesis of active a-factor in ste14 mutants.

If the mammalian gene encoding the methyltransferase will complement ste14, tester strains can be constructed to test for potential inhibitors of mammalian methyltransferase. In one embodiment, tester MATa yeast strains will: 1. carry a mammalian carboxymethyltransferase gene in lieu of STE14; 2. respond to a-factor which they export by virtue of heterologous expression of Ste3p; 3. respond to autocrine a-factor such that they cannot grow on media containing galactose as in the negative GAL1 selection scheme outlined above. Exposure of such strains to compounds which inhibit the methyltransferase will confer upon these cells the ability to grow on media containing galactose.

It is desirable to discriminate inhibitors of carboxymethyltransferase activity from compounds that either directly block the negative response to a-factor, e.g. by interfering with the interaction of the Ste4–Ste18 complex with its effector, or block the production of a-factor by a mechanism that does not involve methyltransferase. The following control experiments will identify such false positives. Candidate inhibitors will be tested on a MATa strain that is engineered to secrete a-factor and to respond to the secreted a-factor by failing to grow on galactose-containing media. Any agent that enables these cells to grow on media containing galactose will be not be acting as an inhibitor of carboxymethyltransferase. Candidate compounds which pass the foregoing test may be targetting the carboxymethyltransferase, farnesyltransferase, Ste6p, or other proteins involved in the maturation and export of a-factor. In order to discriminate the target of the compounds, a combination of in vitro biochemical and in vivo genetic assays can be applied: both the carboxymethyltransferase and the farnesyltransferase can be assayed in vitro to test the effect of the candidate agent. Furthermore, if the target is Ste14p its overexpression on high-copy plasmids should confer resistance to the effect of the compound in vivo.

6.4 Proteases

Mature yeast α-factor is a thirteen amino acid peptide that is derived from a polyprotein precursor in much the same manner as mature mammalian melanocyte-stimulating hormone (MSH) or calcitonin are derived from precursor polyproteins. Two genes in the yeast genome encode prepro-α-factor, MFα1 and MFα2. MFα1 encodes a precursor polypeptide containing four copies of mature α-factor embedded in a polypeptide of the following structure: hydrophobic pre-sequence/hydrophilic pro-sequence/α-factor/α-factor/α-factor/α-factor. MFα2 encodes a polyprotein precursor of a similar structure containing only two copies of mature α-factor.

Pre-pro-α-factor is synthesized in the cytoplasm and is then transported from the cytoplasm to the endoplasmic reticulum and then to the Golgi along the classical secretory pathway of S. cerevisiae. The signal sequence of prepro-α-factor is cleaved during transit into the ER by signal peptidase and asparagine-linked oligosaccharides are added (in the ER) and modified (in the Golgi) on the pro-segment of the precursor as it transits the secretory pathway. Once in the Golgi, three distinct proteolytic processing events occur. First, the Kex2 protease cleaves at dibasic residues (-KR-) near the amino terminus of each α-factor repeat. Kex2 is homologous to the subtilisin-like endoproteases PC2 and PC1/PC3 involved in prohormone processing in mammalian cells (Smeekens and Steiner 1990; Nakayama et al. 1991). Additional mammalian Kex2-like processing endoproteases include PACE, isolated from a human hepatoma, PC4, expressed in testicular germ cells and PC6, a candidate protease for the processing of gastrointestinal peptides (Barr et al. 1991; Nakayama et al. 1992; Nakagawa et al. 1993). It appears that Kex2-like proteins comprise a large family of tissue-specific endoproteases in mammalian cells.

Once Kex2 has released the immature α-factor peptides, two additional proteases act to complete processing. Kex1 is a specific carboxypeptidase that removes the carboxy-terminal-KR remaining after cleavage by Kex2. Like its mammalian counterparts carboxypeptidases B and E, Kex1 is highly specific for peptide substrates with carboxy-terminal basic residues. The final proteolytic processing event that occurs is the removal of the spacer dipeptides at the amino terminus of each pro-α-factor peptide. This is accomplished by the product of the STE13 gene, dipeptidyl aminopeptidase A. This enzyme is a type IV dipeptidyl aminopeptidase: it is capable of cleaving on the carboxyl side of either -x-A- or -x-P- sites in vitro.

Other type IV dipeptidyl aminopeptidases are believed to be active in the processing of a variety of pre-peptides in animal cells (Kreil 1990). In addition, functional similarity has been proved between yeast Kex1 and Kex2 and their mammalian counterparts parts in that both yeast enzymes will proteolytically cleave endogenous precursors when expressed in mammalian cells deficient in the native enzyme (Thomas et al. 1988, 1990). It appears likely, then, that mammalian homologs of the yeast proteases Kex1, Kex2 and Ste13p, when expressed in yeast, will function to process a synthetic α-factor pheromone precursor bearing appropriate cleavage sites. Human proteases that may so function in yeast include PC2 and PC1/PC3 (or other Kex2 homologs), carboxypeptidases B and E (Kex1 homologs) and type IV dipeptidyl aminopeptidases (Ste13p homologs).

Yeast would provide a facile assay system for the discovery of inhibitors of proteases able to process synthetic α-factor. The yeast could be engineered to express both the potential inhibitor and the exogenous protease, and, preferably, not the latter's yeast cognate.

Furthermore, this means of exploiting yeast pheromone processing to identify protease inhibitors can be expanded to encompass any protease that can be expressed to function in yeast, provided an appropriate cleavage recognition site is included in a synthetic α-factor precursor. In the latter approach, novel proteolytic activities will be added to yeast; these enzymes will substitute for proteases in the α-factor maturation pathway but will not be "catalytic homologues" of Kex1, Kex2 or Ste13p. Production of mature α-factor will become dependent on the activity of the novel protease through removal of the recognition site(s) for a selected yeast enzyme from a synthetic MFα gene and insertion of the recognition sequence for the novel protease(s).

6.5 Exogenous ABC Transporters

The majority of proteins destined for transport to the extracellular environment proceed through a secretory pathway that includes translation initiation in the cytoplasm, transport to the lumen of the endoplasmic reticulum, passage through the Golgi to secretory vesicles and subsequent exit from cells. Other proteins leave the cell by an alternative mechanism, which involves mediation by an "ABC transporter". The ABC transporters form a family of evolutionarily conserved proteins, share a similar overall structure, and function in the transport of large and small molecules across cellular membranes (Higgins 1992). The characteristic component of members of this protein family is a highly conserved sequence that binds ATP (Higgins et al., 1986; Hyde et al. 1990); these intrinsic membrane proteins are ATPases, deriving energy from the hydrolysis of that nucleotide to effect the transport of molecules. This family includes over 50 prokaryotic and eukaryotic proteins: transporters of amino acids, sugars, oligosaccharides, ions, heavy metals, peptides, or other proteins belong to this superfamily. Representative transmembrane transporters are included in Table 1 of WO94/23025. Typically, ABC transporters use the energy of ATP hydrolysis to pump substrate across a cell membrane against a concentration gradient. Some import substrate, others export it. See Higgins, *Ann. Rev. Cell, Biol.,* 8: 67–113 (1992).

The prototypical structure of an ABC transporter includes four membrane-associated domains: two hydrophobic, putative membrane-spanning sequences, each predicted to traverse the membrane six times, and two nucleotide binding domains that couple ATP hydrolysis to transport. In prokaryotes, the domains of an ABC transporter are often present on separate polypeptides. Various permutations of domain fusions have been described: the *E. coli* iron hydroxamate transporter contains the two membrane-spanning domains in a single polypeptide and the ribose transporter of the same organism bears two nucleotide-binding domains on one molecule. The major histocompatibility complex (MHC) peptide transporter is composed of two polypeptides, Tap1 and Tap2. The N-terminus of each protein contains a hydrophobic membrane-spanning domain while the C-terminus contains an ATP-binding sequence. Together Tap1 and Tap2 form a functional complex. The heavy metal tolerance protein, HMT1, expressed in the fission yeast *Schizosaccharomyces pombe*, consists of a polypeptide containing a single hydrophobic domain and a C-terminal ATP-binding sequence (Ortiz et al. 1992). It may be that the HMT1 transporter functions as a homodimer. The *Saccharomyces cerevisiae* Ste6 a-factor transporter is expressed as a single polypeptide containing two membrane-spanning domains and two nucleotide-binding domains. When Ste6 is expressed as two half-molecules, the protein complex which apparently forms retains function at a level greater than 50% that of the wild type, single polypeptide (Berkower and Michaels 1991). In other eukaryotic ABC transporters, including Mdr1, CFTR and MRP, the four domains are also contained within a single polypeptide. Thus, the ABC transporter may be a single multidomain polypeptide, or it may comprise two or more polypeptides, each providing one or more domains.

In general, transporters contain six transmembrane segments per each hydrophobic domain, for a total of twelve segments. The minimum number of transmembrane segments required for formation of a translocation complex appears to be 10. Thus the histidine transporter of *S. typhimurium* lacks an N-terminal transmembrane segment from each of its hydrophophic domains and therefore contains five transmembrane segments per domain (Higgins et al., Nature 298, 723–727 (1982). The MalF protein of the *E. coli* maltose transporter contains an N-terminal extension of hydrophobic sequence which bears two additional transmembrane segments, bringing the total for this hydrophobic domain to 8 (Overduin et al. 1988). The N-terminal extension can be deleted, however, without loss of function of this transporter (Ehrmann et al. 1990). Although the number of segments required for formation of a functional translocator is suggested by these studies, there exists no data on the precise structure of the transmembrane segments themselves. These sequences are assumed to have an α-helical form, but this has not been proven and the structure of the entire translocation complex within the plasma membrane remains to be elucidated.

In order to span the lipid bilayer, a minimum of 20 amino acids is required and sequences believed to form transmembrane segments have been identified using hydrophobicity scales. Hydrophobicity scales assign values to individual amino acid residues indicating the degree of hydrophobicity of each molecule (Kyte and Doolittle 1982; Engleman et al. 1986). These values are based on experimental data (solubility measurements of amino acids in various solvents, analysis of side chains within soluble proteins) and theoretical considerations, and allow prediction of secondary structure in novel sequence with reasonable accuracy. Analysis using hydrophobicity measurements indicates those stretches of a protein sequence which have the hydrophobic properties consistent with a transmembrane helix.

With a few exceptions, there is little or no significant amino acid sequence similarity between the transmembrane domains of two different transporters. This lack of sequence similarity is not inconsistent with the apparent function of these hydrophobic domains. While these residues must be capable of forming the hydrophobic α-helical structures believed to transverse the plasma membrane, many amino acid residues are hydrophobic and can contribute to the formation of an α-helix.

Considerable, if as yet inexplicable, sequence similarity is has been detected in comparisons of the transmembrane domains of the yeast STE6, human MDR and *E. coli* HlyB hemolysin transporters [Gros et al., Cell 47, 371 (1986); McGrath and Varchavsky, Nature 340, 400 (1989); Kuchler et al., EMBO J. 8, 3973 (1989)]. Other sequence similarities can be explained by gene duplication, as in the case of the transmembrane domains of rodent P-glyco-proteins (Endicott et al. 1991). The transmembrane domain of the histidine transporter of *S. typhimurium* bears homology to that of the octopine uptake system of *Agrobacterium tumefaciens*, the latter two transporters translocate chemically similar substrates 21(Valdiva et al. 1991).

Study of mutant transport proteins has pointed to a role for the transmembrane sequences in the recognition of substrate. Thus maltose transporters in *E. coli* which gain the ability to translocate p-nitrophenyl-α-maltoside bear mutations in the transmembrane domain (Reyes et al. 1986). A mutation in transmembrane segment 11 of MDR has been shown to change the substrate specificity of that transporter (Gros et al. 1991) and mutation of charged residues in the transmembrane domain of CFTR changes its ion selectivity (Anderson et al. 1991).

Some aspects of the involvement of extramembrane loop sequences in transport function are being elucidated. In a number of bacterial transporters a short conserved motif is present on the cytoplasmic loop which connects transmembrane segments 4 and 5 [Dassa and Hofnung (1985)]. It has been hypothesized that this sequence interacts with the ATP-binding domains of these transport proteins; mutation of this conserved sequence will abolish transport function (Dassa 1990). Cytoplasmic loops may also be involved in substrate recognition. Thus the sequences following transmembrane segments 7 and 12 of the yeast a-factor transporter resemble sequences in the a-factor receptor, Ste3p, and may interact with the pheromone substrate (Kuchler et al. 1989). In fact, mutations in the cytoplasmic loops are known to alter the substrate specificity of a given transporter. The G185V mutation of human MDR, located in the loop between transmembrane segments 2 and 3, alters the interaction of that transporter with vinblastine and colchicine (Choi et al. 1988).

The ATP-binding domains are about 200 amino acids long, and domains from different transporters typically have a sequence identity of 30–50%. The conserved sequences include the "Walker motifs" which are associated with many nucleotide binding proteins. Walker, et al., *EMBO J.* 1: 945–951 (1982). Sequence conservation extends over the length of the ATP-binding domain, not being limited to the Walker motifs. Furthermore, the ATP-binding domains of a single transporter exhibit greater sequence identity to one another than to the domains from two different transporters. Not all proteins containing a conserved ATP-binding domain are involved in transport, however. The cytoplasmic enzyme UvrA functions in DNA repair and the EF-3 protein of yeast is an elongation factor. Yet both proteins contain ATP-binding cassettes identifiable by sequence comparison.

ATP-binding domains are highly hydrophilic and, in the case of transporters, appear to reside at the cytoplasmic face of the membrane, anchored there via an association with the membrane-spanning domain of these proteins. The points of interaction between the transmembrane and ATP-binding domains have not been experimentally determined. Models of the structure of the nucleotide binding domain indicate that loop sequences may extend from the core of the structure to interface with the hydrophilic sequences which transverse the membrane (Hyde et al. 1990; Mimura et al. 1991). The two structural models, one based on adenylate cyclase and the other on ras p21 structure, predict a core nucleotide binding fold composed of five β-sheets with the Walker A motif (a glycine-rich loop) positioned to interact with ATP during hydrolysis. In addition, loop structures (two loops in one model, one large loop in the other) are predicted to extend from the core to couple the ATP-binding domain to other domains of the transporter. The coupling sequences transmit, most likely through conformational change, the energy of ATP hydrolysis to those portions of the molecule which are involved in transport.

Ste6 function is required for mating but the protein is not necessary for yeast survival (Wilson and Herskowiz 1984; Kuchler et al. 1989; McGrath and Varshavsky 1989). Ste6 is structurally homologous to the mammalian MDRs. Furthermore, it has been demonstrated that two mammalian MDR proteins, murine Mdr3 and human Mdr1, will substitute functionally for the yeast transporter in cells deleted for STE6 (Raymond et al. 1992; Kuchler and Thorner 1992). Yeast strains deleted for STE6 serve as a starting point for the design of screens to discover compounds that modulate the function of exogenous ABC transporters.

Two different yeast screens can be used to identify modulators of ABC transporter function. In the first instance, a mammalian protein that transports a-factor will serve as a target for potential inhibitors of transporter function. Thus, a yeast strain will be engineered to express a functional transporter, e.g. mammalian MDR1, which substitutes for the yeast Ste6 protein in the transport of a-factor. Furthermore, this strain will be engineered to respond in autocrine fashion to a-factor: e.g., so that the cells will be unable to grow on media containing galactose. This negative selection will depend on the expression of the GAL1 gene under the control of a pheromone-responsive promoter in a strain background which includes mutated versions of the GAL7 or GAL10 genes. Expression of GAL1 in the presence of galactose in such a strain background is toxic to cells. In the absence of a-factor transport, signaling down the pheromone response pathway would cease as would the consequent expression of the toxic gene. Cell growth in the presence of a test compound, or upon expression of a specific random peptide, would signal inhibition of transport function and the identification of a potential therapeutic.

In addition to inhibitors of MDR, compounds may be identified which interfere with the interaction of a-factor with the a-factor receptor. Such compounds can be discriminated by their inhibition of a-factor-induced growth arrest in a wild type Matα strain. Compounds may also impact at other points along the pheromone response pathway to inhibit signaling and these compounds will prevent signal transduction in a wild type Matα strain.

In a second screen, a mutant heterologous transporter (e.g., mutant CFTR) that is initially incapable of transporting a-factor or an a-factor-like peptide can be expressed in autocrine yeast deleted for endogenous Ste6. The cells will be capable of an autocrine response to the a-factor which those cells produce. Thus a pheromone-responsive promoter will control expression of a gene that confers an ability to grow in selective media. Such cells will permit identification of compounds which correct defects in the transporter and permit it to function in the export of pheromone analogues to the extracellular space. In this way, therapeutic peptides or other classes of chemical compounds could be identified which stabilize a mutant protein and allow normal processing, transport, localization to the plasma membrane and function. This strategy, if successful, may eliminate the need to "replace" some mutant genes with normal sequence, as envisioned in gene therapies, by recovering the function of mutant proteins through the correction of processing and/or localization defects.

In addition to "activators" of the mutant transporter, compounds may also be identified which are capable of initiating signalling from the a-factor receptor in the absence of transport by the endogenously expressed pheromone. These compounds will be distinguished by their ability to cause growth arrest in a wild type Matα strain. Compounds may also impact at other points along the pheromone pathway and can be discerned via an ability to initiate signalling in a wild type Matα strain in the absence of a-factor.

In a preferred embodiment, the exogenous protein produced by the yeast cells is one of the exogenous ABC transporters listed in Table 1 of WO94/23025.

7. Gene Expression in Yeast

7.1 Regulatory Sequences

The expression of a peptide-encoding gene in a yeast cell requires a promoter which is functional in yeast. Suitable promoters include the promoters for metallothionein, 3-phosphoglycerate kinase (Hitzeman et al., J. Biol. Chem. 255, 2073 (1980) or other glycolytic enzymes (Hess et al., J. Adv. Enzyme Req. 7, 149 (1968); and Holland et al.

*Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73, 657. Other promoters, which have the additional advantage of transcription controlled by growth conditions, are the promoter regions for alcohol dehydrogenase 2, isocytochrome C, CUP1 (inducible by copper), acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 and the GPA1 promoter are of particular interest.

In constructing suitable expression plasmids, the termination sequences associated with these genes, or with other genes that are efficiently expressed in yeast, may also be ligated into the expression vector 3' of the heterologous coding sequences to provide polyadenylation and termination of the mRNA.

7.2 Structural Sequences

The structural gene encoding the adenylyl cyclase may be the wild-type mammalian gene, or a modified gene. "Silent" modifications may be made to improve expression, by, e.g., (1) eliminating secondary structures in the corresponding mRNA, or (2) substituting codons preferred by yeast for codons that are not so preferred, or to facilitate cloning, e.g., by introducing, deleting or modifying restriction sites. The gene may also be modified so that a mutant adenylyl cyclase is encoded.

Analysis of yeast codon usage indicates that there exists a preferred codon set consisting of the most abundant isoaccepting tRNAs present in yeast and that this preferred set (25 out of the 61 possible coding triplets) is the same for all yeast proteins (Bennetzen and Hall (1981) J. Biol. Chem. 257, 3026–3031). The rapid translation rate required for abundant proteins is believed to provide the selective pressure for the existence of the preferred set of codons. As the extent of biased codon usage in specific genes correlates directly with the level of gene expression (Hoekma et al. (1987) Mol. Cell. Biol. 7, 2914–2924), experimental strategies aimed at the expression of heterologous genes in yeast exploit the codon bias that has been described for that organism (Sharp et al. (1986) Nuc. Acids Res. 14, 5125–5143).

In engineering the sequences with which to express mammalian adenylyl cyclase in *Saccharomyces cerevisiae*, a chimeric coding sequence was constructed. The initial 27 codons of the rat type 2 adenylyl cyclase are contributed by an oligonucleotide that was inserted into the expression vector, while the remainder of the coding sequence, beginning with codon 28, was derived from the cDNA clone obtained from rat brain. By means of the oligonucleotide, codon usage at the N-terminus of the enzyme was altered to optimize translation of the sequence in yeast.

7.3 Vectors

The vector must be capable of replication in a yeast cell. It may be a DNA which is integrated into the host genome, and thereafter is replicated as a part of the chromosomal DNA, or it may be DNA which replicates autonomously, as in the case of a plasmid. In the latter case, the vector must include an origin of autononomous replication that is functional in the host. There are two types of yeast origins of replication in common use: those derived from the yeast 2 micron circle which permit replication of plasmids to 40–50 copies per yeast cell; and those derived from genomic CEN ARS sequences, which are maintained at lower copy number, typically only one or two plasmids per yeast cell. In the case of an integrating vector, the vector may include sequences that facilitate integration, e.g., sequences homologous to host sequences, or encoding integrases.

Besides being capable of replication in yeast cells, it is convenient if the vector can also be replicated in bacterial cells, as many genetic manipulations are more conveniently carried out therein. Shuttle vectors capable of replication in both yeast and bacterial cells include YEps, YIps, and the pRS series.

7.4 Host Cells

The yeast may be of any species that require cyclic AMP for growth and which are cultivatable. Suitable species include *Kluyverei lactis, Schizosaccharomyces pombe*, and *Ustilago maydis; Saccharomyces cerevisiae* is preferred. The term "yeast", as used herein, includes not only yeast in a strictly taxonomic sense (i.e., unicellular organisms), but also yeast-like multicellular fungi.

The host cell may be a diploid a/α or a haploid cell. Preferably, to eliminate, in the first instance, any possible effects of the yeast G proteins on the mammalian cyclase, a diploid strain is used. Diploid yeast cells, in contrast to haploid cells, do not express GPA1, which encodes the yeast homolog of Gα, nor do they express STE4 or STE18, which encode yeast Gβ and Gγ, respectively.

In addition, crosses are preferably made to derive a diploid strain that bears a mutant allele of yeast adenylyl cyclase, cdc35-1, as the endogenous cyclase.

The yeast cell is preferably of a cAMP dependent strain such as the cam1, cam2, cam3 strain.

EXAMPLES

Yeast require the catalytic activity of the enzyme adenylyl cyclase to grow. There exists a mutant form of the *Sacchaaromyces cerevisiae* adenylyl cyclase encoded by the mutant allele cdc35-1. The cdc35-1 mutation describes a temperature sensitive cell division cycle mutant (Casperson et al. (1985) Proc. Natl. Acad. Sci. USA 82, 5060–5063). This mutation results in a phenotype resembling that of temperature-sensitive cyr1-1 mutants which bear an alteration in the yeast adenylate cyclase. Haploids bearing cdc35-1 growth arrest at G1, as unbudded cells, at temperatures above 30° C. Diploids homozygous for cdc35-1 sporulate in rich medium, in nutrient conditions that prevent sporulation of wild-type yeast cells (Shilo et al. (1978) Exp. Cell Res. 112, 241–248). The cdc35-1 mutation can be complemented by sequence encoding yeast CYR1 or the cells can be rescued from growth arrest by the addition of exogenous cAMP, provided the cells also exhibit the cam phenotype. cdc35-1 maps to the same locus as does cyr1-1 (Boutelet and Hilger 1980). Extracts of cdc35-1 cells that have been growth arrested at the restrictive temperature exhibit in vitro adenylyl cyclase activity approximately equal to that of wild type cells incubated at room temperature. These data suggest that the cdc35-1 mutation affects a portion of the adenylyl cyclase molecule outside of the catalytic site, perhaps in sequence involved in the interaction between the cyclase and co-factors or regulatory molecules.

A diploid strain (CY1106) bearing this mutant allele (genotype: MATa/MATα cdc35-1/cdc35-1 cam/(cam?) ura3-52/ura3-52 leu2-3,112/leu2 trp1/trp1 his7/+) was transformed with plasmids containing sequences encoding rat type 2 adenylyl cyclase and rat Gαs. Expression of the rat adenylyl cyclase was constitutive and that of Gαs was inducible by copper. This strain grew at 34° C. in the presence, but not in the absence, of copper. Similar strains, in which only the rat adenylyl cyclase-encoding plasmid or only the rat Gαs-encoding plasmid were present and expressed, failed to grow at 34° C. This experiment demonstrated that, in the presence of mammalian Gαs, type 2 rat adenylyl cyclase enables the growth at 34° C. of yeast harboring the mutant adenylyl cyclase encoded by cdc35-1.

This experiment is described in more detail below.

1. Construction of adenylyl cyclase expression plasmid

In order to obtain a plasmid expressing rat type II adenylyl cyclase, we used a yeast expression plasmid that we had previously constructed and that is based on YEp51 (Broach et al. (1983) in "Experimental Manipulation of Gene Expression" (M. Inouye, ed.) pp. 83–117, Academic Press, NY, 1983. Salient features of this vector (Cadus 1284) are the following: first, it contains the replication determinant of the yeast 2μ circle plasmid; this permits the plasmid to replicate to high copy number in yeast (typically 10 to 40 copies per cell). It also contains a yeast gene which permits selection for the presence of the plasmid in yeast that lack a functional genomic copy of the same gene; specifically, in the absence of the amino acid leucine, leu2 yeast which carry the vector will grow while those cells lacking the vector will not. Finally, in lieu of the GAL10 promoter sequences present in the parental Yep51, Cadus 1284 contains the promoter sequences of the yeast phosphoglycerol kinase (PGK) gene. NcoI and BamHI restriction enzyme sites that permit the insertion of genes to be expressed from the plasmid are present downstream of this constitutively active promoter.

An oligonucleotide of approximately 100 base pairs was inserted into the NcoI- and BamHI-restricted vector, Cadus 1284. This oligonucleotide encodes the first 27 amino acids of rat cyclase with codon usage which favors translation in yeast. The oligonucleotide was constructed using the following single stranded oligonucleotides:

```
oligo 066:  5'GCCGTCTCACATGAGAAGAAGAAGATACTTGAGAGATAGAGCTGAAGCTGCTGCA 3'  (SEQ ID No: 2)
oligo 069:  5'GCAGCTTCAGCTCTATCTCTCAAGTATCTTCTTCTTCTCATGTGAGACGGC 3'  (SEQ ID No: 3)
oligo 070:  5'GCTGCTGCTGCTGGTGGTGGTGAAGGTTTGCAAAGATCCCGG 3'  (SEQ ID No: 4)
oligo 071:  5'GATCCCGGGATCTTTGCAAACCTTCACCACCACCAGCAGCAGCAGCTGCA 3'  (SEQ ID No: 5)
```

Oligo 066 was annealed to phosphorylated oligo 069; oligo 071 was annealed to phosphorylated oligo 070. The two double-stranded oligonucleotides were mixed, ligated, digested with EspI, and the resulting approximately 92 base pair oligonucleotide was gel purified and ligated to NcoI- and BamHI-digested Cadus 1284. The resulting modified vector, Cadus 1464, contains a unique XmaI site that overlaps the BamHI site and is contributed by the oligonucleotide.

The gene encoding type 2 adenylyl cyclase from rat brain was obtained from Randall R. Reed (Johns Hopkins School of Medicine) as a 6.4 kilobase plasmid clone that contains XmaI sites 80 bases downstream of the start codon and approximately 220 base pairs downstream of the cyclase stop codon (Feinstein et al. (1991) Proc. Natl. Acad. Sci. USA 88, 10173–10177). These restriction enzyme sites were used to isolate a 3.4 kilobase fragment that contains nearly the entire coding region of the cyclase, beginning at codon 28 and continuing through the stop codon. When this fragment is ligated into the XmaI site of the modified vector described above, a chimeric cyclase gene is created, wherein the initial 27 codons are contributed by the oligonucleotide present in the vector and the remaining codons are contributed by the authentic rat adenylyl cyclase type 2 gene sequence. The consequences of this strategy for the construction of the cyclase expression plasmid include the following: 1. The N-terminal 27 amino acids encoded by the chimeric cyclase gene are identical to those encoded by the native rat gene, but the triplets encoding these amino acids are those that are efficiently translated in yeast; 2. The chimeric cyclase gene is expressed under the control of the PGK promoter which has high, constitutive activity; 3. The cyclase gene will be in high copy number in yeast cells.

2. Construction of Gαs Expression Plasmid

The plasmid used to express Gαs contains a full-length rat Gαs cDNA under the control of the copper-inducible yeast promoter, CUP1 (plasmid described in Kang et al. Mol. Cell. Biol. 10: 2582–2590, 1990). Expression of Gαs was induced by plating yeast bearing this plasmid on solid media containing 100 μM copper sulfate.

3. Derivation of Yeast Strain

The strain used to test the activity of mammalian adenylyl cyclase in yeast was a diploid strain generated from a haploid strain of genotype MATa cdc35-1 cam leu2 trp1 ura3 his7 (Y1777). Y1777, bearing the mutant cdc35-1 allele, was obtained from the laboratory of J. R. Broach at Princeton University. Y1777 was crossed with CY5 (genotype MATα ura3 lys2 ade2 his3 leu2), the resulting diploids were sporulated, and haploid progeny of genotype MATα cdc35-1 (cam?) ura3 trp1 leu2 were selected for mating with Y1777 to generate the diploid strain CY1106 (genotype cdc35-1/cdc35-1 cam/(cam?) ura3-52/ura3-52 leu2-3,112/leu/2 trp1/trp1 his7/+). CY1106, like the haploids from which it was generated, is capable of growth at room temperature but does not grow at 30° C. or at higher temperatures due to the temperature sensitivity of the endogenous yeast adenylyl cyclase encoded by the cdc35-1 mutant allele.

The diploid strain CY1106 was transformed with the following pairs of plasmids: (1) PGK promoter-driven rat adenylyl cyclase expression plasmid (Cadus 1470) and CUP1 promoter-driven rat Gαs expression plasmid (Cadus 1284) and CUP1 promoter-driven rat Gαs expression plasmid (Cadus 1046) to yield strain CY1251; (2) PGK promoter-driven expression plasmid lacking adenylyl cyclase sequence (Cadus 1046) to yield strain CY 1248; (3) PGK promoter-driven adenylyl cyclase expression plasmid (Cadus 1470) and CUP1-driven expression plasmid lacking Gαs (Cadus 1136) yielding CY 1249; (4) PGK promoter-driven expression plasmid lacking adenylyl cyclase sequence (Cadus 1284) and CUP1-driven expression plasmid lacking Gαs sequence (Cadus 1136) yielding CY 1246. The four types of double transformants, CY 1251, CY 1248, CY 1249 and CY 1246, (genotype MATa/MATα cdc35-1/cdc35-1 cam/(cam?) ura3-52/ura3-52 leu2-3,112/leu2 trp1/trp1 his7/+), each carrying a high-copy LEU2-marked plasmid containing a PGK promoter and a high-copy TRP1-marked plasmid containing a CUP1 promoter, were plated onto synthetic solid media which lacked leucine and tryptophan±100 μM CuSO$_4$. Plates were incubated for three days at RT, 30° C., 34° C., and at 37° C.

At RT and at 30° C., the four strains grew at approximately the same robust rate both in the presence and in the absence of copper, reflecting the activity of the endogenous yeast adenylyl cyclase encoded by the cdc35-1 allele.

At 34° C. in the absence of copper, all four strains failed to grow. But at 34° C., in the presence of copper sulfate, CY1251 (containing the constitutively expressed mammalian adenylyl cyclase and the copper-inducible mammalian Gαs) grew rapidly while other strains failed to grow. Thus, at 34° C. the mammalian adenylyl cyclase could compensate for the inactive, mutant yeast adenylyl cyclase, provided that mammalian Gαs was also expressed.

At 37° C. all four strains showed little growth in the presence of copper, likely due to the poor viability of yeast at this temperature.

4. Expression of Mammalian Adenylyl Cyclase in Haploid Yeast Cells

Our initial result of functional expression of a mammalian adenylyl cyclase in yeast was obtained using diploid cells (genotype MATa/MATα cdc35-1/cdc35-1 cam/(cam?) ura3-52/ura3-52 leu2-3,112/leu2 trp1/trp1 his7/+). To determine if similar results would be obtained in haploid yeast, we transformed haploid cells of genotype MATa cdc35-1 cam ura3-52 leu2-3,112 trp1 his7 and MATα cdc35-1 cam ura3-52 leu2-3,112 trp1 his7 with the identical plasmids used to transform diploid cells: one containing a copper-inducible rat Gαs gene and a second containing a constitutively expressed rat type 2 adenylyl cyclase. Provided that Gαs was expressed, the rat adenylyl cyclase was able to rescue growth of each haploid strain at 34° C. Minor differences in results obtained with diploid cells and haploid cells were observed, however. Gαs-stimulated growth at 34° C. was slightly greater and growth in the absence of Gαs at 34° C. was slightly lower (i.e. there was lower background growth of cells) in diploids expressing the rat adenylyl cyclase.

5. Expression of Mammalian Adenylyl Cyclase from Low Copy Plasmids

Initial results were obtained with the expression of rat type 2 adenylyl cyclase from a high copy plasmid that is typically present at 10 to 40 copies per cell. In order to determine if the same phenotype would be observed if the gene encoding rat adenylyl cyclase was present at only one or two copies per yeast cell, we utilized a low copy plasmid to express the rat cyclase. Yeast harboring the cdc35-1 allele were transformed with a low copy plasmid encoding the type 2 adenylyl cyclase. Specifically, sequence encoding rat type 2 adenylyl cyclase under the control of the constitutive PGK promoter was moved from a LEU2-containing high copy-plasmid to an equivalent low-copy plasmid. This low-copy plasmid and appropriate negative controls were transformed into both haploid and homozygous diploid cdc35-1 yeast containing the rat Gαs gene under the control of the copper-inducible CUP1 promoter. When both Gαs and rat adenylyl cyclase are expressed in these cells, the cells acquire an ability to grow at 34° C. These results demonstrate that cyclase activity sufficient for the growth of cells is obtained when the adenylyl cyclase gene is present on plasmids that replicate at one to two copies per cell. This result was obtained in both haploid and diploid yeast.

6. Expression of Rat Adenylyl Cyclase from an Integrated Sequence

The results obtained using low copy plasmids suggest that rat adenylyl cyclase will likely rescue growth at 34° C. in cdc35-1 yeast in which the cyclase gene is integrated into the yeast genome. It is preferable to have the cyclase expressed from an integrated copy of the gene rather than from extrachromosomal plasmids: genes are more stable when integrated and integration frees the selectable LEU2 marker for use on another plasmid that we might wish to introduce in subsequent experiments. We will direct the gene encoding the rat type 2 cyclase into the lys2 locus of strain CY732 (genotype MATa cdc35-1 cam lys2 leu2 trp1 ura3) using an integrating plasmid marked with URA3 and containing the rat adenylyl cyclase gene inserted into the LYS2 gene. CY732 will be transformed with this plasmid, and URA+ transformants will be selected and grown in the presence of 5-fluoroorotic acid (FOA) to select for the loss of URA3. Colonies that grow on FOA will be picked, transformed with a plasmid encoding Gαs, and tested for an ability to grow at 34° C. Those yeast exhibiting Gαs-dependent growth at 34° C. should bear the rat adenylyl cyclase gene integrated at the LYS2 locus. Their genotype will be designated MATa cdc35-1 cam lys2::AC2 leu2 trp1 ura3.

7. Screen for Activators and Inhibitors of Type 2 Adenylyl Cyclase

Yeast bearing cdc35-1 and expressing rat type 2 adenylyl cyclase can be used to screen for agents that stimulate the mammalian cyclase since activators of the latter protein will promote the growth of yeast at 34° C. (Accordingly, rat Gαs is an example of an activator of adenylyl cyclase.) Specifically, haploid yeast that carry cdc35-1 and an integrated copy of rat type 2 adenylyl cyclase (genotype MATa cdc35-1 cam lys2::ACII leu2 trp1 ura3) will be used to screen libraries of natural or synthetic compounds to identify candidate activators of the mammalian adenylyl cyclase. Candidates will be capable of stimulating growth of the test strain at 34° C., but incapable of stimulating growth of the parental strain lacking the rat adenylyl cyclase gene (genotype MATa cdc35-1 cam lys2 leu2 trp1 ura3). As an extension of this approach, we will transform the test strain with a library of URA3-containing plasmids that encode peptides of random sequence. The transformants will be plated on uracil-deficient media and incubated at 34° C. Cells that express peptides that activate the mammalian adenylyl cyclase will form colonies due to "autocrine" stimulation of that enzyme. These peptides can be identified by isolating the peptide-encoding plasmids and sequencing the region that encodes the random peptide. Candidate activators of the mammalian adenylyl cyclase will be further tested in an in vitro biochemical screen with purified enzyme in order to confirm direct stimulation of the cyclase.

Haploid cdc35-1 yeast bearing an integrated copy of rat type 2 adenylyl cyclase, and a plasmid encoding Gαs can be used in primary screens for inhibitors of the mammalian cyclase. Agents that reduce Gαs-dependent growth at 34° C. will be considered candidate inhibitors of the cyclase and will be tested in a secondary biochemical screen using purified enzyme. This secondary screen will discriminate between agents that directly inhibit type 2 adenylyl cyclase and those that act indirectly, for example by interfering with the ability of Gαs to stimulate the mammalian cyclase. Note that compounds that act by blocking the interaction of Gαs with adenylyl cyclase are, in their own right, of interest and will be characterized independently.

8. Expression of Mammalian Gαi in Yeast

While Gαs can stimulate all known forms of adenylyl cyclase, type 1, type 5 and type 6 adenylyl cyclase have been shown to be inhibited directly by Gαi-1 [Taussig et al (1994)]. Haploid yeast that carry cdc35-1, an integrated copy of type 5 adenylyl cyclase, and a plasmid encoding Gαs will be transformed with a high-copy plasmid that encodes, for example, Gαi-1. Yeast expressing the Gαi gene would be expected to grow more slowly at 34° C. than the parental strain which lacks Gαi-1, due to the inhibitory effect of the Gαi-1 subunit. If this proves to be the case, we will use this strain, expressing mammalian adenylyl cyclase, Gαs, and Gαi-1, as a test strain to screen for compounds that interfere with the inhibition of cyclase by Gαi-1.

Compounds that stimulate growth of the test strain at 34° C. may be exerting this effect by blocking the interaction of Gαi-1 and adenylyl cyclase. However, the same growth-stimulatory effect would also be exhibited by compounds that directly activate adenylyl cyclase, enhance the stimulatory effect of Gαs on adenylyl cyclase, activate a downstream component whose activity was dependent on cAMP production, etc. To distinguish the growth-stimulating compounds that directly affect the inhibitory influence of Gαi-1 on adenylyl cyclase from those that act elsewhere, all candidate compounds will be tested on a battery of isogenic control strains. One control strain will lack Gαi-1 (yet contain type 5 adenylyl cyclase and Gαs); compounds that accelerate the growth of this strain or enable its growth over a wider range of temperatures will be considered to affect targets other than Gαi-1. Other control strains will be those without adenylyl cyclase type 5 or without Gαs or without both adenylyl cyclase and Gαs. Compounds that stimulate the growth of any of these control strains will be excluded as inhibitors of the interaction between Gαi-1 and adenylyl cyclase. Note that these control tests can lead to the identification of compounds that directly stimulate adenylyl cyclase or promote the stimulatory effect of Gαs on adenylyl cyclase.

9. Expression of Activated Mammalian Gαs in Yeast

The Gαs subunit exists in either of two forms, designated Gαs-GTP and Gαs-GDP. Under the conditions of our experiments, the predominant form of mammalian Gαs in yeast is expected to be Gαs-GDP. We attribute the ability of Gαs to stimulate rat type 2 adenylyl cyclase in yeast to the presence of a relatively small pool of the GTP-bound form. As there may be experimental situations in which it is desirable that a larger pool of the activating species is available to stimulate adenylyl cyclase activity, we will exploit a constitutively active, mutant form of Gαs. Haploid and diploid yeast of genotypes MATa cdc35-1 cam lys2 leu2 trp1 ura3 and MATa/MATα cdc35-1/cdc35-1 cam/(cam?) ura3-52/ura3-52 leu2-3,112/leu2 trp1/trp1 his7/+, respectively, will be transformed with the following two plasmids: a low-copy, LEU2-containing plasmid that encodes rat type 2 adenylyl cyclase driven by the PGK promoter and a high-copy, TRP1-containing plasmid that uses the CUP1 promoter to direct expression of a mutant Gαs that is predominantly, if not exclusively, in the Gαs-GTP form. This activated form of Gαs (Gαs$_{Q227L}$), which we have generated by conventional oligonucleotide-directed mutagenesis of the wild-type Gαs allele, was identified as a GTPase-inhibiting mutation that results in constitutive activation of Gαs and persistent stimulation of adenylyl cyclase in pituitary adenomas (Landis et al. (1989) Nature 340, 692–696). This mutation causes a 95% decrease in GTPase activity and the mutant Gαs therefore exists predominantly in the GTP-bound form. In a strain co-expressing the rat adenylyl cyclase and the mutant Gαs, we expect to observe greater adenylyl cyclase activity exhibited by more rapid growth at 34° C., greater temperature range of growth, or greater sensitivity to the inductive effects of copper.

10. Expression of Mammalian Gβγ Subunits in Yeast

In addition to expressing mammalian Gα subunits, yeast will be engineered to express specific mammalian Gβγ combinations. Coincident expression of mammalian Gαs or Gαi, Gβ, and Gγ subunits in yeast will result in the reconstitution of mammalian heterotrimeric G proteins in yeast. In mammalian cells, these heterotrimeric G proteins couple a subset of seven-transmembrane receptors to adenylyl cyclase, causing the stimulation or inhibition of that enzyme. Therefore, expression in yeast of an appropriate G protein-coupled receptor and adenylyl cyclase, together with the components of a heterotrimeric G protein will duplicate a complete mammalian signal transduction pathway in that organism. Upon reconstitution of this pathway in appropriate strains, agents that activate or inhibit the seven-transmembrane receptor will influence cAMP-dependent growth of the yeast at 34° C. In addition, through appropriate choice of the particular isoforms of adenylyl cyclase, Gβ, and Gγ that are expressed in yeast, agents that affect the function of various Gβγ dimers will affect cAMP-dependent growth at 34° C.

Judicious choice of the Gβ and Gγ subtypes that are expressed in yeast will influence the utility of the strains that express mammalian adenylyl cyclase. While Gβ1 and Gγ1 can form a functional complex that binds Gαs, the β1γ1 dimer exhibits little ability to activate type 2 adenylyl cyclase in the presence of Gαs (J Biol Chem 267: 23407, 1992). We therefore expect that expression of β1 and γ1 in yeast that simultaneously express both mammalian Gαs and type 2 adenylyl cyclase would, by forming a complex with Gαs, lower the production of cAMP by the cyclase by preventing the stimulation of the cyclase by Gαs. This, in turn, should be reflected in slower growth of the yeast when compared with the growth that occurs upon expression of Gαs and the cyclase alone. Thus, slower growth of yeast simultaneously expressing the three mammalian G protein subunits and type 2 adenylyl cyclase will indicate that the mammalian G proteins form a heterotrimer in yeast. This result would provide a yeast strain in which functional, mammalian heterotrimeric G proteins can be studied.

Gβ1 and Gγ1 will be amplified by the polymerase chain reaction using as templates plasmids obtained from Dr. Mel Simon at Cal Tech. These plasmids contain the bovine genes encoding Gβ1 (Fong et al. (1986) Proc. Natl. Acad. Sci. USA 83, 2162–2166) and Gγ1 (Hurley et al. (1985) Proc. Natl. Acad. Sci. USA 81, 6948–6952). Each of the two amplified products will be cloned into high-copy number plasmids marked with URA3 and LEU2. In these plasmids expression will be controlled by the copper-inducible CUP1 promoter. Haploid cdc35-1 yeast bearing the rat type 2 adenylyl cyclase gene integrated at the LYS2 locus and expressing mammalian Gαs under the control of the GPA1 promoter. (which is constitutively active in haploid cells) from a TRP1-marked high-copy plasmid will be transformed with the high-copy plasmids containing Gβ and Gγ marked with URA3 and LEU2, respectively. Thus, the yeast will carry three plasmids, each expressing a unique selectable marker and a mammalian G protein subunit. These yeast should grow at 34° C. in the absence of copper due to stimulation of rat type 2 adenylyl cyclase by Gαs. Addition of copper to the growth medium will boost expression of Gβ and Gγ and should thereby inhibit growth as the Gβγ dimer complexes Gαs and prevent stimulation of the cyclase by the alpha subunit.

Upon demonstration that mammalian Gα, Gβ, and Gγ can form heterotrimers in yeast, we will construct yeast strains whose growth is extremely sensitive to the degree of association of the βγ dimer with Gαs. It has been documented that, in vitro, Gβ1 and Gγ2 form functional complexes that bind to Gαs. But, in contrast to the β1γ1 complex, β1γ2 acts synergistically with Gαs to activate type 2 adenylyl cyclase (Iñiguez-Lluhi et al. (1992) J. Biol. Chem. 267, 23407–23417). That is, the ability of free Gαs to stimulate type 2 cyclase is enhanced by free β1γ2 dimer. Note that expression of equal levels of mammalian Gαs, Gβ1, and Gγ2 in yeast that also express type 2 adenylyl cyclase should result in little cyclase activity due to the formation of the heterotrimeric G protein. But these yeast are poised to exhibit greatly enhanced adenylyl cyclase activity, and therefore growth at 34° C., in response to interventions that dissociate Gαs and Gβγ. For example, these yeast will be extremely sensitive to compounds that interfere with the association of Gαs and βγ.

Yeast of genotype MATa cdc35-1 cam lys2::ACII leu2 trp1 ura3 will be transformed with the following three high-copy number plasmids:
1. a TRP1-marked plasmid with the mammalian Gαs under the control of the CUP1 promoter;
2. a LEU2-marked plasmid with the mammalian Gβ1 under the control of the GPA1 promoter;
3. a URA3-marked plasmid with the mammalian Gγ2 under the control of the GPA1 promoter. Induction of Gαs expression with $CuSO_4$ should not enable cells to grow at 34° C. due to the binding of Gαs by Gβγ. If, however, growth at 34° C. is stimulated by copper, we will presume that there is an excess of Gαs subunits relative to Gβγ. Accordingly, we will reduce expression of Gαs by lowering the concentration of copper in the medium until no growth is observed. (Parallel titrations of a control strain lacking Gβ1 and Gγ2 with $CuSO_4$ will be conducted to confirm that this concentration of $CuSO_4$ can induce expression of sufficient Gαs to induce growth at 34° C. in the absence of Gβ1 and Gγ2.) At this copper concentration there should be approximately equimolar intracellular concentrations of the three mammalian G protein subunits. While this strain will be unable to grow at 34° C. in the presence of this critical concentration of copper, growth should be extremely sensitive to agents that dissociate α from βγ. Accordingly, this strain will be further engineered to express mammalian seven-transmembrane receptors, such that activation of these receptors at the critical copper concentration results in the growth of the strain at 34° C.

Low copy and integrated ACII can rescue growth of cdc35-1 strains.

We have, for the reasons specified above, integrated rat AC2 (adenylyl cyclase 2) into the yeast genome. The plasmid directing integration of AC2 was constructed by cloning the PGK promoter-driven AC2 into a vector (Cadus 1294; genotype CmR 'lys2 lys2') that directed integration of the PGKp-AC2 into the LYS2 locus of strain CY1789 (genotype MATa tbt1-1 cdc35-1 ura3 his3 trp1 leu2 (cam?). Specifically, PGKp-AC2 was excised from Cadus plasmid 1512 as a 4.4 kb EcoRI-to-BglII fragment, the BglII site was blunt-ended, and the fragment was cloned into the EcoRI and Sma I sites in the polylinker of Cadus plasmid 1294. The resulting construct (Cadus plasmid 1633) was linearized at the unique Bgl II site, and strain CY1789 was transformed with the linearized DNA. Since this targeted integration of AC2 disrupts wild-type LYS2, integrants were selected on plates containing (α-aminoadipate (2 g/l), a compound that confers a growth advantage to yeast lacking fully functional LYS2 (Chatoo et al, Genetics 93: 51, 1979). One such integrant, CY1936 (genotype MATa lys2::PGKp-ACII tbt1-1 cdc35-1 ura3 his3 trp1 leu2 (cam?), was transformed with a plasmid encoding rat Gαs whose expression is under the control of the copper-inducible CUP1 promoter. The resulting strain exhibited growth at 34° C. in the presence of 100 μM $CuSO_4$, reflecting the ability of the integrated AC2 to complement the temperature-sensitive cdc35-1 allele, provided that Gαs is also expressed. An isogenic diploid strain was made from CY1936, and this strain was also shown to express functional rat AC2, as demonstrated by its ability to grow at the restrictive temperature as long as Gαs was coexpressed.

ACIV confers temperature resistance to cdc35-1 strains in a Gαs -dependent manner, both episomally and integrated.

A cDNA encoding rat type 4 adenylyl cyclase was provided by Dr. Al Gilman of the University of Texas Southwestern Medical Center. We constructed a plasmid for expressing AC4 in yeast by subcloning the 3.2 kb SpeI to BglII fragment, which contained all but the 14 N-terminal amino acids of AC4 open reading frame, into a LEU-marked 2μ vector (Cadus plasmid 1849) that contained the PGK promoter followed by a synthetic oligonucleotide encoding the N-terminal 14 amino acids of AC4. Insertion of the SpeI to BglII fragment resulted in Cadus plasmid 1856, in which the PGK promoter directs transcription of the entire open reading frame of a version of AC4 in which the 14 N-terminal codons have been optimized for expression in yeast. Diploid yeast that are homozygous for the cdc35-1 allele, which encodes a temperature-sensitive yeast adenylyl cyclase, and that contain a plasmid encoding a CUP1 promoter-driven wild-type rat Gαs were transformed with Cadus plasmid 1856. Transformants were tested for their ability to grow at the restrictive temperature (34° C.) in the presence of copper. Strain CY2128 and CY2129, representatives of these transformants, exhibited copper-dependent temperature-resistant growth, indicating that AC4 can function in these yeast in the presence of mammalian Gαs. As was observed with AC2, integration of PGK promoter-driven AC4 at the LYS2 locus yielded strains that retained the ability to grow at 34° C. when Gαs is coexpressed.

GαsQ227L shows greater growth than wild-typet Gαs, reflected in greater background growth, more rapid growth, and greater temp resistance. Experiments with GαsG226A confirm that, Gαs.GTP is the activating species.

We have constructed both high copy and low copy plasmids that express wild-type rat Gαs from the haploid-specific GPA1 promoter, the copper-inducible CUP1 promoter, and the constitutive PGK promoter. In each case, expression of Gαs together with either AC2 or AC4 resulted in temperature-resistant growth of cdc35-1 yeast. As described above, Gαs can exist in two forms, distinguished by the guanine nucleotide bound to it: Gαs•GTP and Gαs•GDP. We determined which of the two species is responsible for stimulating adenylyl cyclase by comparing the temperature-resistant growth of strains expressing the wild-type Gαs with isogenic strains expressing either of two mutant forms of Gαs, $Gαs_{Q227L}$ and $Gαs_{G226A}$. The $Gαs_{Q227L}$ mutant has only 5% of wild-type GTPase activity, so it exists in predominantly in the Gαs•GTP form. In contrast, $Gαs_{G226A}$ shows severely comprised exchange of GTP for GDP, so it exists in predominantly in the Gαs•GDP form. If the Gαs•GTP form is the active species, we would expect that strains expressing mammalian adenylyl cyclases would show the greatest temperature resistant growth with coexpressed $Gαs_{Q227L}$ and the least temperature-resistant growth with coexpressed $Gαs_{G226A}$.

Cadus plasmid 1536 is analogous to Cadus plasmid 1046 (see above), except that it contains a constitutively active Gαs ($Gαs_{Q227L}$) in lieu of the wild type Gαs. Cadus plasmid 1843 is also analogous to Cadus plasmid 1046, except that it contains $Gαs_{G226A}$ in place of the wild type Gαs. Diploid temperature-sensitive yeast strains carrying PGK promoter-driven AC2 on a LEU2-marked high copy plasmid (Cadus plasmid 1512) were transformed with these plasmids to yield strains CY1429 and CY1430 (genotype cdc35-1/cdc35-1 cam/(cam?) ura3-52/ura3-52 leu2-3,112/leu2 trp1/trp1 his7/+[TRP1 CUP1P-ratGαs REP3 2mu-ori AmpR/LEU2 2mu-ori REP3 AmpR PGKp-ratACII]; CY1773 and CY1774 (genotype cdc35-1/cdc35-1 cam/(cam?) ura3-52ura3-52 leu2-3,112/leu2 trp1/trp1 his7/+[TRP1 CUP1P-ratGαs$_{Q227L}$ REP3 2mu-ori AmpR/LEU2 2mu-ori REP3 AmpR PGKp-ratACII]); and CY 2052 and CY2053 (genotype cdc35-1/cdc35-1 cam/(cam?) ura3-52/ura3-52 leu2-3,112/leu2 trp1/trp1 his7/+[TRP1 CUP1P-ratGαs$_{G226A}$ REP3 2mu-ori AmpR/LEU2 2mu-ori REP3 AmpR PGKp-ratACII]). Each of these strains was plated on synthetic media with and without 100 μM CuSO$_4$ and incubated at 34° C. While the strain expressing wild type Gαs grew in the presence but not the absence of copper, the strain expressing Gαs$_{G226A}$ showed no growth at 34° C. in the presence or absence of copper. The strain expressing Gαs$_{Q227L}$ grew in the presence and absence of copper, indicating that the specific activity of Gαs$_{Q227L}$ is sufficiently high to enable growth at 34° C. even at levels resulting from the basal activity of the CUP1 promoter. The greater activity of Gαs$_{Q227L}$ compared to wild type Gαs is also reflected by a greater range of temperature resistance of strains CY1773 and CY1774 compared to CY1429 and CY1430: AC2-expressing strains that contain Gαs$_{Q227L}$ will grow at temperatures as high as 37° C. if expression is induced with added copper, while strains containing wild type Gαs fail to show such temperature resistance under any conditions.

These experiments indicate that Gαs•GTP is the species that activate AC2 expressed in yeast. Similar results are obtained with AC4 in place of AC2. The results are consistent with in vitro studies that suggest that Gαs•GTP is the stimulatory form of Gαs. The results therefore indicate that mammalian adenylyl cyclases and mammalian G proteins expressed in yeast exhibit normal physiological behavior.

Human and rat Gαs proteins are equally effective in activating rat ACII. The genes encoding these proteins are expressed at different levels, however, due to a lower translatability of the 3' ⅓ of the coding sequence of the human Gαs mRNA.

Human and rat Gαs subunit protein differ at a single amino acid: the rat protein contains an asparagine at position 6 while this residue is a threonine in the human protein. To determine if the human and rat Gαs have different activities on adenylyl cyclase type 2 (AC2), the rat and human coding sequences were expressed from high copy plasmids containing the CUP1 promoter in haploid cdc35-1 yeast expressing AC2 from a promoter on a LEU2-marked, high-copy plasmid (Cadus plasmid 1512). The resulting strains showed different growth rates at the restrictive temperature: the strains expressing rat Gαs (CY1635 and CY1636) grew more rapidly than those expressing the human protein (CY1703 and CY1704). Similar results were observed in homozygous dipoid cdc35-1 yeast, with different promoters driving the expression of the two Gαs's (viz., PGK and GPA promoters), and with the Gαs's expressed from both high and low-copy plasmids. While these results suggested that the single amino acid difference between the rat and human proteins was responsible for the difference, additional experiments indicated that in fact this was not the case: yeast expressing a human Gαs from a chimeric gene, wherein the 5' approximately 30% (from the start codon through the Eco RI site) of the human Gαs coding sequence was replaced with the analogous region encoding the rat Gαs, grew at rates equal to that of the yeast expressing the rat gene. The lower activity of the human Gαs was mapped to the 3' one-third of the human Gαs coding region, from the BglII site to the stop codon, which encodes amino acids identical to those encoded by the rat gene in this region. We conclude that the 5' end of the human coding sequence is less efficiently expressed than the equivalent region of the rat gene, since we have no reason to doubt that the activities of the rat and human Gαs's that are expressed (i.e., their specific activities) are indistinguishable with respect to stimulation of adenylyl cyclases.

Construction of yeast expression vector for mouse adenylyl cyclase type 6 and rat adenylyl cyclase type 3.

We obtained mouse adenylyl cyclase type 6 from Gary Johnson as a 5 kb cDNA in a plasmid designated Cadus plasmid 1757. This was subcloned in three steps into a LEU2-marked high-copy yeast expression vector containing the PGK promoter (Cadus plasmid 1284). The first step consisted of : 1) amplifying from Cadus 1757 by the polymerase chain reaction (PCR) a fragment containing the N-terminal 1.2 kb of the AC6 open reading using oligo110 (5' CAGACATGTCTTGGTTTCGTGGCCTCCTG 3') (SEQ ID No:6) and oligo 111 (5' GCGGATCCAAGGTCAT-GACCAGTTCCTGTGCAGTGC 3') (SEQ ID No:7), 2) cutting the PCR product with Afl III and BamH I, and 3) cloning the amplified product into NcoI- and BamH I-digested Cadus plasmid 1284 (LEU2 PGKp 2mu-ori REP3 AmpR). This yielded Cadus plasmid 1918. Note that the 1.2 kb PCR-amplified product contains an Sph I site near its 3' end that derives from AC6. This endogenous Sph I site was used in the second step, which consisted of: 1) excising the 3' 574 nucleotides of the AC6 open reading frame from Cadus 1757 as part of a 2.1 kb Sph I-to-BamH I fragment and 2) cloning the fragment into Sph I- and BamH I-digested Cadus 1918. The result was Cadus plasmid 1919. The final step involved: 1) excising the middle 2 kb of AC6 open reading frame as an Sph I fragment, 2) cloning it into Sph I-digested Cadus 1919, and 3) screening recombinants for clones that contained a plasmid containing a reconstructed AC6 open reading frame. The resulting plasmid was designated Cadus plasmid 1950.

We obtained rat adenylyl cyclase type 3 (rat AC3) from Gary Johnson as a 4.5 kb cDNA in a plasmid designated Cadus plasmid 1756. The expression plasmid for expression of AC3 in yeast was constructed as follows. Oligos 112 (5' CATGACTGAAGATCAAGGTTTCTCG 3') (SEQ ID No:8) and 113 (5' GATCCGAGAAACCTTGATCTTCAGT 3') (SEQ ID No:9) were annealed, and the double-stranded oligonucleotide, which encodes the N-terminal 9 amino acids of AC3, was cloned into Nco I- and BamH I-digested Cadus plasmid 1284 (LEU2 PGKp 2mu-ori REP3 AmpR) to yield Cadus plasmid 1894. The rest of the AC3 open reading frame was then inserted by cloning the 3.5 kb BamH I-to-HindIII fragment from Cadus 1756 into BamH I- and HindIII-digested Cadus 1894. The resulting plasmid, Cadus 1916, contains an AC3-encoding gene whose N-terminal 8 amino acids are optimized for expression in yeast and whose transcription is directed by the PGK promoter.

In cam1,2,3 strains expressing Gαs and various cyclase isoforms: ACI shows a temperature optimum at Room Temperature(RT), with some growth at 30° C.; AC IV and ACVI show growth over a broad temp range; the optimum for ACIV may be RT, for ACVI may be 30° C. ACIII shows no growth at any temp.

Yeast strains that contain the cdc35-1 temperature-sensitive allele can grow at 30° C. and lower temperatures, reflecting the activity of the mutant yeast adenylyl cyclase at these temperatures. When these strains are used to assess the capacity for mammalian adenylyl cyclases to complement the cdc35-1 mutation, complementation tests can only be done at temperatures above 30° C. In practice, the temperature range available for such tests is about 33° C. to 37° C. If for some reason the mammalian enzyme is not functional in this relatively narrow temperature range, then successful complementation will not be observed in this yeast background. It is therefore advantageous to have a strain background that permits determination of functional cyclase activity at temperatures below 30° C.

We have obtained a yeast strain from Dr. Al Gilman at the University of Texas Southwestern Medical Center that is derived from a strain (TC41) constructed by Warren Hiedeman at the University of Wisconsin. Strain TC41 does not encode a yeast cyclase as a result of deletion of CYR1 and carries three uncharacterized mutations (cam1, cam2, and cam3) that enable growth of the strain on media containing cAMP. Dr. Gilman's group has modified this strain in part by integrating rat G$\alpha$s$_{Q227L}$ under the control of the CUP1 promoter at the TRP1 locus. The resulting strain (CY2828; genotype MATa cyr1::ura3 trp1-1::CUP1p-G$\alpha$sQ227L cam1 cam2 cam3 leu2-3 leu2-112 his3-532 his4) requires added cAMP to grow.

To examine the ability of various mammalian adenylyl cyclases to enable growth of CY2828 in the absence of added cAMP, we transformed CY2828 with: 1) Cadus plasmid 1856 (described above), which encodes AC4, to yield sibling strains CY2906 and CY2907 (genotype MATa cyr1::ura3 trp1-1::CUP1p-G@sQ227L cam1 cam2 cam3 leu2-3 leu2-112 his3-532 his4 [LEU2 2mu-ori REP3 AmpR PGKp-ACIV]); 2) Cadus plasmid 1916 (described above), which encodes AC3, to yield sibling strains CY2908 and CY2909 (genotype MATa cyr1::ura3 trp1-1::CUP1p-G@sQ227L cam1 cam2 cam3 leu2-3 leu2-112 his3-532 his4 [LEU2 2mu-ori REP3 AmpR PGKp-ACIII]); 3) Cadus plasmid 1950 (described above), which encodes AC6, to yield sibling strains CY2910 and CY2911 (genotype MATa cyr1::ura3 trp1-1::CUP1p-G@sQ227L cam1 cam2 cam3 leu2-3 leu2-112 his3-532 his4 [LEU2 2mu-ori REP3 AmpR PGKp-ACVI]); and 4) Cadus plasmid 2129 (constructed in Dr. Giman's laboratory), which encodes AC1, to yield sibling strains CY2906 and CY2907 (genotype MATa cyr1::ura3 trp1-1::CUP1p-G@sQ227L cam1 cam2 cam3 leu2-3 leu2-112 his3-532 his4 [AmpR LEU2 CEN ARS CUP1p-ste6-AC1]). Growth of each strain was determined in the absence of exogenous cAMP at room temperature, 30°C., 34°C., and 37° C. Both AC4 and AC6 showed effective complementation of the cyr1 deletion at 30° C. and 34° C.; AC1 complemented the deletion best at room temperature; and AC3 was unable to complement the deletion at any temperature tested.

Evidence that $\beta\gamma$ can form a functional heterotrimer as evidence by reduction of the stimulation of cyclase by G$\alpha$.

We constructed URA3-marked CEN ARS plasmids that contained various pairs of G$\beta$ and G$\gamma$ on the same plasmid. For example, a plasmid that expresses both G$\beta$1 and G$\gamma$2 was constructed as follows. The open reading frame of bovine G$\gamma$2 was PCR-amplified from Cadus plasmid 1319 (provided by Dr. Melvin Simon and containing the G$\gamma$2 cDNA) using primers A14652 (5' GGGCGTCTCCCATG-GCCAGCAACAACACCGC 3') (SEQ ID No:10 and A14653 (5' GGGGTCGACCGAGGCTCCTCAGGTTC-CTC 3')(SEQ ID No:11). The amplified product was digested with Esp3I and Sal I and cloned into the Nco I and Sal I sites of Cadus plasmid 1449. The resulting plasmid, Cadus 1705, uses the PGK promoter to direct expression of G$\gamma$2. The PGKpromoter-G$\gamma$2 unit was then excised from Cadus 1705 as a 1 kb Not I-to-Xho I fragment and cloned into Not I- and Xho I-digested Cadus plasmid 1460. The resulting plasmid, Cadus 1781, then received a 422 bp fragment containing the ADH1 promoter. Specifically, the ADH1 promoter was removed from Cadus 1625 by cutting with NheI, filling in the overhang, cutting with Spe I, and isolating the 422 bp fragment. This fragment was ligated to Cadus 1781 that had been cut with XbaI, the 5' overhang filled in, and digested with SpeI. A recombinant (Cadus plasmid 2209) that contained the ADH1 promoter together with PGK promoter-driven G$\gamma$2 was selected and used as the recipient for the G$\beta$1 open reading frame. In particular, the bovine G$\beta$1 open reading frame was PCR-amplified from Cadus 1315 (provided by Dr. Mel Simon and containing the G$\beta$1 CDNA) using primer 123(5' CGGCTAGCATC-TATATACAATGAGTGAACTTGACCAGTTACGGC 3') (SEQ ID No:12) and primer 127 (5' CGAGCGGCCGCT-CAGTTCCAGATTTTGAGGAAGCTGTCC 3') SEQ ID No:3. The amplified product was digested with Not I and Nhe I and cloned into NotI- and Nhe I-digested Cadus 2209, yielding Cadus plasmid 2254. Thus, Cadus 2254 is a URA3-marked low-copy plasmid that directs the expression of G$\gamma$2 from the PGK promoter and G$\beta$1 from the ADH1 promoter. A similar construction strategy yielded analogous plasmids encoding G$\beta$1 and G$\gamma$1 (Cadus plasmid 2255), G$\beta$2 and G$\gamma$1 (Cadus plasmid 2257), G$\beta$2 and G$\gamma$2 (Cadus plasmid 2256), G$\beta$3 and G$\gamma$1 (Cadus plasmid 2259), G$\beta$3 and G$\gamma$2 (Cadus plasmid 2258), G$\beta$4 and G$\gamma$1 (Cadus plasmid 2363), and G$\beta$4 and G$\gamma$2 (Cadus plasmid 2361).

We have tested the ability of G$\beta$1 and G$\gamma$2 (encoded by Cadus 2254) and G$\beta$1 and G$\gamma$1 (encoded by Cadus 2255) to form a complex with G$\alpha$s by assessing the effect of coexpression of G$\beta$ and G$\gamma$ on the stimulation of AC2 by G$\alpha$s. If a G$\alpha\beta\gamma$ it complex can be formed upon coincident expression of the three G protein subunits, we would expect that the level of free G$\alpha$ would be lower in yeast expressing all three subunits compared to yeast expressing only the G$\alpha$ subunit. This would be reflected as slower growth of a cdc35-1 strain expressing a mammalian adenylyl cyclase together with the three G protein subunits compared to an equivalent strain expressing the mammalian cyclase with G$\alpha$ alone.

Yeast strain CY2065 (genotype MATa/$\alpha$ lys2::PGKp-ACII/lys2::PGKp-ACII tbt1-1/tbt1-1 cdc35-1/cdc35-1 cam/(cam?) ura3/ura3 leu2/leu2 trp1/trp1) was transformed with Cadus plasmid 2081 (TRP1 CEN6 ARSH4 AmpR CUP1p-ratG$\alpha$s) and Cadus plasmid 2254 (URA3 PGKp-G$\gamma$2 CEN6 ARSH4 AmpR ADH1p-G$\beta$1) to get sibling strains CY3845 and CY3846. These strains will express mammalian proteins G$\beta$1, G$\gamma$2, and AC2 constitutively and G$\alpha$s in the presence of added copper. Equivalent strains were constructed that express mammalian proteins G$\alpha$s, G$\beta$1, G$\gamma$1, and AC2 (CY3847 and CY3848) or G$\alpha$s and AC2 alone (CY3861 and CY3862). These 6 strains were tested for temperature-resistant growth at 34° C. by spotting one thousand cells on solid media that selects for maintenance of the plasmids. The strains containing Cadus plasmid 2254 (encoding G$\beta$1 and G$\gamma$2) or Cadus plasmid 2255 (encoding G$\beta$1 and G$\gamma$1) grew more slowly than those not expressing a G$\beta\gamma$. We conclude that coexpression of the three G protein subunits results in the formation of a G protein heterotrimer.

References

Aiba H., Mori K., Tanaka M., Ooi T., Roy A., Danchin A (1984) The complete nucleotide sequence of the adenylyl cyclase gene of *Escherichia coli*. Nucl. acids Res. 12, 9427–9440.

Alexandre S., Paindavoine P., Tebabi P., Pays A., Halleux S., Steinert M., Pays E. (1990) Differential expression of a family of putative adenylate/guanylate cyclase genes in *Trypanosoma brucci*. Mol. Biochem. Parasitol. 43, 279–288.

Arkinstall, S., Payton, M. and Mondrell, K., (1995) Activation of Phospholipase C gamma in *Schizosaccharomyces pombe*. Mol. Cell. Biol. 15, 3, 1451:1458.

Bakalyar H. A. and Reed R. R. (1990) Identification of a specialized adenylyl cyclase that may mediate odorant detection. Science 250, 1403–1406.

Beals, C. R., Wilson, C. B. and Perlmutter, R. M. (1987) A small multigene family encodes $G_i$ signal-transduction proteins. Proc. Natl. Acad. Sci. U.S.A 84, 7886–7890.

Bennetzen J. L., and Hall B. D. (1982) Codon selection in yeast. J. Biol. Chem. 257, 3026–3031.

Boutelet F. and Hilger F. Tenth International Conference on Yeast Genetics and Molecular Biology, Sep. 8–12, 1980, Louvain-la-Neuve, Belgium, p. 177 (abstract).

Bourne H. R., Sanders D. A., McCormick F. (1991) THe GTPase superfamily:conserved structure and molecular mechanism. Nature 349, 117–127.

Bray, P., Carter, A., Guo, V., Puckett, C., Kamholz, J., Spiegel, A., and Nirenberg, M. (1987) Human CDNA clones for an α subunit of $G_i$ signal-transduction protein. Proc. Natl. Acad. Sci. USA 84, 5115–5119.

Bray, P., Carter, A., Simons, C., Guo, V., Puckett, C., Kamholz, J., Spiegel, A., Nirenberg, M., (1986) Human cDNA clones for four species of Gαs signal transduction protein. Proc. Natl. Acad. Sci. U.S.A. 83, 8893–8897.

Broach J. R., Li Y.-Y., Wu L.-C. C., Jayarum M. (1983) in "Experimental Manipulation of Gene Expression" (M. Inouye, ed.) pp. 83–117. Academic Press, New York.

Broek D., Samiy N., Fasano O., Fujiyama A., Tamanoi F., Northup J., Wigler M. (1985) Differential activation of yeast adenylyl cyclase by wild-type and mutant RAS proteins. Cell 41, 763–769.

Cali J. J., Balcueva E. A., Rybalkin I., Robishaw J. D. (1992) Selective tissue distribution of G protein γ subunits, including a new form of the γ subunits identified by cDNA cloning. J. Biol. Chem. 267, 24023–24027.

Casperson G. F., Walker N., Bourne H. R. (1985) Isolation of the gene encoding adenylate cyclase in *Saccharomyces cerevisiae*. Proc. Natl. Acad. Sci. USA 82, 5060–5063.

Chinkers M. and Garbers D. L. (1991) Signal transduction by guanyl cyclases. Ann. Rev. Biochem. 60, 553–575.

Codina, J., Stengel, D., Woo, S. L. C., and Birnbaumer, L. (1986) Beta-subunits of the human liver Gs/Gi signal-transducing proteins and those of bovine retinal rod cell transducin are identical. FEBS Lett. 207, 187–192.

Colicelli J., Field J., Ballester R., Chester N., Young D., Wigler M. (1990) Mutational mapping of RAS-responsive domains of the *S. cerevisiae* adenylyl cyclase. Mol. Cell. Biol. 10, 2539–2543.

Conklin B. R., Farfel Z., Lustig K. D., Julius D. and Bourne H. R. (1993) Substitution of three amino acids switches receptor specificity of Gαq to that of Gαi. Nature 363, 274–276.

Cull M G; Miller J F; Schatz P J (1992) Screening for receptor ligands using large libraries of peptides linked to the C terminus of the lac repressor. Proc Natl Acad Sci USA 89, 1865–1869.

Cwirla S. E., Peters E. A., Barrett R. W., Dower W. J. (1990) Peptides on phage: A vast library of peptides for identifying ligands. Proc. Natl. Acad. Sci. U.S.A. 87, 6378–6382.

Devlin J. J., Panganiban L. C., Devlin P. E. (1990) Random peptide libraries: A source of specific binding molecules. Science 249, 404–406.

Devreotes P. (1989) *Dictyostelium discoideum*: A model system for cell-cell interactions in development. Science 245, 1054–1058.

Didsbury, J. R. and Snyderman, R. (1987) Molecular cloning of a new human G protein: evidence for two $G_{i\alpha}$-like protein families. FEBS Lett. 219, 259–263.

Didsbury, J. R., Ho, Y.-S., and Snyderman, R. (1987) Human $G_i$ protein α subunit: deduction of amino acid structure from a cloned cDNA. FEBS Lett. 211, 160–164.

Dietzel C., Kurjan J. (1987) The Yeast SCG1 Gene: A Gα-like protein implicated in the a-and α-factor response pathway. Cell 50, 1001–1010.

Dratz E. A., Furstenau J. E., Lambert C. G., Thireault D. L., Rarick H., Schepers T., Pakhlevaniants S., Hamm H. E. (1993) NMR structure of a receptor-bound G-protein peptide. Nature 363, 276–281.

Feinstein P. G., Schrader K. A., Bakalyar H. A., Tang W. J., Koprinski J., Gilman A. G., Reed R. R. (1991) Molecular cloning and characterization of a $Ca^{2+}$/calmodulin-insensitive adenylyl cyclase from rat brain. PNAS 88, 10173–10177.

Felici F., Castagnoli L., Musacchio A., Jappelli R., Cesareni G. (1991) Selection of antibody ligands from a large library of oligopeptides expressed on a multivalent exposition vector. J. Mol. Biol. 222, 301–310.

Field J., Xu H.-P., Michaeli T., Ballester R., Sass P., Wigler M., Colicelli J. (1990) Mutations of the adenylyl cyclase gene that blocks RAS function in *Saccharomyces cerevisiae*. Science 247, 464–467.

Fisher, K. J. and Aronson, N. N. Jr. (1992) Characterization of the cDNA and genomic sequence of a G protein γ subunit (γ5). Mol. Cell. Biol. 12, 1585–1591.

Florent I., Raibaud A., Eisen H. (1991) A family of genes related to a new expression site-associated gene in *Trypanosoma equiperdum*. Mol. Cell. Biol. 11, 2180–2188.

Fodor S. P. A., Read J. L., Pirrung M. C., Stryer L., Lu A. T., Solas D. (1991) Light-directed, spatially addressable parallel chemical synthesis. Science 249, 386–390.

Fong, H. K. W., Amatruda, T. T., III, Birren, B. W., and Simon, M. I. (1987). Distinct forms of the β subunit of GTP-binding regulatory proteins identified by molecular cloning. Proc. Natl. Acad. Sci. U.S.A. 84, 3792–3796.

Fong, H. K., Hurley, J. B., Hopkins, R. S., Miake-Lye, R., Johnson, M. S., Doolittle, R. F., and Simon, M. I. (1986) Repetitive segmental structure of the transducin beta subunit: Homology with the CDC4 gene and identification of related mRNAs. Proc. Natl. Acad. Sci. U.S.A. 83, 2162–2166.

Gao B. and Gilman A. G. (1991) Cloning and expression of a widely distributed (type IV) adenylyl cyclase. PNAS 88, 10178–10182

Gao, B., Gilman, A. G., and Robishaw, J. D. (1987). A second form of the β subunit of signal-transducing G proteins. Proc. Natl. Acad. Sci. U.S.A. 84, 6122–6125.

Gautam, N., Northup, J., Simon, M. I. (1990) G protein diversity is increased by associations with a variety of γ subunits. Proc. Natl. Acad. Sci. U.S.A. 87, 7973–7977.

Gilman A. G. (1984) G proteins and dual control of adenylate cyclase. Cell 36, 577–579.

Gilman A. (1984) G proteins and dual control of adenylyl cyclase. Cell 36, 577–579.

Hadwiger J. A., Wilkie T. M., Stratmann M., Firtel R. A. (1991) Identification of Dictyostelium Gα genes expressed during multicellular development. Proc. Natl. Acad. Sci. USA 88, 8213–8217.

Harris, B. A., Robishaw, J. D., Mumby, S. M., and Gilman, A. G. (1985) Molecular cloning of complementary DNA for the alpha subunit of the G protein that stimulates adenylate cyclase. Science 229, 1274–1277.

Hashimoto C., Hudson K. L., Anderson K. V. (1988) The Toll gene of Drosophila, required for dorsal-ventral embryonic polarity, appears to encode a transmembrane protein. Cell 52, 269–279.

Hoekma A., Kastelein R. A., Vasser M., DE Boer H. A. (1987) Codon replacement in the PGK1 gene of *Saccharomyces cerevisiae*: Experimental approach to study the role of biased codon usage in gene expression. Mol. cell. Biol. 7, 2914–2924.

Holbrook S. and Kim S.-H. (1989) Molecular model of the G protein α subunit based on the crystal structure of the HRAS protein. Proc. Natl. Acad. Sci. USA 86, 1751–1755.

Houghten R. A., Pinilla C., Blondelle S. E., Appel J. R., Dooley C. T., Cuervo J. H. (1991) Generation and use of synthetic peptide combinatorial libraries for basic research and drug discovery. Nature 354, 84–86.

Hurley, J. B., Fong, H. K., Teplow, D. B., Dreyer, W. J., Simon, M. I. (1984) Isolation and characterization of a cDNA clone for the γ subunit of bovine retinal transducin. Proc. Natl. Acad. Sci. U.S.A. 81, 6948–6952.

Iniguez-Lluhi J. A., Simon, M. I., Robishaw J. D., Gilman A. G. (1992) G protein βγ subunits synthesized in Sf9 cells. J. Biol. Chem. 267, 23409–23417.

Ishikawa Y., Katsushika S., Chen L., Halnoon N. J., Kawabe J., Homcy C. J. (1992) Isolation and characterization of a novel cardiac adenylyl cyclase cDNA. J. Biol. Chem.267, 13553–13557.

Itoh, H., Kozasa, T., Nagata, S., Nakamura, S. I., Katada, T., Ui, M., Iwai, S., Ohtsuka, E., Kawasaki, H., Suzuki, K., and Kaziro, Y. (1986) Molecular cloning and sequence determination of cDNAs for α subunits of the guanine nucleotide-binding proteins $G_s$, $G_i$, and $G_o$ from brain. Proc. Natl. Acad. Sci. U.S.A. 83, 3776–3780.

Itoh, H., Toyama, R., Kozasa, T., Tsukamoto, T., Matsuoka, M., Kaziro, Y. (1988) Presence of three distinct molecular species of Gi protein α subunit. Structure of rat cDNAs and human genomic DNA S. J. Biol. Chem. 263, 6656–6664.

Iyengar R. (1993) Molecular and functional diversity of mammalian Gs-stimulated adenylyl cyclases. FASEB J. 7, 768–775.

Jacobowitz O., Chen J., Premont R. T., Iyengar R. (1993) Stimulation of specific types of adenylyl cyclases by phorbol ester treatment. J. Biol. Chem. 268, 3829–3832.

Johnson J. A., Friedman J., Halligan R. D., Birnbaumer M, Clark R. D. (1991) Sensitization of adenylyl cyclase by P2 purinergic and M5 muscarinic receptors in L cells. J. Pharmacol. Exp. Ther. 39, 539–546.

Jones, D. T. and Reed, R. R. (1987) Molecular cloning of five GTP binding protein cDNA species from rat olfactory neuroepithelium. J. Biol. Chem. 262, 14241–14249.

Jurnak F. (1985) Structure of the GDP domain of EF-Tu and location of the amino acids homologous to ras oncogene proteins. Science 230, 32–36.

Kaiser C. A., Preuss D., Grisafi P. and Botstein D. (1987) Many random sequences functionally replace the secretion signal sequence of yeast invertase. Science 235, 312–317.

Kang Y.-S., Kane J., Kurjan J., Stadel J. M., Tipper D. J. (1990) Effects of expression of mammalian Gα and hybrid mammalian-yeast Gα proteins on the yeast pheromone response signal transduction pathway. Mol. Cell. Biol. 10, 2582–2590.

Katsushika S., Chen L., Kawabe J.-I., Nilakantan R., Halnon N. J., Homcy C. J., Ishikawa Y. (1992) Cloning and characterization of a sixth adenylyl cyclase isoform: Types V and VI constitute a subgroup within the mammalian adenylyl cyclase family. Proc. Natl. acad. sci. USA 89, 8774–8778.

Katz, A., Wu, D., and Simon, M. I. (1992) Subunits βγ of. heterotrimeric G protein activate β2 isoform of phospholipase C. Nature 360, 686–689.

Kim, S., Ang, S.-L., Bloch, D. B., Bloch, K. D., Kawahara, Y., Tolman, C., Lee, R., Seidman, J. G., and Neer, E. J. (1988) Identification of cDNA encoding an additional α subunit of a human GTP-binding protein: Expression of three $α_1$ subtypes in human tissues and cell lines. Proc. Natl. Acad. Sci. U.S.A. 85, 4153–4157.

Kozasa, T., Itoh, H., Tsukamoto, T., Kaziro, Y., (1988). Isolation and characterization of human Gsα gene. Proc. Natl. Acad. Sci. U.S.A. 85: 2081–2085.

Kesbeke F., Snaar-Jagalska E., Van Haastert P. J. M., (1988) Signal transduction in Dictyostelium Frd A mutants with a defective interaction between surface cAMP receptor and a GTP-binding regulatory protein. J. Cell. Biol. 107, 521–528.

Koesling D., Boheme E., Schultz G. (1991) Guanylyl cyclases, a growing family of signal-transducing enzymes. FASEB J. 5, 2785–2791.

Krupinski J., Coussen F., Bakalyar H. A., Tang W.-J., Feinstein P. G., Orth K., Slaughter C., Reed R. R., Gilman A. G. (1989) Adenylyl cyclase amino acid sequence: possible channel- or transporter-like structure. Science 244, 1558–1564.

Krupinski J., Lehman P. C., Frankenfield C. D., Zwaagstra J. C., Watson P. A. (1992) Molecular diversity in adenylyl cyclase family evidence for eight forms of the enzyme and cloning of type 6. J. Biol. Chem. 267, 24858–25862.

LaCour T. F. M., Nyborg J., Thirup S., Clark B. F. C. (1985) Structural details of the binding of guanosine diphosphate to elongation factor Tu from *E. coli* as studied by X-ray crystallography. EMBO J. 4, 2385–2388.

Lam K. S., Salmon S. E., Hersh E. M., Hruby V. J., Kazmierski W. M., Knapp R. J. (1991) A new type of synthetic peptide library for identifying ligand-binding activity. Nature 354, 82–84.

Lemire, B. D., Fankhauser, C., Baker, A., Schatz, G. (1989) The mitochondrial targeting function of randomly generated peptide sequences correlates with predicted helical amphiphilicity. J. Biol. Chem. 264, 20206–20215.

Levine, M. A., Smallwood, P. M., Moen, P. T. Jr., Helman, L. J., Ahn, T. G. (1990) Molecular cloning of the β3 subunit, a third form of the G protein β-subunit polypeptide. Proc. Natl. Acad. Sci. U.S.A. 87, 2329–2333.

Levin L. R., Han P.-Y., Hwang P. M., Feinstein P. G., Davis R. L., Reed R. R. (1992) The Drosophila learning and memory gene rutabaga encodes a $Ca^{2+}$/calmodulin responsive adenylyl cyclase. Cell 68, 479–489.

Lopez J. A., Chung D. W., Fujikawa K., Hagen F. S., Davie E. W., Roth G. J. (1988) The α and β chains of human glycoprotein Ib are both transmembrane proteins containing a leucine-rich amino acid sequence. Proc. Natl. Acad. Sci. USA 85, 2135–2139.

Markby D. W., Onrust R., Bourne H. R. (1993) Separate GTP binding and GTPase activating domains of a Gα subunit. Science 262, 1895–1901.

Matsumoto K., Uno I., Toh-E. A., Ishikawa T., Oshima Y. (1982) Cyclic AMP may not be involved in catabolite repression in *Saccharomyces cerevisiae*: Evidence from mutants capable of utilizing it as an adenine source. J. Bacteriol. 150, 277–285.

Mattera, R., Codina, J., Crozat, A., Kidd, V., Woo, S. L. C., and Birnbaumer, L. (1986) Identification by molecular cloning of two forms of the α-subunit of the human liver stimulatory ($G_s$) component of adenylate cyclase. FEBS Lett. 206, 36–41.

Mercken L., Moras V., Tocque B., Mayaux J. F. (1990) The cDNA sequence of the alpha subunit of the Chinese hamster adenylate cyclase-stimulatory G-protein. Nuc. Acids Res. 18, 662.

Michel T., Winslow J. W., Smith J. A., Seidman J. G., Neer E. J. (1986) Molecular cloning and characterization of cDNA encoding the GTP-binding protein alpha i and identification of a related protein alpha h. Proc. Natl. Acad. Sci. U.S.A. 83, 7663–7667.

Mitts M. R., Grant D. B., Heideman W. (1990) Adenylate cyclase in *Saccharomyces cerevisiae* is a peripheral membrane protein. Mol. Cell. Biol. 10, 3873–3883.

Nakane M., Arai K. Saheki S., Kuno T., Buechler W., Murad F. (1990) Molecular cloning and expression of cDNAs coding for soluble guanylate cyclase from rat lung. J. Biol. Chem. 265, 479–489.

Noel J. P., Hamm H. E., Sigler, P. B. (1993) The 2.2 A crystal structure of transducin-alpha complexed with GTP-gamnma-S. Nature 366, 654–663.

Northup J. K., Sternweis P. C., Smigel M. D., Schleifer L. S., Ross E. M., Gilman A. G. (1980) Purification of the regulatory component of adenylate cyclase. Proc. Natl. Acad. Sci. USA 77, 6516–6520.

Nukada T., Tanabe T., Takahashi H., Noda M. et al. (1986) Primary structure of the alpha-subunit of bovine adenylate cyclase-stimulatory G-protein deduced from the cDNA sequence. FEMS Lett. 195, 220–224.

Paindavoine P., Rolin S., Van AsselS., Geuskens M et al. (1992) A gene from the variant surface glycoprotein expression site encodes one of several transmembrane adenylyl cyclases located on the flagellum of *Trypanosoma brucei*. Mol. Cell. Biol. 12, 1218–1225.

Parma J., Stengel D., Gannage M.-H., Poyard M., Barouki R., Hanoune J. (1991) Sequence of a human brain adenylyl cyclase partial cDNA. Evidence for a consensus cyclase specific domain. Biochem. Biophys. Res. Comm. 179, 455–462.

Pitt G. S., Milona N., Borleis J., Lin K. C., Reed R. R., Devreotes P. N. (1992) Structurally distinct and stage-specific adenylyl cyclase genes play different roles in Dictyostelium development. Cell 69, 305–315.

Premont R. T., Chen J., Ma H.-W., Ponnapalli M., Iyengar R. (1992) Two members of a widely expressed subfamily of hormone stimulated adenylyl cyclases. PNAS 89, 9808–9813.

Premont R. T., Jacobowitz O., Iyengar R. (1992) Lowered responsiveness of the catalyst of adenylyl cyclase to stimulation by Gs in heterologous desensitization: a role for cAMP-dependent phosphorylation. Endocrinology 131, 2774–2783.

Pronin, A. N. and Gautam, N. (1992) Interaction between G-protein β and γ subunit types is selective. Proc. Natl. Acad. Sci. U.S.A. 89, 6220–6224.

Pupillo M., Insall R., Pitt G. S., Devreotes P. N. (1992) Multiple cyclic AMP receptors are linked to adenylyl cyclase in Dictyostelium. Molec. Biol. of the Cell 3, 1229–1234.

Rall T. and Harris B. A. (1987) Identification of the lesion in the stimulatory GTP-binding protein of the uncoupled S49 lymphoma. FEBS Lett. 224, 365–371.

Robishaw, J. D., Kalman, V. K., Moomaw, C. R., Slaughter, C. A. (1989) Existence of two γ subunits of the G proteins in brain. J. Biol. Chem. 264, 15758–15761.

Robishaw, J. D., Russell, D. W., Harris, B. A. Smigel, M. D. and Gilman, A. G. (1986a) Deduced primary structure of the α subunit of the GTP-binding stimulatory protein of adenylate cyclase. Proc. Natl. Acad. Sci. U.S.A. 83, 1251–1255.

Ross, E. M., and Gilman, A. G. (1977). Resolution of some components of adenylate cyclase necessary for catalytic activity. J. Biol. Chem. 252, 6966–6969.

Ross D. T., Raibaud A., Florent I. C., Sather S., Gross M. K., Storm D. R., Eisen H. (1991) The trypanosome VSG expression site encodes adenylyl cyclase and a leucine-rich putative regulatory gene. EMBO J. 10, 2047–2053.

Ruth J., Hirt H., Schweyen R. J. (1992) The cauliflower mosaic virus 35S promoter is regulated by cAMP in *Saccharomyces cerevisiae*. Mol. Gen. Genet. 235, 365–372.

Schmidt, C. J., Thomas, T. C., Levine, M. A., Neer, E. J. (1992) Specificity of G protein β subunit and γ subunit interactions. J. Biol. Chem. 267, 13807–13810.

Scott J. K. and Smith G. P. (1990) Searching for peptide ligands with an epitope library. Science 249, 386–390.

Sharp P. M., Tuohy T. M. F., Mosurski K. R. (1986) Codon usage in yeast: cluster analysis clearly differentiates highly and lowly expressed genes. Nuc. Acids Res. 14, 5125–5143.

Shilo V., Simchen G., Shilo B. (1978) Initiation of meiosis in cell cycle initiation mutants of *Saccharomyces cerevisiae*. Exp. Cell Res. 112, 241–248.

Smith R. A., Sisk R., Lockhart P., Mathewes S., Gilbert T., Walker K., Piggot J. (1993) Isolation of glucagon antagonists by random molecular mutagenesis and screening. Mol. Pharmacol. 43, 741–748.

Sugimoto K., Nukada, T., Tanabe, T., Takahashi, H., Noda, M., Minamino, N., Kangawa, K., Matsuo, H., Hirose, T., Inayama, S., Numa, S. (1985) Primary structure of the β-subunit of bovine transducin deduced from the cDNA sequence. FEBS Lett. 191, 235–240.

Suki, W. N., Abramowitz, J., Mattera, R., Codina, J. and Birnbaumer, L. (1988) The human genome encodes at least three non-allelic G proteins with αi-type subunits. FEBS Lett. 220, 187–192.

Sullivan K. A., Liao Y. C., Alborzi A., Beiderman B. et al. (1986) Inhibitory and stimulatory G proteins of adenylate cyclase: CDNA and amino acid sequences of the alpha chains. Proc. Natl. Acad. Sci. U.S.A. 83, 6687–6691.

Sullivan, K. A., Miller, R. T., Masters, S. B., Biederman, B., Heideman, W., and Bourne, H. R. (1987). Identification of receptor contact site involved in receptor-G protein coupling. Nature 330, 758–760.

Takahashi N., Takahashi Y., Putnam F. W. (1985) Periodicity of leucine and tandem repetition of a 24-amino acid segment in the primary structure of leucine-rich α2-glycoprotein of human serum. Proc. Natl. Acad. Sci. USA 82, 1906–1910.

Tang W.-J. and Gilman A. G. (1992) Adenylyl cyclases. Cell 70, 869–872.

Tang W.-J., Iniguez-Lluhi J. A., Mumby S. M., Gilman A. G. (1992) Regulation of mammalian adenylyl cyclases by G protein α and βγ subunits. Cold Spring Harbor Symp. Quant. Biol. 57, 135–144.

Tang W.-J., Krupinski J., Gilman A. G. (1991) Expression and characterization of calmodulin activated adenylyl cyclase. J. Biol. Chem. 266, 8595–8603.

Taussig R., Iñiguez-Lluhi J. A., Gilman A. G. (1993) Inhibition of adenylyl cyclase by Giα. Science 261, 218–221.

Taussig R., Iñiguez-Lluhi J. A., Gilman A. G. (1993) Inhibition of adenylyl cyclase by Gαi. Science 261, 218–221.

Taussig R., Quarmby L. M., Gilman A. G. (1993) Regulation of purified type 1 and 2 adenylyl cyclases by G protein βγ subunits. J. Biol. Chem. 268, 9–12.

Taussig R., Tang W. J., Helper J. R., Gilman A. G. (1994) Distinct patterns of bidirectional regulation of mammalian adenylyl cyclases. J. Biol. Chem. 269, 6093–6100.

Toda T., Uno I., Ishikawa T., Powers S., Kataoka T., Broek D., Cameron S., Broach J., Matsumoto K., and Wigler M. (1985) In yeast, RAS proteins are controlling elements of adenylyl cyclase. Cell 40, 27–36.

von Weizsacker, E., Strathmann, M. P., and Simon, M. I. (1992) Diversity among the beta subunits of heterotrimeric GTP-binding proteins: characterization of a novel beta-subunit CDNA. Biochem. Biophys. Res. Commun. 183, 350–356.

Weinstein, L. S., Spiegel, A. M., Carter, A. D. (1988) Cloning and characterization of the human gene for the α subunit of Gi2, a GTP-binding signal transduction protein. FEBS Lett. 232, 333–340.

Whiteway M., Hougan L., Dignard D., Thomas D. Y., Bell L., Saari G. C., Grant F. J., O'Hara P., MacKay V. L. (1989) The STE4 and STE18 genes of yeast encode potential β and γ subunits of the mating factor receptor-coupled G protein. Cell 56, 467–477.

Wu L. and Devreotes P. N. (1991) Dictyostelium transiently expresses eight distinct G protein α-subunits during its developmental program. Biochem. Biophys. Res. Commun. 179, 1141–1147.

Yatomi Y., Arata Y., Tada S., Kume S., Ui M. (1992) Phosphorylation of the inhibitory guanine-nucleotide-binding protein as a possible mechanism of inhibition by protein kinase C of agonist-induced $Ca^{2+}$ mobilization in human platelet. Eur. J. Biochem. 205, 1003–1009.

Yoshimasa T., Sibley D. R., Bouvier M., Lefkowitz R. J., Caron M. G. (1991) Cross-talk between cellular signalling pathways suggested by phorbolester induced adenylyl cyclase phosphorylation. Nature 327, 67–70.

Yoshimura M. and Cooper D. M. F. (1992) Cloning and expression of a $Ca^{2+}$ inhibitable adenylyl cyclase from NCB-20 cells. PNAS 89, 6716–6720

Yoshimura M. and Cooper D. M. F. (1993) Type specific stimulation of adenylyl cyclase by protein kinase C. J. Biol. Chem. 268, 4604–4607.

Additional References

Anderson M. P., Gregory R. J., Thompson S., Souza D. W., Paul, S. et al. (1991) Demonstration that CFTR is a chloride channel by alteration of its anion selectivity. Science 253, 202–205.

Artemeyev N. O., Rarick H. M., Mills J. S., Skiba N. P., and Hamm H. E. (1992) Sites of interaction between rod G-protein α-subunit and cGMP-phosphodiesterase γ-subunit. J. Biol. Chem. 267, 25067–25072.

Banerjee S., Anderson G. D., Luthra H. S., David C. S. (1989) Influence of complement C5 and V beta T cell receptor mutations on susceptibility to collagen-induced arthritis in mice. J. Immunol. 142: 2237–2243.

Barr P. J., Mason O. B., Landsberg K. E., Wong P. A. et al. (1991) cDNA and gene structure for a human subtilisin-like protease with cleavage specificity for paired basic amino acid residues. DNA Cell Biol. 10, 319–328.

Benjannet, S., Rondeau N., Day R., Chretien M., Seidah N. G. (1991) PC1 and PC2 are proprotein convertases capable of cleaving proopiomelanacortin at distinct pairs of basic residues. Proc. Natl. Acad. Sci. USA 88: 3564–3568.

Bianchi A. B., Fischer S. M., Robles A. I., Rinchik E. M., Conti C. J. (1993) Overexpression of cyclin D1 in mouse skin carcinogenesis. Oncogene 8, in press.

Birkenbach M., Josefsen K., Yalamanchili R., Lenoir G., Kieff E. (1993) Epstein-Barr Virus-induced genes: First lymphocyte-specific G protein-coupled peptide receptors J. Virol. 67, 2209–2220.

Buratowski S., Hahn S., Sharp P. A., Guarente L. (1988) Function of a yeast TATA element-binding protein in a mammalian transcription system. Nature 334, 37.

Burkholder A. C. and Hartwell L. H. (1985) The yeast α-factor receptor: Structural properties deduced from the sequence of the STE2 gene. Nuc. Acids Res. 13, 8463.

Cavallini B., Huet J., Plassat, J.-L., Sentenac A., Egly J.-M., Chambon P. (1988) A yeast activity can substitute for the HeLa cell TATA box factor. Nature 334, 77.

Chen W J, Andres D. A., Goldstein J. L., Brown M. S. (1991) Cloning and expression of a cDNA encoding the subunit of rat $p21^{ras}$ protein farnesyltransferase. Cell 66: 327–334.

Choi K., Chen C.-J., Kriegler M., Roninson I. B. (1988) An altered pattern of cross-resistance in multidrug resistant human cells results from spontaneous mutation in the mdr1 (P-glycoprotein) gene. Cell 53, 519–529.

Clark K L, Dignard D., Thomas D Y, Whiteway M. (1993) Interactions among the subunits of the G proteins involved in *Saccharomyces cerevisiae* mating. Mol. Cell. Biol. 13: 1–8.

Coleman D. E., Berghuis A. M., Lee E., Linder M. E., Gilman A. G., Sprang S. R. (1994) Structures of Active Conformations of Giα1 and the Mechanism of GTP Hydrolysis. Science 265: 1405–1412.

Conklin, B. R., Farfel, Z., Lustig, K. D., Julius, D., and H. R. Blurne (1993) Substitution of three amino acids switches receptor specificity of Gqα to that of Giα. Nature 363, 274–276.

Crawford M. H., Grover F. L., Kolb W. P., McMahan C. A. et al. (1988) Complement and neutrophil activation in the pathogenesis of ischemic myocardial injury. Circulation 78: 1449–1458.

Crews C. M., Allessandrini A., Erikson R. L. (1992) The primary structure of MEK, a protein kinase that phophorylates the ERK gene product. Science 258, 478–480.

Cross F. (1988) DAF1, a mutant gene affecting size control, pheromone arrest, and cell cycle kinetics of *Saccharomyces cerevisiae*. Mol. Cell. Biol. 8, 4675–4684.

Dassa E. (1990) Cellular localization of the MALg protein from the maltose transport system in *Escherichia coli* K12. Mol. Gen. Genet. 222: 33–36.

Dassa E. and Hofnung M. (1985) Sequence of gene malG in *E. coli* K12: homologies between integral membrane components from binding protein-dependent transport systems. EMBO J. 4: 2287–2293.

Dmochowska A., Dignard D., Henning D., Thomas D. Y., Bussey H. (1987) Yeast KEX1 gene encodes a putative protease with a carboxypeptidase B-like function involved in killer toxin and α-factor precursor processing. Cell 50, 573.

Duchateau J., Haas M., Schreyen H., Radoux L. et al. (1984) Complement activation in patients at risk of developing the adult respiratory distress syndrome. Am. Rev. Respir. Dis. 130: 1058–1064.

Ehrmann M., Boyd D., Beckwith J. (1990) Genetic analysis of membrane protein topology by a sandwich gene fusion approach. Proc. Natl. Acad. Sci. 87, 7574–7578.

Elledge S. J. and Spottswood M. R. (1991) A new human p34 protein kinase, CDK2, identified by complementation of a cdc28 mutation in Saccharomyces cerevisiae, is a homolog of Xenopus Eg1. EMBO J. 10, 2653–2659.

Emter O., Mechler B., Achstetter T., Muller H., Wolf D. H. (1983) Yeast pheromone α-factor is synthesized as a high molecular weight precursor. Biochem. Biophys. Res. Commun. 116, 822–829.

Endicott J. A., Sarangi F., Ling V. (1991) Complete cDNA sequences encoding the Chinese hamster P-glycoprotein gene family. DNA Sequence 2, 89–101.

Engleman D. A., Steitz T. A., Goldman A. (1986) Identifying nonpolar transbilayer helices in amino acid sequences of membrane proteins. Ann. Rev. Biophys. Chem. 15, 321–353.

Etienne G., Armau E., Tiraby G. (1990) A screening method for antifungal substances using Saccharomyces cerevisiae strains resistant to polyene macrolides. J. Antibiot. 43, 199–206.

Fikes J. D., Becker D. M., Winston F., Guarente L. (1990) Striking conservation of TFIID in Schizosaccaharomyces pombe and Saccharomyces cerevisiae. Nature 346, 291.

Franke A. E., Andrews G. C., Stimler-Gerard N., Gerard C. J. and Showell H. J. (1988) Human C5a anaphylatoxin: Gene synthesis, expression, and recovery of biologically active material from Escherichia coli. Methods in Enzymology 162: 653–668.

Gallego C., Gupta S. K., Winitz S., Eisfelder B. J., Johnson G. L. (1992) Myristoylation of the Gαi2 polypeptide, a G protein α subunit, is required for its signaling and transformation functions. Proc. Natl. Acad. Sci. USA89, 9695–9699.

Garritsen, A., van Galen, P. J. M., and W. F. Simonds (1993) The N-terminal coilded-coil domain of β is essential for γ association: A model for G-protein βγ subunit interaction. Proc. Natl. Acad. Sci. USA 90, 7706–7710.

Gasch A. A., Hoffman M., Horikoshi M., Roeder R., Chua N. (1990) Arabodopsis thaliana contains two genes for TFIID. Nature 346, 390.

Gelfand J. A., Donelan M., Hawiger A., Burke J. F. (1982) Alternative complement pathway activation increases mortality in a model of burn injury in mice. J. Clin. Invest 70: 1170–1176.

Gerard N. P. and Gerard C. (1990) Construction and expression of a novel recombinant anaphylatoxin, C5a-N19, a probe for the human C5a receptor. Biochemistry 29, 9274–9281.

Glotzer M., Murray A. W., Kirschner M. W. (1991) Cyclin is degraded by the ubiquitin pathway. Nature 349, 132–138.

Gomez R., Goodman L E; Tripathy S K; O'Rourke E; et al. Purified yeast protein farnesyltransferase is structurally and functionally similar to its mammalian counterpart. (1993) Biochem. J. 289, 25–31.

Gotoh Y., Nishida E., Shimanuki M., Toda T., Imai Y., Yamamoto M. (1993) Schizosaccharomyces pombe SPK1 is a tyrosine-phosphorylated protein functionally related to Xenopus mitogen-activated protein kinase. Mol. Cell. Biol. 13, 6427–6434.

Graf R., Mattera R., Codina J., Estes M., Birnbaumer L. (1992) A truncated recombinant α subunit of Gi3 with a reduced affinity for βγ dimers and altered guanosine 5'-3-0-(Thio) triphosphate binding. J. Biol. Chem. 267, 24307–24314.

Gros P., Dhir R., Croop J., Talbot F. (1991) A single amino acid substitution strongly modulates the activity and substrate specificity of the mouse mdr1 and mdr3 drug efflux pumps. Proc. Natl. Acad. Sci. 88, 7289–7293.

Guarente L. (1983) Yeast promoters and lacZ fusions designed to study expression of cloned genes in yeast. Methods Enzymol. 101, 181–191.

Guarente L. (1988) UASs and enhancers: Common mechanism of transcriptional activation in yeast and mammals. Cell 52, 303.

Guarente L. in The molecular and cellular biology of the yeast Saccharomyces: Gene Expression, Jones E. W., Pringle J. R., Broach J. R., eds., Cold Spring Harbor Laboratory Press, New York, 1992, p49–98.

Hadwiger J. A., Wittenberg C., Richardson H. E., de Barros Lopes M., Reed S. I. (1989) A family of cyclin homologs that control the G1 phase in yeast. Proc. Natl. Acad. Sci. 86, 6255–6259.

Hagen D. C., McCaffrey G., Sprague G. F. (1986) Evidence the yeast STE3 gene encodes a receptor for the peptide pheromone α-factor: gene sequence and implications for the structure of the presumed receptor. Proc. Natl. Acad. Sci. 83, 1418.

Hammerschmidt D. E., Weaver L. J., Hudson L. D., Craddock P. R., Jacob H. S. (1980) Association of complement activation and elevated plasma-C5a with adult respiratory distress syndrome. Pathophysiological relevance and possible prognostic value. Lancet 1: 947–949.

Hara M., Akasaka K., Akinaga S., Okabe M., Nakano H., Gomez R., Wood D., Uh M., Tamanoi F. (1993) Identification of Ras farnesyltransferase inhibitors by microbial screening. Proc. Natl. Acad. Sci. 90, 2281–2285.

Harbury P. B., Zhang T., Kim P. S. Alber T. (1993) A switch between two-, three-, and four-stranded coiled coils in GNC4 leucine zipper mutants. Science 262, 1401–1407.

Harshman K. D., Moye-Rowley W. S., Parker C. S. (1988) Transcriptional activation by the SV40 AP-1 recognition element in yeast is mediated by a factor similar to AP-1 that is distinct from GCN4. Cell 53, 321.

He B., Chen P., Chen S.-Y., Vancura K. L., Michaelis S., Higgins C. F., Haag P. D., Nikaido K., Aedeshir F., Garcia G. et al. (1982) Complete nucleotide sequence and identification of membrane components of the histidine transport operon of S. typhimurium. Nature 298, 723–727.

Hoey T., Dynlacht B. D., Peterson M. G., Pugh B. F., Tjian R. (1990) Isolation and characterization of the Drosophila gene encoding the TATA box binding protein, TFIID. Cell 61, 1179.

Hoffman A., Sinn E., Yamamoto T., Wang J., Roy A., Horikoshi M., Roeder R. G. (1990) Highly conserved core domain and unique N terminus with presumptive regulatory motifs in a human TATA factor (TFIID). Nature 346, 387.

Howe O P. H., Draetta G., Leof E. B. (1991) Transforming growth factor 1 inhibition of p34cdc2 phosphorylation and histone H1 kinase activity is associated with G1S-phase growth arrest. Mol. Cell. Biol. 11, 1185–1194.

Hrycyna C. A., Sapperstein S. K., Clarke S., Michaelis S. (1991) The *Saccharomyces cerevisiae* STE14 gene encodes a methyltransferase that mediates C-terminal methylation of α-factor and RAS proteins. EMBO J. 10, 1699.

Hughes D. A., Ashworth A., Marshall C. J. (1993) Complementation of byr1 in fission yeast by mammalian MAP kinase kinase requires coexpression of Raf kinase. Nature 364, 349–352.

Hyde S. C., Emsley P., Hartshorn M., Mimmack M. M., Gileadi U. et al. (1990) Structural model of ATP-binding proteins associated with cystic fibrosis, multidrug resistance and bacterial transport. Nature 346, 362–365.

Jabbar, M. A., Sivasubramanian, N., Nayak, D. P. (1985) Influenza viral (AWSN33) hemagglutinin is expressed and glycosylated in the yeast *Saccharomyces cerevisiae*. Proc. Natl. Acad. Med. U.S. A. 82, 2019–2023.

Journot L., Pantaloni C., Poul M.-A., Mazarguil H., Bockaert J., Audigier Y. (1990) Amino acids 367–376 of the Gsα subunit induce membrane association when fused to soluble amino-terminal delted Giα subunit. J. Biol. Chem. 265, 9009–9015.

Julius D., Brake A., Blair L., Kunisawa R., Thorner J. (1984) Isolation of the putative structural gene for the lysine-arginine-cleaving endopeptidase required for processing of yeast prepro-α-factor. Cell 37, 1075–1089.

Julius D., Schekman, Thorner J. (1984) Glycosylation and processing of prepro-α-factor through the yeast secretory pathway. Cell 36, 309–318.

Julius D., Blair L., Brake A., Sprague G., Thorner J. (1983. Yeast α-factor is processed from a larger precursor polypeptide: the essential role of a membrane-bound dipeptidyl aminopeptidase. Cell 32, 839.

Kakidani H. and Ptashne M. (1988) GAL4 activates gene expression in mammalian cells. Cell 52, 161.

Kao C. C., Lieberman P. M., Schmidt M. C., Zhou Q., Pei R., Berk A. J. (1990) Cloning of a transcriptionally active human TATA binding factor. Science 248, 1646.

Kay B. K., Adey N. B., He Y.-S. , Manfredi J. P., Mataragnon A.H., Fowlkes D. F. (1993) An M13 phage library displaying random 38-amino-acid peptides as a source of novel sequences with affinity to selected targets. Gene 128, 59–65.

Keyomarsi K. and Pardee A. B. (1993) Redundant cyclin overexpression and gene amplification in breast cancer cells. Proc. Natl. Acad. Sci. 90, 1112–1116.

Khavari P. A., Peterson C. L., Tamkun J. W., Mendel D. B., Crabtree G. R. (1993) BRG1 contains a conserved domain of the SWI2/SNF2 family necessary for normal mitotic growth and transcription. Nature 366, 170–174.

King K., Dohlman H. G., Thorner J., Caron M. G., Lefkowitz R. J. (1990) Control of yeast mating signal transduction by a mammalian β2-adrenergic receptor and Gsα subunit. Science 250, 121–123.

Kingsman S. M., Kingsman A. J., Mellor J. (1987) The production of mammalian proteins in *Saccharomyces cerevisiae*. TIBTECH 5, 53–57.

Koff A., Cross F., Fisher A., Schumacher J., Leguellec K., Phillipe M., Roberts J. M. (1991) Human cyclin E, a new cyclin that interacts with two members of the CDC2 gene family. Cell 66, 1217–1228.

Koff A., Ohtsuli M., Polyak K., Roberts J. M. Massagué J. (1993) Negative regulation of Gl in mammalian cells: inhibition of cyclin E-dependent kinase by TGF-β. Science 260, 536–539.

Kohl N. E., Mosser S., deSolms S. J., Giuliani E. A., Pompliano D. L., Graham S. L., Smith R. L., Scolnick E. M., Oliff A., Gibbs J. B. (1993) Selective inhibition of ras-dependent transformation by a farnesyltransferase inhibitor. Science 260, 1934–1937.

Kohl N. E., Diehl R. E., Schaber M. D., Rands E., Soderman D. D., He B., Moores S. L., Pompliano D. L., Ferro-Novick S., Powers S. et al. (1991) Structural homology among mammalian and *Saccharomyces cerevisiae* isoprenyl-protein transferases. J. Biol. Chem. 266, 18884–18888.

Korner, J., Chun J., Harter D., Axel R. (1991) Isolation and functional expression of a mammalian prohormone processing enzyme, murine prohormone convertase 1. Proc. Natl. Acad. Sci USA 88: 6834–6838.

Kouba M; Vanetti M; Wang X; Schafer M; Hollt V (1993) Cloning of a novel putative G-protein-coupled receptor (NLR) which is expressed in neuronal and lymphatic tissue. FEBS Lett 321, 173–178.

Kramer R. A., Schaber M. D., Skalka A. M., Ganguly K., Wong-Staal F., Reddy E. P. (1086) HTLV-III gag protein is processed in yeast cells by the virus pol-protease.

Kreil G. (1990) Processing of precursors by dipeptidylaminopeptidases: a case of molecular ticketing. Trends Biochem. Sci. 15, 23.

Kuchler K., Sterne R. E., Thorner J. (1989) *Saccharomyces cerevisiae* STE6 gene product: a novel pathway for protein export in eukaryotic cells. EMBO J. 8, 3973.

Kurjan, J., Herskowitz, I. (1982) Structure of a yeast pheromone gene (MF): a putative α-factor precursor contains four tandem copies of mature α-factor. Cell 30, 933–943.

Kurjan J. (1985) α-factor structural gene mutations in yeast: effects on α-factor production and mating. Mol. Cell. Biol. 5, 787–796.

Kyte and Doolittle (1982) A simple method for displaying the hydropathic character of a protein. J. Molec. Biol. 157, 105–132.

Lambright D G, Noel J P, Hamm, H E, Sigler, P B (1994) Structural determinants for activation of the α-subunit of a heterotrimeric G protein. Nature 369: 621–628.

Lammie G. A., Fantl V., Smith R., Schuuring E., Brookes S., Michalides R., Dickson C., Arnold A. Peters G. (1991) D11S287, a putative oncogene on chromosome 11q13, is amplified and expressed in squamous cell and mammary carcinomas and linked to BCL-1. Oncogene 6, 439–444.

Leberer E., Dignard D., Hougan L., Thomas D Y, Whiteway M. (1992) Dominant-negative mutants of a yeast G-protein b subunit identify two functional regions involved in pheromone signalling. EMBO J. 11: 4805–4813.

Lee E., Taussig R., Gilman A. G. (1992) The G226A Mutant of Gsα Highlights the Requirement for Dissociation of G Protein Subunits. J. Biol. Chem. 267: 1212–1218.

Lee K. S. , Irie K., Gotoh Y., Watanabe Y., Arakai H., Nishida E., Matsumoto K., Levin D. E. (1993) A yeast mitogen-activated protein kinase homolog (Mpk1p) mediates signalling by protein kinase C. Mol. Cell. Biol. 13, 3067–3075.

Lee M. G. and Nurse P. (1987) Complementation used to clone a human homologue of the fission yeast cell cycle control gene cdc2. Nature 327, 31–35.

Lew D. J., Dulic V., Reed S. I. (1991) Isolation of three novel human cyclins by rescue of G1 cyclin (Cln) function in yeast. Cell 66, 1197–1206.

Linder M. E., Pang I.-H., Duronio R. J., Gordon J. I., Sternweis P. C., Gilman A. G. (1991) J. Biol. Chem. 266, 4654–4659.

Lupas, A. N., Lupas J. M., Stock J. B. (1992) Do G protein subunits associate via a three-stranded coiled coil? FEBS Lett. 314, 105–108.

Ma J., Przibilla J., Bogorad L., Ptashne M. (1988) Yeast activators stimulate plant gene expression. Nature 334, 631.

Manney T. R., Duntze W., Betz R. (1981) The isolation, characterization, and physiological effects of the *S. cerevisiae* sex pheromones. In Sexual interactions in eukaryotic microbes (ed. D. H. O'Day et al.), p 21. Academic Press, New York.

Masters, Stroud, and Bourne (1986) Protein Engineering 1: 47–54.

Matsushime H., Roussel M. F., Ashmun R. A., Scherr C. J. (1991) Colony-stimulating factor 1 regulates novel cyclins during the G1 phase of the cell cycle. Cell 65, 701–713.

McDonnell D. P., Nawaz Z., Densmore C., Weigel N. L. et al. (1991) High level expression of biologically active estrogen receptor in *Saccharonyces cerevisiae*. J. Steroid Biochem. Mol. Biol. 39, 291–297.

Metzger, D., Losson R., Bornert J. M., Lemoine Y., Chambon P. (1992) Promoter specificity of the two transcriptional activation functions of the human oestrogen receptor in yeast. Nuc. Acids Res. 20, 2813–2817.

Metzger D., White J. H., Chambon P. (1988) The human oestrogen receptor functions in yeast. Nature 334, 31.

Milano, C. A., Allen, L. F., Rockman, H. A., Dolber, P. C., McMinn, T. R., Chien, K. R., Johnson, T. D., Bond R. A., Lefkowitz R. J. (1994) Enhanced myocardial function in transgenic mice overexpressing the β-adrenergic receptor. Science 264, 582–586.

Mimura C. S., Holbrook S. R., Ames G. F.-L. (1991) Structural model of the nucleotide binding conserved component of periplasmic permeases. Proc. Natl. Acad. Sci. 88, 84–88.

Moir D T; Davidow L S. (1991) Production of proteins by secretion from yeast. Methods Enzymol 194, 491–507.

Motokura T., Bloom T., Kim H. G., Juppner H., Ruderman J. V., Kronenberg H. M., Arnold A. (1991) A novel cyclin encoded by a bcl1-linked candidate oncogene. Nature 350, 512–515.

Moye-Rowley W. S., Harshman K. D., Parker C. S. (1989) Yeast YAP1 encodes a novel form of the jun family of transcriptional activator proteins. Genes Dev. 3, 283.

Mumby, S. M., Heukeroth R. O., Gordon J. I., Gilman A. G. (1990) G protein Gα-subunit expression, myristoylation, and membrane association in COS cells. Proc. Natl. Acad. Sci. USA 87, 728–732.

Nakafuku M., Itoh H. Nakamura S., Kazioro Y. (1987) Occurrence in *Saccharomyces cerevisiae* of a gnee homologous to the cDNA coding for the a subunit of mammalian G proteins. Proc. Natl. Acad. Sci. 84, 2140–2144.

Nakagawa T., Hosaka M., Torii S., Watanabe T. et al. (1993) Identification and functional expression of a new member of the mammalian Kex-2-like processing endoprotease family: its striking structural similarity to PACE4. J. Biochem. (Tokyo) 113, 132–135.

Nakayama K., Hosaka M., Hatsuzawa K., Murakami K. (1991) Cloning and functional expression of a novel endoprotease involved in prohormone processing at dibasic sites. J. Biochem. 109, 803–806.

Nakayama K., Kim W. S., Torii S., Hosaka M. et al. (1992) Identification of a fourth member of the mammalian endoprotease family homologous to the yeast Kex2 protease. Its testis specific expression. J. Biol. Chem. 267, 5897–5900.

Nakayama N., Miyajima A., Arai K. (1985) Nucleotide sequences of STE2 and STE3, cell type-specific sterile genes from *Saccharomyces cerevisiae*. EMBO J. 4, 2643.

Nash R., Tokiwa G. Awand S., Erickson K., Futcher A. B. (1988) WHI1+ gene of *Saccharomyces cerevisiae* tethers division to cell size and is a cyclin homolog. EMBO J. 7, 4335–4346.

Neer E. J., Pulsifer L., Wolf L. G. (1988) The amino terminus of G protein α subunits is required for interaction with βγ. J. Biol. Chem. 263, 8996–9000.

Neiman A. M., Stevenson B. J., Xu H. P., Sprague G. F. et al. (1993) Functional homology of protein kinases required for sexual differentiation in *Schizosaccharomyces pombe* and *Saccharomyces cerevisiae* suggests a conserved signal transduction module in eukaryotic organisms. Mol. Biol. Cell. 4, 107–120.

Neote, K. DiGregorio, D., Mak, J. Y., Horuk, R., and Schall, T. J. (1993) Molecular cloning, functional expression, and signaling characteristics of a C-C chemokine receptor. Cell 72, 415–425.

Noel J. P., Hamm H. E., Sigler P. B. (1993) The 2.2 A crystal structure of transducin-α complexed with GTPγS. Nature 366, 654–663.

Norman C., Runswick M., Pollock R., Treisman R. (1988) Isolation and properties of cDNA clones encoding SRF, a transcription factor that binds to the c-fos serum response element. Cell 55, 989.

Oeda, K., Sakaki, T., Ohkawa, H. (1985) Expression of rat liver cytochrome P-450MC cDNA in *Saccharomyces cerevisiae*. DNA 3, 203–210.

Ogden, J. E., Stanway, C., Kuim, S., Mellor, J., Kingsman, A. J., and Kingsman, S. M. (1986) Efficient expression of the *Saccharomyces cerevisiae* PGK gene depends on an upstream activation sequence but does not require TATA sequences. Mol. Cell. Biol. 6, 4335.

Olson L. M., Moss G. S., Baukus O., Das Gupta T. K. (1985) The role of C5 in septic lung injury. Ann. Surg. 202: 771–776.

Overduin P., Boos W., Tomassen J. (1988) Nucleotide sequence of the ugp genes of *Escherichia coli* K-12: homology to the maltose system. Mol. Microbiol. 2, 767–775.

Peterson M. G., Tanese N., Pugh B. F., Tjian R. (1990) Functional domains and upstream activation properties of cloned human TATA binding protein. Science 248, 1625.

Pines J. and Hunter T. (1990) Human cyclin A is adenovirus E1A-associated protein p60 and behaves differently from cyclin B. Nature 346, 760–763.

Powers S. (1991) RAM2, an essential gene of yeast, and RAM1 encode the two polypeptide components of the farnesyltransferase that prenylates a-factor and Ras proteins. Proc Natl Acad Sci 88: 11373–11377.

Pronin, A. N., and N. Gautam (1992) Interaction between G-protein: β and γ subunit types is selective. Proc. Natl. Acad. Sci. USA 89: 6220–6224.

Rarick H. M., Artemyev, N. O., and Hamm, H. E. A site on rod G protein α subunit that mediates effector activation. (1992) Science 256, 1031–1033.

Reyes M., Treptow M. A., Schuman H. A. (1986) Transport of p-nitrophenyl-maltoside by the maltose transport system of *Escherichia coli* and its subsequent hydrolysis by a cytoplasmicα-maltosidase. J. Bacteriol. 165, 918–922.

Rogers S., Wells R., Rechsteiner M. (1986) Amino acid sequences common to rapidly degraded proteins: the PEST hypothesis. Science 234, 364–368.

Russell M. and Johnson G. L. (1993) G protein N-terminal αi2/αs chimeras reveal amino acids important in regulating as activity. Mol. Pharmacol. 44: 255–263

Scharer, E. and R. Iggo (1992). Mammalian p53 can function as a transcription factor in yeast."Nuc. Acids Res. 20 (7): 1539–1545.

Schafer W. R., Kim R., Sterne R., Thorner J., Kim S.-H., Rine J. (1989) Genetic and pharmacological suppression of oncogenic mutations in RAS genes of yeast and humans. Science 245, 379.

Schafer W. R., Trueblood C. E., Yang C.-C., Maayer M. P., Rosenberg S. , Poulter C. D., Kim S.-H., Rine J. (1990) Enzymatic coupling of cholesterol intermediates to a mating pheromone precursor and to the Ras protein. Science 249, 1133.

Schena M. and Yamamoto K.R. (1988) Mammalian glucocorticoid receptor derivatives enhance transcription in yeast. Science 241, 965.

Scherr C. J. (1993) Mammalian G1 cyclins. Cell 73, 1059–1065.

Schultz R. M., Silberman S., Persky B. et al. (1988) Inhibition by human recombinant tissue inhibitor of metalloproteinases of human amion invasion and lung colonization by murine B16-F10 melanoma cells. Cancer Res. 48, 5539.

Seideh N. G., Fournier H., Boileau G., Benjannet S. et al. (1992) The cDNA structure of the procine pro-hormone convertase PC2 and the comparative processing by PC1 and PC2 of the N-terminal glycopeptide segment of porcine POMC. FEBS Lett., 310, 235–239.

Singh A., Chen E. Y., Lugovoy J. M., Chang C. N., Hitzman R. A., Seeburg P. H. (1983) *Saccharomyces cerevisiae* contains two discrete genes coding for the α-factor pheromone. Nuc. Acids Res. 11, 4049–4063.

Slepak V. Z., Wilkie T. M., Simon, M. I. (1993) Mutational analysis of G protein α subunit Goα expressed in *Escherichia coli*. J. Biol. Chem. 268, 1414–1423.

Smeekens S. P. and Steiner D. F. (1990) Identification of a human insulinoma CDNA encoding a novel mammalian protein structurally related to the yeast dibasic processing protease Kex2. J. Biol. Chem. 265, 2997–3000.

Speigel A. M., Backlund P. S., Jr., Butrynski J. E., Zones T. L. J., Simonds W. F. (1991) The G protein connection-:molecular basis of membrane association. TIBS 16, 338–3441.

Steube K; Chaudhuri B; Marki W; Merryweather JP; Heim J. α-factor-leader-directed secretion of recombinant human insulin-like growth factor I from *Saccharomyces cerevisiae*. Precursor formation and processing in the yeast secretory pathway. (1991) Eur J Biochem 198, 651–657.

Strubin M. and Struhl K. (1992) Yeast and human TFIID with altered DNA-binding specificity for TATA elements. Cell 68, 721–730.

Struhl, K. (1986) Constitutive and inducible *Saccharomyces cerevisiae* promoters: Evidence for two distinctive molecular mechanisms. Mol. Cell. Biol. 6, 3847.

Struh, K. (1989) Molecular mechanisms of transcriptional regulation in yeast. Annu. Rev. Biochem. 58, 1051.

Sullivan, K. A., et al(1987) Nature 330, 758–760

Takahashi, H., Hakamata Y., Watanabe Y., Kikuno R. et al. (1983) Complete nucleotide sequence of the human corticotropin-beta-lipotropin precursor gene. Nucleic Acids Research 11: 6847–6858.

Thomas G., Thorne B. A., Thomas L., Allen R. G., Hruby D. E., Fuller R., Thorner J. (1988) Yeast KEX2 endopeptidase correctly cleaves a neuroendocrine prohormone in mammalian cells. Science 241, 226.

Thomas L., Cooper A., Bussey H., Thomas G. (1990) Yeast KEX1 protease cleaves a prohormone processing intermediate in mammalian cells. J. Biol. Chem. 265, 10821.

Valdiva R. H., Wang L., Winans S. C. (1991) Characterization of a putative periplasmic transport system for octopine accumulation encoded by Agrobacterium tumefaciens T: plasmid pTi46. J. Bacteriol. 173, 6398–6405.

Vogt P. K., Bos T. J., Doolittle R. F. (1987) Homology between the DNA-binding domain of the GCN4 regulatory protein of yeast and the carboxy-terminal region of a protein coded for by the oncogene jun. Proc. Natl. Acad. Sci. 84, 3316.

Waters M. G., Evans E. A., Blobel G. (1988) Prepro-α-factor has a cleavable signal sequence. J. Biol. Chem. 263, 6209.

Webster N., Jin J. R., Green S., Hollis M., Chambon P. (1988) The yeast $UAS_G$ is a transcriptional enhancer in human HeLa cells in the presence of the GAL4 transactivator. Cell 52, 169.

Weisman H. F., Bartow T., Leppo M. K., Marsh H. C. Jr. et al. (1990) Soluble human complement receptor type 1: in vivo inhibitor of complement suppressing post-ischemic myocardial inflammation and necrosis. Science 249: 146–151.

West, J. P. et al (1985) J. Biol. Chem. 260, 14428–14430.

Whiteway M., Clark K. L, Leberer E., Degnard D., and Thomas D. Y. (1994) Genetic Identification of Residues Involved in Association of α and β G-Protein Subunits. Mol. Cell. Biol. 14: 3233–3239.

Wood C. R., Boss M. A., Kenten J. H., Calvert J. E., Roberts N. A., Emtage J. S. (1985) The synthesis and in vivo asembly of functional antibodies in yeast. Nature 314, 446–449.

Xiong Y., Connolly T., Futcher B., Beach D. (1991) Human D-type cyclin. Cell 65, 691–699.

We claim:

1. A haploid yeast cell engineered to express a mammalian adenylyl cyclase and a mammalian or chimeric G protein subunit, said mammalian adenylyl cyclase being functional and regulatable in said cell even in the absence of expression of a mammalian G protein-coupled receptor by the yeast cell.

2. The yeast cell of claim 1, wherein the mammalian or chimeric G protein subunit is a mammalian or chimeric Gα subunit, said mammalian adenylyl cyclase being activatable or inhibitable by said Gα subunit.

3. The yeast cell of claim 1, wherein the mammalian or chimeric G protein subunit is a mammalian or chimeric Gβγ complex, said mammalian adenylyl cyclase being activatable or inhibitable by said Gβγ complex.

4. The yeast cell of claim 1, 2 or 3, wherein the expression of the endogenous yeast adenylyl cyclase is not functional.

5. The yeast cell of claim 4, wherein the expression of the endogenous yeast adenylyl cyclase is temperature sensitive.

6. The yeast cell of claim 5, wherein the cell comprises the mutant allele cdc35-1.

7. The yeast cell of claim 1 wherein the endogenous yeast adenylyl cyclase is inactivated.

8. The yeast cell of claim 1, 2 or 3, wherein the mammalian adenylyl cyclase is selected from the group consisting of a type 1, a type 2, a type 3, a type 4, a type 5, a type 6, a type 7, and a type 8 adenylyl cyclase.

9. The yeast cell of claim 1, 2 or 3, wherein the mammalian or chimeric G protein subunit is derived from the same mammalian species as the adenylyl cyclase.

10. The yeast cell of claim 1, 2 or 3, wherein the mammalian adenylyl cyclase is expressed from a gene integrated into the yeast chromosome.

11. The yeast cell of claim 1, 2 or 3, wherein the yeast cell further comprises a marker gene comprising a cyclic AMP responsive promoter and encoding a selectable or screenable gene product.

12. The yeast cell of claim 2, said yeast cell further expressing a Gβ subunit and a Gγ subunit capable of associating to form a Gβγ complex, said Gα subunit, Gβ subunit and Gγ subunit being capable of associating to form a heterotrimeric mammalian or heterotrimeric chimeric G protein.

13. The yeast cell of claim 1, 2 or 3, said cell further expressing a mammalian G protein-coupled receptor which is capable of interacting with said mammalian or chimeric G protein subunit.

14. The yeast cell of claim 12, further comprising a mutation in a yeast G protein subunit gene such that the endogenous G protein subunit is not expressed in functional form.

15. The yeast cell of claim 1, 2 or 3, which displays a Cam phenotype.

16. The yeast cell of claim 15, which comprises a cam1 cam2, or cam3 mutation.

17. The yeast cell of claim 1, 2 or 3, wherein the cell is diploid.

18. The yeast cell of claim 2, wherein the mammalian or chimeric Gα subunit is a mammalian or chimeric Gαs subunit.

19. The yeast cell of claim 2, which further coexpresses a mammalian or chimeric Gαi which inhibits said mammalian adenylyl cyclase.

20. A method of identifying a modulator of mammalian adenylyl cyclase activity which comprises exposing the yeast cell of claim 1 to a test substance and determining whether mammalian adenylyl cyclase activity is modulated in said cell to thereby identify the test substance as a modulator of mammalian adenylyl cyclase activity.

21. The method of claim 20, wherein the test substance activates mammalian adenylyl cyclase activity in the yeast cell and the test substance is identified as an activator of mammalian adenylyl cyclase activity.

22. The method of claim 20, wherein the test substance inhibits mammalian adenylyl cyclase activity in the yeast cell and the test substance is identified as an inhibitor of mammalian adenylyl cyclase activity.

23. The method of claim 20 wherein modulation of mammalian adenylyl cyclase activity is correlatable with cell growth, or activity of a reporter gene, under predetermined selective conditions.

24. A method of identifying a substance which antagonizes or enhances the modulatory effect of a mammalian Gα subunit on the activity of a mammalian adenylyl cyclase, which comprises exposing the yeast cell of claim 2 to a test substance and determining whether the level of mammalian adenylyl cyclase activity is changed.

25. A method according to claim 24, wherein the mammalian Gα subunit is a Gαi subunit and the modulatory effect of the Gαi subunit is inhibition of adenylyl cyclase activity.

26. The method of claim 24, wherein the yeast cell is further engineered to express a mammalian or chimeric Gβγ complex, said mammalian adenylyl cyclase being activatable or inhibitable by said Gβγ complex.

27. The method of claim 24, wherein the yeast cell further expresses a Gβ subunit and a Gγ subunit capable of associating to form a Gβγ complex, said Gα subunit, Gβ subunit and Gγ subunit being capable of associating to form a heterotrimeric mammalian or heterotrimeric chimeric G protein.

28. The method of claim 24, wherein the mammalian or chimeric Gα subunit is a mammalian or chimeric Gαs subunit.

29. The method of claim 24, wherein the yeast cell further coexpresses a mammalian or chimeric Gαi which inhibits said mammalian adenylyl cyclase.

30. A method of identifying a substance which antagonizes or enhances the modulatory effect of a mammalian G protein subunit on the activity of a mammalian adenylyl cyclase, which comprises exposing the yeast cell of claim 3 to a test substance and determining whether the level of the adenylyl cyclase activity is changed.

31. The method of claim 30, wherein the yeast cell is further engineered to co-express a mammalian or chimeric Gα subunit, said mammalian adenylyl cyclase being activatable or inhibitable by said Gα subunit.

32. The method of claim 20, 24 or 30, wherein the yeast cell expresses a nonfunctional endogenous yeast adenylyl cyclase.

33. The method of claim 32, wherein the expression of the endogenous yeast adenylyl cyclase is temperature sensitive.

34. The method of claim 33, wherein the cell comprises the mutant allele cdc35-1.

35. The method of claim 32 wherein the endogenous yeast adenylyl cyclase is inactivated.

36. The method of claim 20, 24 or 30 wherein the mammalian adenylyl cyclase is selected from the group consisting of a type 1, a type 2, a type 3, a type 4, a type 5, a type 6, a type 7, and a type 8 adenylyl cyclase.

37. The method of claim 20, 24, or 30, wherein the mammalian or chimeric G protein subunit is derived from the same mammalian species as the adenylyl cyclase.

38. The method of claim 20, 24 or 30, wherein said yeast cell further expresses a mammalian G protein-coupled receptor which is capable of interacting with said mammalian or chimeric G protein subunit.

39. The method of claim 20, 24 or 30, wherein the yeast cell further comprises a mutation in a yeast G protein subunit gene such that the endogenous G protein subunit is not expressed in functional form.

40. The method of claim 20, 24 or 30, which displays a Cam phenotype.

41. The method of claim 40, wherein the yeast cell comprises a cam1, cam2, or cam3 mutation.

42. A yeast cell engineered to express a mammalian adenylyl cyclase and a mammalian or chimeric G protein subunit, said mammalian adenylyl cyclase being functional and regulatable in said cell.

43. The yeast cell of claim 42, wherein said mammalian adenylyl cyclase is functional and regulatable even in the absence of expression of a mammalian G protein-coupled receptor by the yeast cell.

44. The yeast cell of claim 42, wherein the mammalian or chimeric G protein subunit is a mammalian or chimeric Gα subunit, said mammalian adenylyl cyclase being activatable or inhibitable by said Gα subunit.

45. The yeast cell of claim 42, wherein the mammalian or chimeric G protein subunit is a mammalian or chimeric Gβγ complex, said mammalian adenylyl cyclase being activatable or inhibitable by said Gβγ complex.

46. The yeast cell of claim 42, 43, 44, or 45, wherein the expression of the endogenous yeast adenylyl cyclase is not functional.

47. The yeast cell of claim 46, wherein the expression of the endogenous yeast adenylyl cyclase is temperature sensitive.

48. The yeast cell of claim 47, wherein the cell comprises the mutant allele cdc35-1.

49. The yeast cell of claim 42 wherein the endogenous yeast adenylyl cyclase is inactivated.

50. The yeast cell of claim 42, 43, 44 or 45, wherein the mammalian adenylyl cyclase is selected from the group consisting of a type 1, a type 2, a type 3, a type 4, a type 5, a type 6, a type 7, and a type 8 adenylyl cyclase.

51. The yeast cell of claim 42, 43, 44 or 45, wherein the mammalian or chimeric G protein subunit is derived from the same mammalian species as the adenylyl cyclase.

52. The yeast cell of claim 42, 43, 44 or 45, wherein the mammalian adenylyl cyclase is expressed from a gene integrated into the yeast chromosome.

53. The yeast cell of claim 42, 43, 44 or 45, wherein the yeast cell further comprises a marker gene comprising a cyclic AMP responsive promoter and encoding a selectable or screenable gene product.

54. The yeast cell of claim 44, said yeast cell further expressing a Gβ subunit and a Gγ subunit capable of associating to form a Gβγ complex, said Gα subunit, Gβ subunit and Gγ subunit being capable of associating to form a heterotrimeric mammalian or heterotrimeric chimeric G protein.

55. The yeast cell of claim 42, 43, 44 or 45, said cell further expressing a mammalian G protein-coupled receptor which is capable of interacting with said mammalian or chimeric G protein subunit.

56. The yeast cell of claim 53, further comprising a mutation in a yeast G protein subunit gene such that the endogenous G protein subunit is not expressed in functional form.

57. The yeast cell of claim 42, 43, 44 or 45, which displays a Cam phenotype.

58. The yeast cell of claim 56, which comprises a cam1, cam2, or cam3 mutation.

59. The yeast cell of claim 42, 43, 44 or 45, wherein the cell is diploid.

60. The yeast cell of claim 44, wherein the mammalian or chimeric Gα subunit is a mammalian or chimeric Gαs subunit.

61. The yeast cell of claim 44, which further coexpresses a mammalian or chimeric Gαi which inhibits said mammalian adenylyl cyclase.

62. A method of identifying a modulator of mammalian adenylyl cyclase activity which comprises exposing the yeast cell of claim 42 to a test substance and determining whether mammalian adenylyl cyclase activity is modulated in said cell to thereby identify the test substance as a modulator of mammalian adenylyl cyclase activity.

63. The method of claim 62, wherein the test substance activates mammalian adenylyl cyclase activity in the yeast cell and the test substance is identified as an activator of mammalian adenylyl cyclase activity.

64. The method of claim 62, wherein the test substance inhibits mammalian adenylyl cyclase activity in the yeast cell and the test substance is identified as an inhibitor of mammalian adenylyl cyclase activity.

65. The method of claim 62, wherein modulation of mammalian adenylyl cyclase activity is correlatable with cell growth, or activity of a reporter gene, under predetermined selective conditions.

66. A method of identifying a substance which antagonizes or enhances the modulatory effect of a mammalian Gα subunit on the activity of a mammalian adenylyl cyclase, which comprises exposing the yeast cell of claim 44 to a test substance and determining whether the level of mammalian adenylyl cyclase activity is changed.

67. A method according to claim 65, wherein the mammalian Gα subunit is a Gαi subunit and the modulatory effect of the Gβγ subunit is inhibition of adenylyl cyclase activity.

68. The method of claim 65, wherein the yeast cell is further engineered express a mammalian or chimeric Gβγ complex, said mammalian adenylyl cyclase being activatable or inhibitable by said Gβγ complex.

69. The method of claim 65, wherein the yeast cell further expresses a Gβ subunit and a Gγ subunit capable of associating to form a Gβγ complex, said Gα subunit, Gβ subunit and Gγ subunit being capable of associating to form a heterotrimeric mammalian or heterotrimeric chimeric G protein.

70. The method of claim 65, wherein the mammalian or chimeric Gα subunit is a mammalian or chimeric Gαs subunit.

71. The method of claim 62, wherein the yeast cell further coexpresses a mammalian or chimeric Gαi which inhibits said mammalian adenylyl cyclase.

72. A method of identifying a substance which antagonizes or enhances the modulatory effect of a mammalian G protein subunit on the activity of a mammalian adenylyl cyclase, which comprises exposing the yeast cell of claim 45 to a test substance and determining whether the level of the adenylyl cyclase activity is changed.

73. The method of claim 72, wherein the yeast cell is further engineered to co-express a mammalian or chimeric Gα subunit, said mammalian adenylyl cyclase being activatable or inhibitable by said Gα subunit.

74. The method of claim 62, 65, or 72, wherein the yeast cell expresses a nonfunctional endogenous yeast adenylyl cyclase.

75. The method of claim 73, wherein the expression of the endogenous yeast adenylyl cyclase is temperature sensitive.

76. The method of claim 75, wherein the cell comprises the mutant allele cdc35-1.

77. The method of claim 62, 65, or 72, wherein the endogenous yeast adenylyl cyclase is inactivated.

78. The method of claim 62, 65 or 72 wherein the mammalian adenylyl cyclase is selected from the group consisting of a type 1, a type 2, a type 3, a type 4, a type 5, a type 6, a type 7, and a type 8 adenylyl cyclase.

79. The method of claim 62, 65 or 72 wherein the mammalian or chimeric G protein subunit is derived from the same mammalian species as the adenylyl cyclase.

80. The method of claim 62, 65 or 72, wherein said yeast cell further expresses a mammalian G protein-coupled receptor which is capable of interacting with said mammalian or chimeric G protein subunit.

81. The method of claim 62, 65 or 72, wherein the yeast cell further comprises a mutation in a yeast G protein subunit gene such that the endogenous G protein subunit is not expressed in functional form.

82. The method of claim 62, 65 or 72, which displays a Cam phenotype.

83. The method of claim 82, wherein the yeast cell comprises a cam1, cam2, or cam3 mutation.

* * * * *